(12) United States Patent
Reynolds et al.

(10) Patent No.: US 11,977,309 B2
(45) Date of Patent: May 7, 2024

(54) ANODICALLY COLORING ELECTROCHROMIC MOLECULES, MATERIALS, AND DEVICES, AND METHODS OF MAKING AND USE THEREOF

(71) Applicant: Georgia Tech Research Corporation, Atlanta, GA (US)

(72) Inventors: John Robert Reynolds, Atlanta, GA (US); Dylan T. Christiansen, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 763 days.

(21) Appl. No.: 16/762,935

(22) PCT Filed: Nov. 20, 2018

(86) PCT No.: PCT/US2018/062043
§ 371 (c)(1),
(2) Date: May 10, 2020

(87) PCT Pub. No.: WO2019/143401
PCT Pub. Date: Jul. 25, 2019

(65) Prior Publication Data
US 2020/0393732 A1    Dec. 17, 2020

Related U.S. Application Data

(60) Provisional application No. 62/588,512, filed on Nov. 20, 2017.

(51) Int. Cl.
| | | |
|---|---|---|
| *C07D 495/00* | (2006.01) | |
| *C07D 495/04* | (2006.01) | |
| *C07D 519/00* | (2006.01) | |
| *C08G 75/00* | (2006.01) | |
| *C09K 9/02* | (2006.01) | |
| *G02F 1/1523* | (2019.01) | |

(52) U.S. Cl.
CPC .......... *G02F 1/1525* (2013.01); *C07D 495/04* (2013.01); *C07D 519/00* (2013.01); *C08G 75/00* (2013.01); *C09K 9/02* (2013.01)

(58) Field of Classification Search
CPC .................................................. C07D 495/00
See application file for complete search history.

(56) References Cited

U.S. PATENT DOCUMENTS

| | | |
|---|---|---|
| 5,521,745 A | 5/1996 | Silver et al. |
| 2009/0078917 A1 | 3/2009 | Percec et al. |
| 2015/0031894 A1 | 1/2015 | Yamada et al. |
| 2015/0153624 A1 | 6/2015 | Yamada et al. |
| 2016/0306251 A1 | 10/2016 | Yamamoto et al. |
| 2017/0267811 A1 | 9/2017 | Reynolds et al. |
| 2017/0267920 A1 | 9/2017 | Kerszulis et al. |

OTHER PUBLICATIONS

American Chemical Society. Chemical Abstract Service. RN 2101742-77-0. Entered into STN on Jul. 11, 2017. (Year: 2017).*
American Chemical Society. CAS RN 95710-71-7. Entered into STN: Apr. 6, 1985. (Year: 1985).*
Christiansen, Dylan T., et al. "New Design Paradigm for Color Control in Anodically Coloring Electrochromic Molecules." J Am Chem Soc. (2019), vol. 141, pp. 3859-3862. (Year: 2019).*
European Search Report for EP Application No. 18901665.2 mailed Jun. 30, 2021.
International Search Report issued for PCT/US2018/062043, mailed Aug. 22, 2019.

* cited by examiner

*Primary Examiner* — John S Kenyon
(74) *Attorney, Agent, or Firm* — Thomas | Horsteyemer, LLP

(57) ABSTRACT

A variety of anodically-coloring electrochromic molecules are provided. In particular, anodically-coloring electrochromic molecules and devices are provided that allow for tuning the absorption bands in the cation state across the visible spectrum while demonstrating little to no coloring or visible absorption in the neutral state, resulting in high-contrast devices. Electrochromic devices are also provided, as well as methods of making the devices and molecules, and methods of use thereof.

4 Claims, 34 Drawing Sheets

ANODICALLY COLORING ELECTROCHROMIC MOLECULES, MATERIALS, AND DEVICES, AND METHODS OF MAKING AND USE THEREOF

CROSS-REFERENCE TO RELATED APPLICATIONS

This application is a National Stage of International Application No. PCT/US2018/062043, filed Nov. 20, 2018, which claims priority to, and the benefit of, U.S. provisional application entitled "ANODICALLY COLORING MOLECULAR ELECTROCHROMICS" having Ser. No. 62/588,512, filed Nov. 20, 2017.

STATEMENT REGARDING FEDERALLY SPONSORED RESEARCH OR DEVELOPMENT

This invention was made with government support under award FA9550-18-1-0184, award FA9550-18-1-0034, award FA9550-14-1-0271, and award FA9550-15-1-0181 awarded by the Air Force Office of Scientific Research. The government has certain rights in the invention.

TECHNICAL FIELD

The present disclosure generally relates to electrochromic materials and devices.

BACKGROUND

Electrochromism is the change of a material's color upon the application of an electrochemical potential. Easily oxidized, cathodically coloring, organic polymer electrochromes have been the focus of a large thrust of research because of their benefits of solution processability, mechanical flexibility, device bistability, and access to a variety of primary and secondary colors. Fine control of the visible spectra, and ultimately color, of these materials has been accomplished using the variables of heterocycle choice, electron rich/poor character, steric strain, and copolymerization. Applications include full color passive and active displays, energy saving tinted windows, switchable mirrors, and dimmable visors, goggles and glasses for military and/or recreational use.

The history of research in fully conjugated cathodically coloring ECPs has yielded materials that span the entire color palette. These polymers can be spray cast to form vividly colored films that upon oxidation become highly transmissive in the visible region. Recently, approaches towards creating black-to-transmissive electrochromic polymeric materials have been investigated through the generation of broadly absorbing copolymers or via solution mixing of polymeric inks. The latter of the two approaches allows for finer control, more accurate reproducibility, and higher contrast through the mixing of cyan, magenta, and yellow materials to create a broadly absorbing blend.

Although cathodically coloring polymers provide precise control of color and electrochemical properties, they have an inherent challenge when it comes to making improvements in contrast, which is explored in Christiansen, Dylan T.; Wheeler, David L.; Tomlinson, Aimée L.; and Reynolds, John R. *Polymer Chemistry* 2018; 9, 3055-3066 and depicted in FIG. 1. In the charge neutral state conjugated ECPs absorb in the visible with a single $\pi$-$\pi$* transition (exceptions include donor-acceptor systems that have dual band absorbances and some random copolymers that have a manifold of absorbances). The oxidation states for a single polymer chain in solution consists of dual transition polarons (b and c) and single transition bipolarons (d) with discrete absorbances at longer wavelengths than the neutral polymer. In the solid-state, charged states interact with one another creating a complex system where selection rules are relaxed and more transitions are possible. This leads to the characteristically broad profile for the oxidized states of fully conjugated ECPs (e). An asymmetric absorption throughout the visible region, absorbing more low energy red light and transmitting more of the higher energy blue light, manifests itself in such a way that highly oxidized states of conjugated ECPs exhibit a transmissive grey-blue hue even in the highest contract materials. Reaching a color neutral and fully transmissive oxidized state across the entire visible spectrum has proven difficult due to this relaxation of the selection rules allowing broad light absorption in these materials.

There remains a need for improved electrochromic materials that overcome the aforementioned deficiencies.

SUMMARY

In various aspects, anodically-coloring electrochromic molecules and electrochromic devices containing anodically-coloring electrochromic molecules are provided that overcome one or more of the aforementioned deficiencies. Methods of making and methods of use are further provided. In one or more aspects, an anodically-coloring electrochromic molecule is provided having a structure according to Formula I, wherein X is S, O, Se, or $NR^{17}$, wherein $R^{17}$ is selected from the group consisting of hydrogen, substituted and unsubstituted alkyl, and substituted and unsubstituted heteroalkyl; wherein $R^{11}$ and $R^{12}$ are each independently selected from the group consisting of hydrogen, hydroxyl, halogen, nitro, substituted and unsubstituted alkyl, substituted and unsubstituted heteroalkyl, substituted and unsubstituted alkylthio, substituted and unsubstituted alkenyl, substituted and unsubstituted alkynyl, substituted and unsubstituted alkoxy, substituted and unsubstituted amine, substituted and unsubstituted amido, and substituted and unsubstituted carbonyl; wherein $R^{13}$ is selected from the group consisting of a bond, hydrogen, an electron donating substituent, and an electron withdrawing substituent; or wherein $R^{13}$ is as defined above and $R^{11}$ and $R^{12}$, when taken together with the atoms to which they are attached, form a substituted or unsubstituted C2-C40 cycloalkyl, heterocycloalkyl, cycloalkenyl, heterocycloalkenyl, aryl, or heteroaryl ring; or wherein $R^{11}$ is as defined above and $R^{12}$ and $R^{13}$, when taken together with the atoms to which they are attached, form a substituted or unsubstituted C4-C40 cycloalkyl, heterocycloalkyl, cycloalkenyl, heterocycloalkenyl, aryl, or heteroaryl group; and wherein $R^{14}$, $R^{15}$, $R^{14'}$, $R^{15'}$, and $R^{16}$ are each independently selected from the group consisting of a bond, hydrogen, electron donating substituents, and electron withdrawing substituents; or wherein when one of more of $R^{14}$ and $R^{15}$, $R^{14'}$ and $R^{15'}$, $R^{15}$ and $R^{16}$, and $R^{15'}$ and $R^{16}$ are taken together with the atoms to which they are attached, they form a substituted or unsubstituted C5-C50 aryl or heteroaryl ring and the remaining $R^{14}$, $R^{15}$, $R^{14'}$, $R^{15'}$, and $R^{16}$ are as defined above.

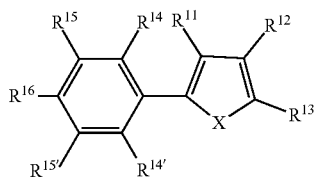

Formula I

In some aspects, an anodically-coloring electrochromic molecule is provided having a structure according to any one of Formula Ia, Formula Ib, Formula Ic, and Formula Id, wherein each occurrence of X is independently S, O, Se, or $NR^{17}$, wherein $R^{17}$ is selected from the group consisting of hydrogen, substituted and unsubstituted alkyl, and substituted and unsubstituted heteroalkyl; wherein each occurrence of $R^{11}$ and $R^{12}$ is independently selected from the group consisting of hydrogen, hydroxyl, halogen, nitro, substituted and unsubstituted alkyl, substituted and unsubstituted heteroalkyl, substituted and unsubstituted alkylthio, substituted and unsubstituted alkenyl, substituted and unsubstituted alkynyl, substituted and unsubstituted alkoxy, substituted and unsubstituted amine, substituted and unsubstituted amido, and substituted and unsubstituted carbonyl; or wherein $R^{11}$ and $R^{12}$, when taken together with the atoms to which they are attached, form a substituted or unsubstituted C2-C40 cycloalkyl, heterocycloalkyl, cycloalkenyl, heterocycloalkenyl, aryl, or heteroaryl ring; wherein each occurrence of $R^{14}$, $R^{15}$, $R^{14'}$, $R^{15'}$, and $R^{16}$ is independently selected from the group consisting of hydrogen, electron donating substituents, and electron withdrawing substituents; wherein each occurrence of Y is independently none, O, Se, S, $NR^{19}$, or $R^{20}$; wherein $R^{19}$ is hydrogen or a substituted or unsubstituted C1-C23 alkyl or heteroalkyl; wherein $R^{20}$ is a C1-C12 alkyl or heteroalkyl diradical; and wherein n is an integer between 1 and 1000.

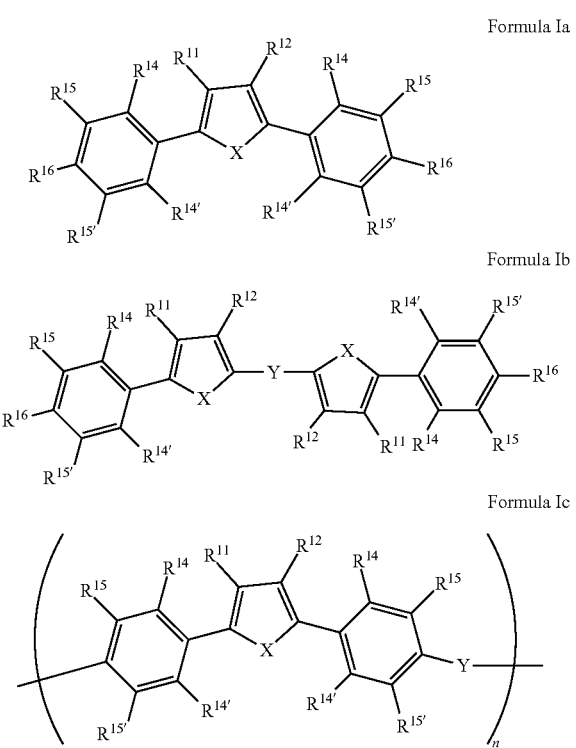

Formula Ia

Formula Ib

Formula Ic

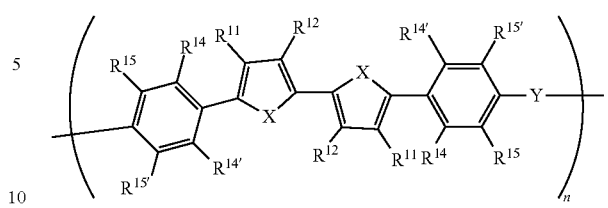

Formula Id

In some aspects, an electrochromic device is provided having (a) a first electrode; (b) a second electrode; (c) an electrolyte sandwiched between the first electrode and the second electrode; and (d) an anodically-coloring electrochromic molecule described herein. The anodically-coloring electrochromic molecule can be dispersed in the electrolyte and/or can be covalently attached to a surface of one of the electrodes. Suitable electrodes can include, but are not limited to, a transparent conducting oxide coated glass electrode, a conductive polymer coated glass electrode, a metal grid on glass electrode, a carbon nanotube on glass electrode, a metal film on glass electrode, and a combination thereof.

Other systems, methods, features, and advantages of anodically coloring molecules, electrochromic devices thereof, and methods of making and uses thereof will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 5A is a side schematic view of the OTTLE. FIG. 5B is a front schematic view of the OTTLE. FIG. 5C demonstrates the coloring at applied voltage showing the cropping used for imaging the device.

FIG. 6A is a graph of the cyclic voltammograms of a solution containing 250 μM of the respective ACE molecule in 0.5M TBAPF$_6$/DCM solution. FIG. 6B is a graph of the differential pulse Itammograms of a solution containing 250 μM of the respective ACE molecule in 0.5M TBAPF$_6$/DCM solution. FIG. 6C is a graph of a cyclic voltammogram for 10 CV cycles of ACE4 with a range of 0-1.2 V showing the formation of a new species after the first cycle.

DETAILED DESCRIPTION

Figure 1:
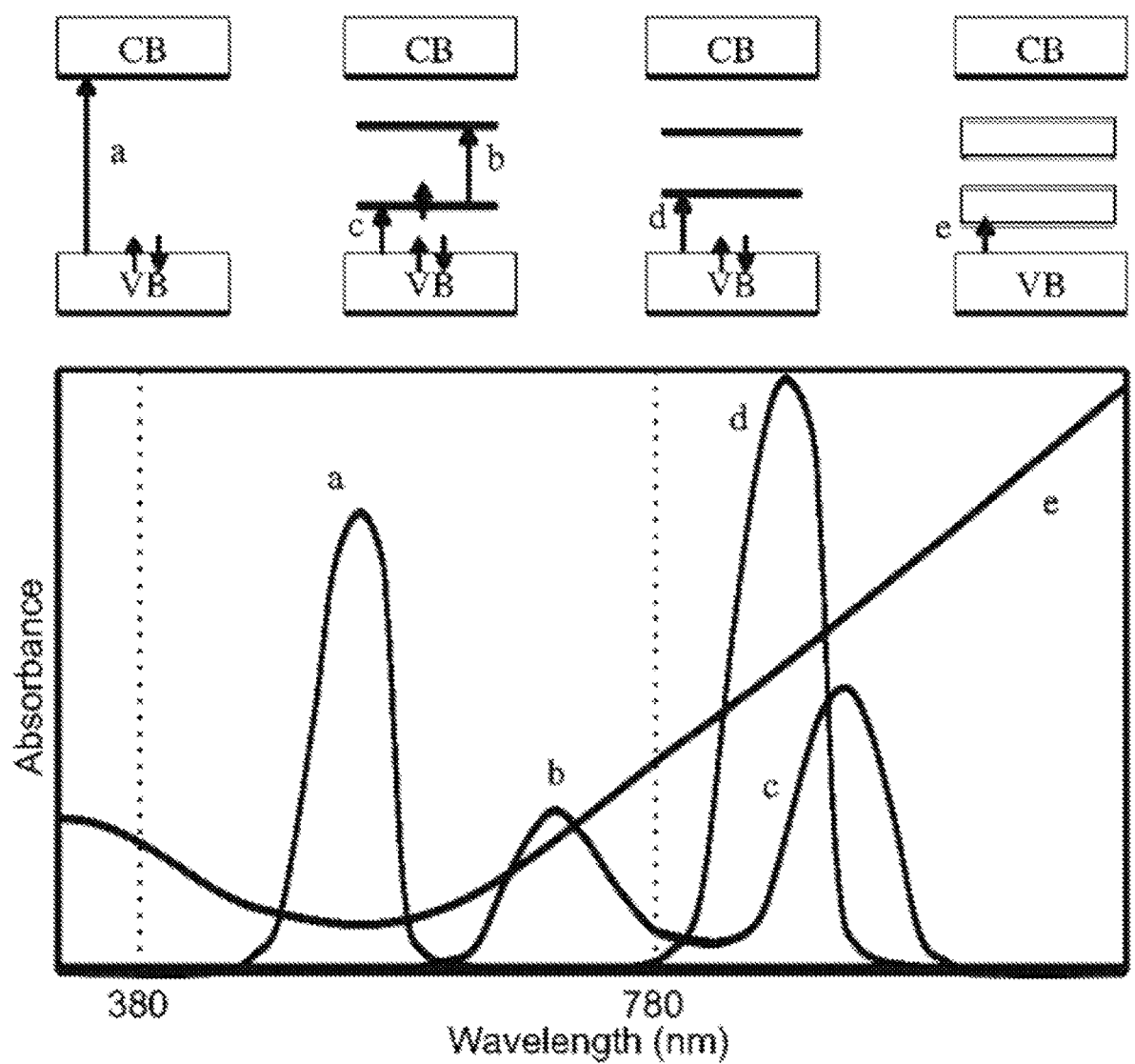
FIG. 1 is a schematic diagram depicting the electronic structures of allowed transitions in conjugated electrochromic polymer chains as a function of oxidation state: (a) a neutral polymer, (b and c) a polymer carrying a polaron, (d) a polymer carrying a bipolaron, (e) a polymer or assembly of polymer chains with a high concentration of polarons and bipolarons (intrachain or interchain polaron network), a chain or assembly of chains with a high concentration of bipolarons (intrachain or interchain bipolaron bands) with a representation for absorbance spectra of these transitions illustrated at the bottom.
Figure 2:
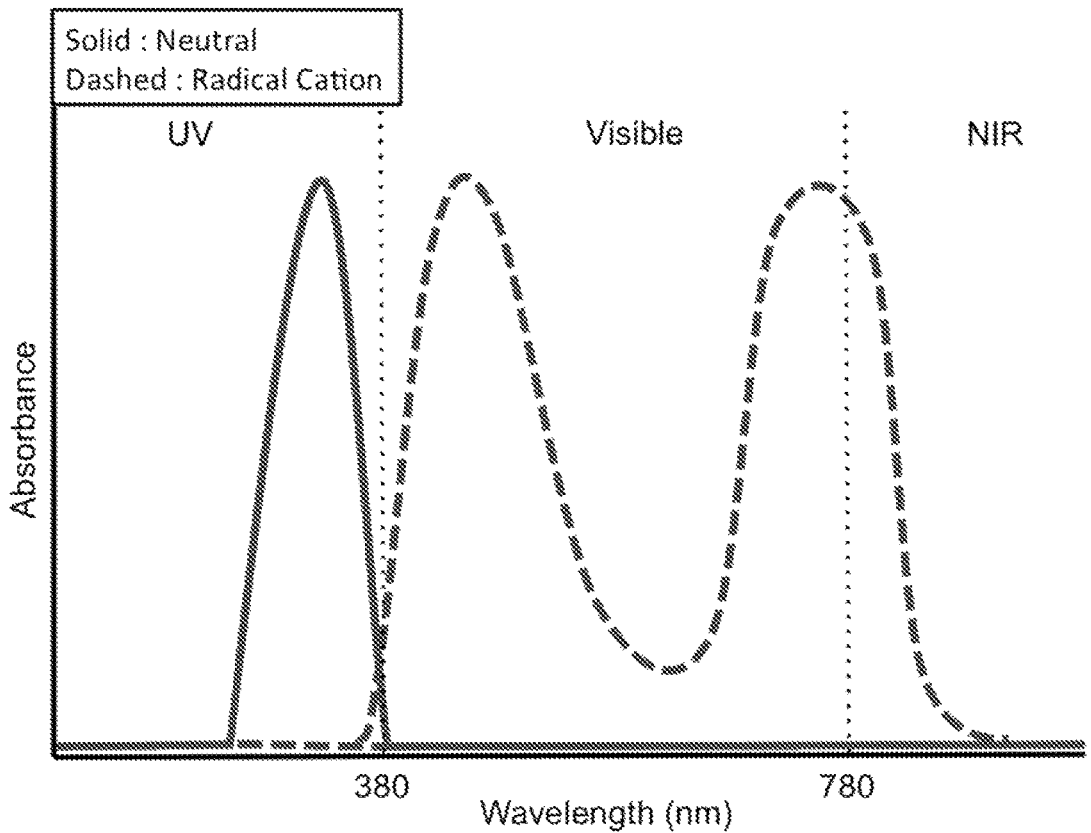
FIG. 2 is a theoretical spectra for an ideal anodically coloring material with a UV absorbing neutral state and broadly absorbing radical cation state.

In various aspects, anodically coloring electrochromic molecules are provided that overcome one or more of the aforementioned deficiencies. Electrochromic devices and methods of making and use thereof are also provided. In various aspects, this disclosure provides anodically coloring electrochromic molecules and methods of making and uses thereof as a solution to avoid the NIR tailing observed in cathodically coloring ECPs. As demonstrated in FIG. 2, anodically coloring materials are designed to have electron rich, conjugated chromophores of discrete length, which have wide optical gaps absorbing specifically in the UV in their neutral state with minimal tailing into the visible in the colorless state. This can be seen by the solid curve in FIG. 2. Upon oxidation to the radical cation state, short conjugation lengths maintain a high-energy absorption relative to fully conjugated polymer systems, moving the absorbance into the visible region (e.g. ~380-780 nm). This broad dual band absorbance is denoted by the dashed curve. In order to design these materials as effective high contrast electrochromes, a fundamental understanding is provided herein on how conjugation length, electron-rich character, and steric strain control the redox potential for switching to, and the absorption characteristics of, the radical cation state.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant specification should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to about 5%" should be interpreted to include not only the explicitly recited values of about 0.1% to about 5%, but also include individual values (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'", where 'x' and 'y' are numerical values, includes "about 'x' to about 'y'".

In some instances, units may be used herein that are non-metric or non-SI units. Such units may be, for instance, in U.S. Customary Measures, e.g., as set forth by the National Institute of Standards and Technology, Department of Commerce, United States of America in publications such as NIST HB 44, NIST HB 133, NIST SP 811, NIST SP 1038, NBS Miscellaneous Publication 214, and the like. The units in U.S. Customary Measures are understood to include equivalent dimensions in metric and other units (e.g., a dimension disclosed as "1 inch" is intended to mean an equivalent dimension of "2.5 cm"; a unit disclosed as "1 pcf" is intended to mean an equivalent dimension of 0.157 kN/m$^3$; or a unit disclosed 100° F. is intended to mean an equivalent dimension of 37.8° C.; and the like) as understood by a person of ordinary skill in the art.

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The term "small molecule", as used herein, generally refers to an organic molecule that is less than 2000 g/mol in molecular weight, less than 1500 g/mol, less than 1000 g/mol, less than 800 g/mol, or less than 500 g/mol. Small molecules are non-polymeric and/or non-oligomeric.

The term "copolymer" as used herein, generally refers to a single polymeric material that is comprised of two or more different monomers. The copolymer can be of any form, such as random, block, graft, etc. The copolymers can have any end-group, including capped or acid end groups. Copolymers can alternating copolymers (having regularly alternating monomer units, e.g. A-B-A-B-A-B), periodic copolymers (having a regularly repeating sequence of monomer units, e.g. A-B-B-A-B-B-A-B-B), statistical copolymers (the order of monomers follows a nearly statistical distribution), a block copolymer (having blocks of a first monomer attached to blocks of a second monomer unit), or a combination thereof. Copolymers can include linear or branched copolymers.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions. Unless otherwise specified, the molecular weight of a polymer can be the number average molecular weight ($M_n$) or the weight average molecular weight ($M_w$).

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In some embodiments, a straight chain or branched chain alkyl has 30 or fewer carbon atoms in its backbone (e.g., $C_1$-$C_{30}$ for straight chains, $C_3$-$C_{30}$ for branched chains), 20 or fewer, 12 or fewer, or 7 or fewer. Likewise, in some embodiments cycloalkyls have from 3-10 carbon atoms in their ring structure, e.g. have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a hosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, or from one to six carbon atoms in its backbone structure. Likewise, "lower alkenyl" and "lower alkynyl" have similar chain lengths. Throughout the application, preferred alkyl groups are lower alkyls. In some embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In some embodiments, the "alkylthio" moiety is represented by one of —S-alkyl, —S-alkenyl, and —S-alkynyl. Representative alkylthio groups include methylthio, and ethylthio. The term "alkylthio" also encompasses cycloalkyl groups, alkene and cycloalkene groups, and alkyne groups. "Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, and tert-butoxy. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The terms "amine" and "amino" are art-recognized and refer to both unsubstituted and substituted amines, e.g., a moiety that can be represented by the general formula:

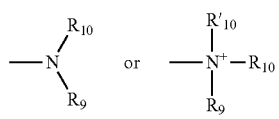

wherein R9, R10, and R'10 each independently represent a hydrogen, an alkyl, an alkenyl, —(CH2)m-R8 or R9 and R10 taken together with the N atom to which they are attached complete a heterocycle having from 4 to 8 atoms in the ring structure; R8 represents an aryl, a cycloalkyl, a cycloalkenyl, a heterocycle or a polycycle; and m is zero or an integer in the range of 1 to 8. In some embodiments, only one of R9 or R10 can be a carbonyl, e.g., R9, R10 and the nitrogen together do not form an imide. In still other embodiments, the term "amine" does not encompass amides, e.g., wherein one of R9 and R10 represents a carbonyl. In additional embodiments, R9 and R10 (and optionally R'10) each independently represent a hydrogen, an alkyl or cycloakly, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R9 and R10 is an alkyl group.

The term "amido" is art-recognized as an amino-substituted carbonyl and includes a moiety that can be represented by the general formula:

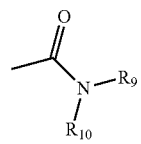

wherein R9 and R10 are as defined above.

"Aryl", as used herein, refers to $C_5$-$C_{10}$-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl,oxadiazolyl,1,2,3-oxadiazolyl,1,2, 4-oxadiazolyl,1,2,5-oxadiazolyl,1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

The term "aralkyl", as used herein, refers to an alkyl group substituted with an aryl group (e.g., an aromatic or heteroaromatic group).

The term "carbocycle", as used herein, refers to an aromatic or non-aromatic ring in which each atom of the ring is carbon.

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, and —CN.

The term "carbonyl" is art-recognized and includes such moieties as can be represented by the general formula:

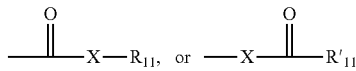

wherein X is a bond or represents an oxygen or a sulfur, and $R_{11}$ represents a hydrogen, an alkyl, a cycloalkyl, an alkenyl, an cycloalkenyl, or an alkynyl, $R'_{11}$ represents a hydrogen, an alkyl, a cycloalkyl, an alkenyl, an cycloalkenyl, or an alkynyl. Where X is an oxygen and $R_{11}$ or $R'_{11}$ is not hydrogen, the formula represents an "ester". Where X is an oxygen and $R_{11}$ is as defined above, the moiety is referred to herein as a carboxyl group, and particularly when $R_{11}$ is a hydrogen, the formula represents a "carboxylic acid". Where X is an oxygen and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R'_{11}$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "heteroatom" as used herein means an atom of any element other than carbon or hydrogen. Examples of heteroatoms are boron, nitrogen, oxygen, phosphorus, sulfur and selenium. Other heteroatoms include silicon and arsenic.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, C3-C20 cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. The heteroatoms such as nitrogen may have hydrogen substituents and/or any permissible substituents of organic compounds described herein which satisfy the valences of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

Anodically-Coloring Molecules

In various aspects, anodically-coloring electrochromic molecules are provided. The anodically-coloring electrochromic molecules overcome many of the aforementioned deficiencies, for example the deficiencies of the transmissive grey-blue hue in cathodically-coloring molecules and devices.

In some aspects, anodically-coloring electrochromic molecules are provided having a structure according to Formula I

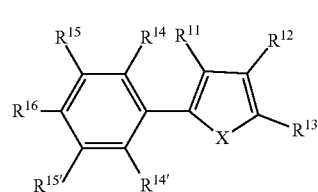

Formula I wherein X is S, O, Se, or $NR^{17}$, wherein $R^{17}$ is selected from the group consisting of hydrogen, substituted and unsubstituted alkyl, and substituted and unsubstituted heteroalkyl; wherein $R^{11}$ and $R^{12}$ are each independently selected from the group consisting of hydrogen, hydroxyl, halogen, nitro, substituted and unsubstituted alkyl, substituted and unsubstituted heteroalkyl, substituted and unsubstituted alkylthio, substituted and unsubstituted alkenyl, substituted and unsubstituted alkynyl, substituted and unsubstituted alkoxy, substituted and unsubstituted amine, substituted and unsubstituted amido, and substituted and unsubstituted carbonyl; wherein $R^{13}$ is selected from the group consisting of a bond, hydrogen, an electron donating substituent, and an electron withdrawing substituent; or wherein $R^{13}$ is as defined above and $R^{11}$ and $R^{12}$, when taken together with the atoms to which they are attached, form a substituted or unsubstituted C2-C40 cycloalkyl, heterocycloalkyl, cycloalkenyl, heterocycloalkenyl, aryl, or heteroaryl ring; or wherein $R^{11}$ is as defined above and $R^{12}$ and $R^{13}$, when taken together with the atoms to which they are attached, form a substituted or unsubstituted C4-C40 cycloalkyl, heterocycloalkyl, cycloalkenyl, heterocycloalkenyl, aryl, or heteroaryl group; and wherein $R^{14}$, $R^{15}$, $R^{14'}$, $R^{15'}$, and $R^{16}$ are each independently selected from the group consisting of a bond, hydrogen, electron donating substituents, and electron withdrawing substituents; or wherein when one of more of $R^{14}$ and $R^{15}$, $R^{14'}$ and $R^{15'}$, $R^{15}$ and $R^{16}$, and $R^{15'}$ and $R^{16}$ are taken together with the atoms to which they are attached, they form a substituted or unsubstituted C5-C50 aryl or heteroaryl ring and the remaining $R^{14}$, $R^{15}$, $R^{14'}$, $R^{15'}$, and $R^{16}$ are as defined above.

In some aspects, the anodically-coloring electrochromic molecules have a structure according to Formula I, where X, $R^{13}$, $R^{14}$, $R^{15}$, $R^{14'}$, $R^{15'}$, and $R^{16}$ are as defined elsewhere herein; and wherein $R^{11}$ and $R^{12}$, when taken together with the atoms to which they are attached, form a substituted or unsubstituted C2-C40, C2-C20, C4-C20, C4-C12, C2-C6, or C6-C12 cycloalkyl, heterocycloalkyl, cycloalkenyl, heterocycloalkenyl, aryl, or heteroaryl ring. In some aspects, the cycloalkyl, heterocycloalkyl, cycloalkenyl, heterocycloalkenyl, aryl, or heteroaryl ring is substituted with one or more C1-C4 linear or branched alkyl substituents. In some aspects, $R^{11}$ and $R^{12}$, when taken together, have a structure according to the formula —$X^{18}$—$R^{18}$—$X^{18}$—; where each occurrence of $X^{18}$ is independently selected from the group consisting of O, $NR^{17}$, S, and Se; and where $R^{18}$ is a substituted or unsubstituted alkyl diradical having 1 to 12, 1 to 6, 4 to 12, or 6 to 12 carbon atoms. In some aspects, $R^{18}$ is a 2,2-substituted propylene diradical or a 1,3-substituted propylene diradical.

In some aspects, the anodically-coloring electrochromic molecule is a small molecule having a structure according to Formula Ia or Formula Ib.

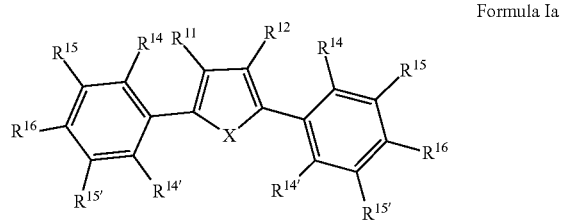

Formula Ia

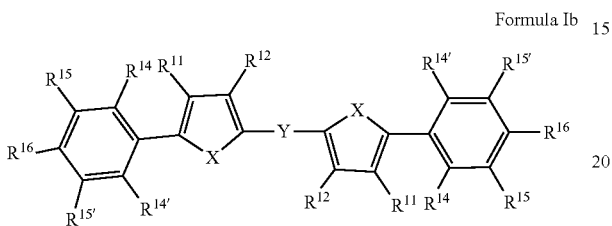

Formula Ib

In some aspects, the anodically-coloring electrochromic molecule is a small molecule oligomer, or polymer having a structure according to Formula Ic or Formula Id.

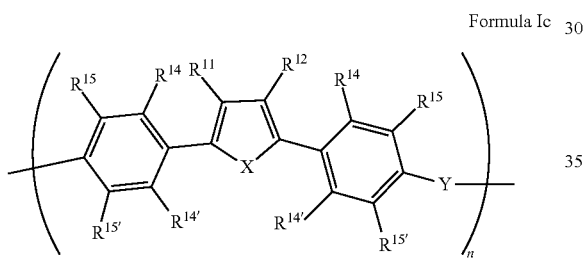

Formula Ic

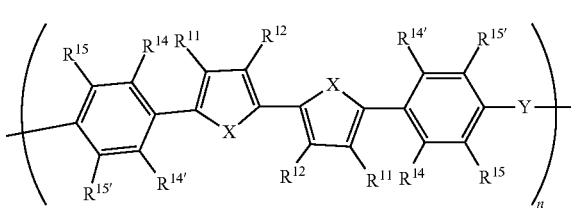

Formula Id

In Formula Ia, Formula Ib, Formula Ic, and Formula Id, X, $R^{11}$, $R^{12}$, $R^{13}$, $R^{14}$, $R^{15}$, $R^{14'}$, $R^{15'}$, and $R^{16}$ are as defined elsewhere herein; wherein each occurrence of Y is independently none, O, Se, S, $NR^{19}$, or $R^{20}$; wherein $R^{19}$ is hydrogen or a substituted or unsubstituted C1-C30, C1-C23, C1-C4, C1-C12, C4-C12, or C12-C23 alkyl or heteroalkyl; wherein $R^{20}$ is a C1-C18, C1-C12, C1-C4, or C4-C12 alkyl or heteroalkyl diradical; and where n is an integer from 1 to 1000, 1 to 5, 1 to 12, 1 to 20, 20 to 1000, 20 to 500, or 20 to 200.

In some aspects, the anodically-coloring electrochromic molecule has a structure according to Formula I, Formula Ia, Formula Ib, Formula Ic, or Formula Id, wherein $R^{11}$ and $R^{12}$ are each independently selected from the group consisting of hydrogen and substituted and unsubstituted alkyl, heteroalkyl, and alkoxy groups having 1 to 20, 1 to 4, 4 to 12, or 1 to 12 carbon atoms; or when taken together with the atoms to which they are attached, $R^{11}$ and $R^{12}$ form a substituted or unsubstituted cycloalkyl or heterocycloalkyl having 1 to 20, 4 to 20, 4 to 12, 1 to 12, or 12 to 18 carbon atoms.

In some aspects, an anodically-coloring electrochromic molecule is provided having a structure Ar-Het, where Het is selected from the group consisting of Formula IIa, Formula IIb, and Formula IIc; and wherein Ar is selected from the group consisting of Formula IIIa, Formula IIIb, Formula IIIc, Formula IIId, Formula IIIe, Formula IIIf, and Formula IIIg.

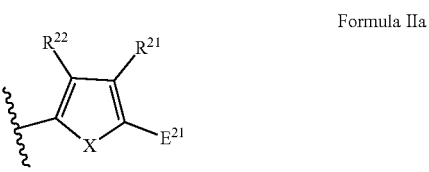

Formula IIa

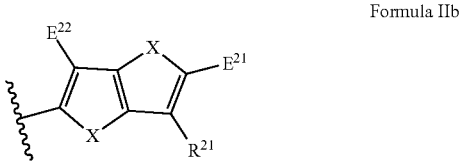

Formula IIb

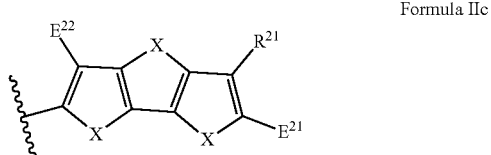

Formula IIc

In some aspects, each occurrence of $R^{21}$ and $R^{22}$ is independently selected from the group consisting of hydrogen, hydroxyl, halogen, nitro, substituted and unsubstituted alkyl, substituted and unsubstituted heteroalkyl, substituted and unsubstituted alkylthio, substituted and unsubstituted alkenyl, substituted and unsubstituted alkynyl, substituted and unsubstituted alkoxy, substituted and unsubstituted amine, substituted and unsubstituted amido, and substituted and unsubstituted carbonyl, or wherein $R^{21}$ and $R^{22}$, when attached to adjacent atoms and taken together with the atoms to which they are attached, form a substituted or unsubstituted C2-C40, C2-C20, C4-C20, C4-C12, C2-C6, or C6-C12 cycloalkyl, heterocycloalkyl, cycloalkenyl, heterocycloalkenyl, aryl, or heteroaryl ring.

In some aspects, each occurrence of $E^{21}$ and $E^{22}$ is independently selected from the group consisting of a bond, hydrogen, —Ar, —Y-Het-Ar, electron donating substituents, and electron withdrawing substituents, where AR, Y, and Het are as described elsewhere herein.

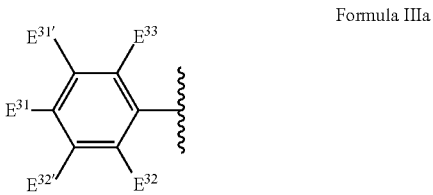

Formula IIIa

Formula IIIb
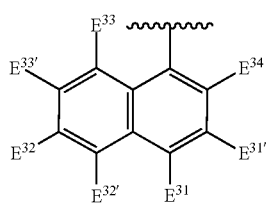

Formula IIIc
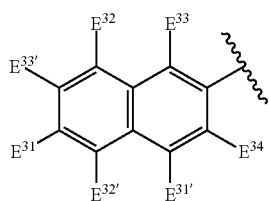

Formula IIId
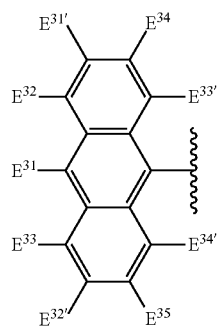

Formula IIIe
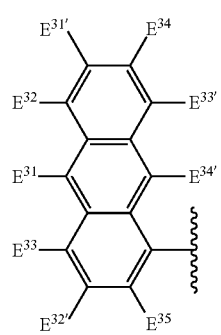

Formula IIIf
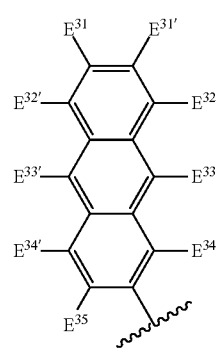

Formula IIIg
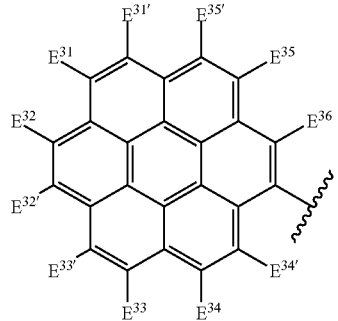

In some aspects, each occurrence of $E^{31}$, $E^{32}$, $E^{33}$, $E^{34}$, $E^{35}$, and $E^{36}$ is independently selected from the group consisting of a bond, hydrogen, electron donating substituents, and electron withdrawing substituents; and each occurrence of $E^{31'}$, $E^{32'}$, $E^{33'}$, $E^{34'}$, and $E^{35'}$ is independently selected from the group consisting of a bond, hydrogen, electron donating substituents, and electron withdrawing substituents. In some aspects, each occurrence of $E^{31}$, $E^{32}$, $E^{33}$, $E^{34}$, $E^{35}$, and $E^{36}$ is independently selected from the group consisting of a hydrogen and electron donating substituents. In some aspects, each occurrence of $E^{31'}$, $E^{32'}$, $E^{33'}$, $E^{34'}$, and $E^{35'}$ is independently selected from the group consisting of hydrogen, electron donating substituents, and electron withdrawing substituents.

In some aspects, the anodically-coloring electrochromic material has a structure according to the following formula

wherein Y is as described elsewhere herein, or where Y is selected from the group consisting of none, O, and S; and where n is an integer from 1 to 1000, 1 to 5, 1 to 12, 1 to 20, 20 to 1000, 20 to 500, or 20 to 200.

In some aspects, each of the electron donating substituents is independently selected from the group consisting of —$NH_2$, —$NHR^1$, —$NR(R^2)$, —OH, —$OR^1$, —$SR^1$, —$SeR^1$, —$CH_2R^1$, —$Ar^2R^1$, $S(O)R^1$, —$S(O)_2R^1$, —$NHNH_2$, and —$N(R)NH_2$, wherein $Ar^2$ is an aryl or substituted aryl; and wherein each occurrence of $R^1$, $R^2$ and $R^3$ is independently selected from the group consisting of hydrogen, linear or branched lower alkyl, linear or branched lower alkenyl, linear or branched lower alkynl, linear or branched aryl lower alkyl, aryl, linear or branched heterocyclic lower alkyl, linear or branched heterocyclic lower cycloalkyl, linear or branched lower cycloalkyl, linear or branched lower cycloalkyl lower alkyl and mixtures or combinations thereof. For example, in some aspects, each occurrence of $R^1$, $R^2$ and $R^3$ is independently selected from the group consisting of hydrogen, methyl, ethyl, propyl, isopropyl, butyl, sec-butyl, isobutyl, and tert-butyl. Ar2 can, at least in some aspects, be a substituted or unsubstituted phenyl.

In some aspects, the electron withdrawing substituents is independently selected from the group consisting of a —Cl, —F, —Br, —C(O)H, —C(O)$R^4$, —C(O)O$R^4$, —C(O)OH, —CN, —$NO_2$, —C(O)$NH_2$, —C(O)NH$R^4$, —C(O)N($R^4$) $R^5$, —$R^6$, —O$R^6$, —$SO_3H$, —$SO_3R^4$, —OC(O)$R^4$, wherein each occurrence of $R^4$ and $R^5$ is independently selected from the group consisting of hydrogen, linear or branched lower alkyl, linear or branched perfluorinated lower alkyl, linear or branched partially-fluorinated lower alkyl, linear or branched perfluorinated aryl lower alkyl, linear or branched partially-fluorinated aryl lower alkyl, aryl, perfluorinated aryl, partially-fluorinated aryl, and a combination thereof; and wherein each occurrence of $R^6$ is independently selected from the group consisting of linear or branched perfluorinated lower alkyl, linear or branched partially-fluorinated lower alkyl, linear or branched perfluorinated aryl lower alkyl, linear or branched partially-fluorinated aryl lower alkyl, perfluorianted aryl, partially-fluorinated aryl, and a combination thereof.

In some aspects, each occurrence of $R^4$ and $R^5$ is independently selected from the group consisting of hydrogen methyl, ethyl, propyl, isopropyl, butyl, sec-butyl, isobutyl, tert-butyl, and partially-fluorinated and perflourinated derivatives thereof; and wherein $R^6$ is selected from the group consisting of partially-fluorinated and perflourinated derivatives of methyl, ethyl, propyl, isopropyl, butyl, sec-butyl, isobutyl, and tert-butyl.

Electrochromic Devices

Electrochromic devices are well known, e.g., US Patent Application Publication No. 2017/0267811 A1, U.S. Pat. No. 6,791,738, International PCT Publication No. WO 2013/003548 A3, U.S. Pat. Nos. 4,902,108 and 6,178,034, incorporated herein in their entirety by reference. Such devices undergo a change in electromagnetic radiation transmission upon application of an electrical stimulus and have found use in a number of commercial applications. An electrochromic device (ECD) controls optical properties such as optical transmission, absorption, reflectance and/or emittance in a continual but reversible manner on application of voltage (electrochromism). This property enables an ECD to be used for applications like smart glass, electrochromic mirrors, and electrochromic display devices. For example, they may be employed in glazings, e.g., energy efficient and privacy windows for architectural or automotive use, automotive rearview mirrors, displays, filters, eyewear including goggles, antidazzle and fog penetrating devices, electrochromic displays, and other applications where variable light transmission is desired.

The electrochromic devices will generally include a first electrode and a second electrode. When the electrochromic device will operate in transmission mode, both the first electrode and the second electrode will typically be transparent electrodes. Numerous transparent electrodes have been developed in the literature. In particular, transparent electrodes can include transparent conducting oxide coated glass electrodes or conductive polymer coated glass electrodes. Thin films of certain coinage metals can be deposited, for instance, on glass to create transparent conducting electrodes. In some aspects, the transparent electrode is a doped semiconductor oxide on glass electrode. In some aspects, the electrode can include a metal grid on glass electrode, a carbon nanotube on glass electrode, a metal film on glass electrode, and a combination thereof. In some aspects, when the electrochromic device is to be operated in a reflectance mode, one of the electrodes will be or will include a reflective layer, e.g. with coated or replaced with a reflective surface like aluminum, gold or silver, which controls the reflective light intensity. In some aspects, one or both of the first electrode and the second electrode are selected from the group consisting of a graphene electrode, an indium-tin-oxide electrode, a PEDOT:PSS electrode, and a combination thereof.

In general, for the electrochromic devices to work with the anodically-coloring electrochromic molecules described herein, the electrochromic device will generally include a redox couple that is reduced as the anodically-coloring electrochromic molecule is oxidized from the neutral state to the cation state. Conversely, the redox couple will be oxidized as the anodically-coloring electrochromic molecule is reduced from the cation state back to the neutral state. In some aspects, the second electrode includes a cathodically coloring electrochromic molecule that is capable of being reduced when a voltage is applied, an optically inactive molecule that is capable of being reduced when a voltage is applied, or a combination thereof.

The electrochromic device will generally include some means for conducting ions between the anodically-coloring electrochromic molecule and the redox couple, e.g. between the two elefctrodes or between the anodically-coloring electrode and an ion reservoir (ion storage) material. The electrolyte separates both cathodes and anodes to avoid direct electrical contact, but permits mutual ionic exchanges. The electrolyte can include a liquid electrolyte, a polymer electrolyte, a gel electrolyte, an organic electrolyte, an aqueous electrolyte, a biological electrolyte, a solid state electrolyte, or a combination thereof. Suitable electrolytes can include, for instance, sodium chloride, potassium chloride, tetrabutylammonium hexafluorophosphate (TBAPF6), and lithium bis(trifluoromethylsulfonyl)imide (LiBTI).

In some aspects, an electrochromic device is provided having (a) a first electrode; (b) a second electrode; (c) an electrolyte sandwiched between the first electrode and the second electrode; and (d) an anodically-coloring electrochromic molecule having a structure according to Formula I, where X, $R^{11}$, $R^{12}$, $R^{13}$, $R^{14}$, $R^{15}$, $R^{14'}$, $R^{15'}$, and $R^{16}$ are as described above.

In some aspects, an electrochromic device is provided having (a) a first electrode; (b) a second electrode; (c) an electrolyte sandwiched between the first electrode and the second electrode; and (d) an anodically-coloring electrochromic molecule having a structure having a structure Ar-Het, where Ar and Het are as described above.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1: Anodically Coloring Electrochromic Molecules Based on 2-thiomethyl-dioxythiophene Coupled to a 4-methoxyphenylene This example demonstrate the design and performance of exemplary anodically coloring electrochromic molecules based on 2-thiomethyl-dioxythiophene coupled to a 4-methoxyphenylene. The molecules exhibit a practical combination of low-voltage redox switching and high optical contrast. The examples demonstrate how tuning the molecular structures of the chromophores can be used altered to redistribute the electron density in the frontier molecular orbitals providing control over the energy of the optical transitions and ultimately tune set the color of the low energy radical cation peak by shifting the λmax of the low energy radical cation peak with a range of over 400 nm. The neutral, colorless state of these molecules are UV absorbing providing materials that have no color with L*a*b* values of 100,0,0. These molecules are oxidized to vibrantly colored radical cations that span the visible spectrum creating green, yellow, and red chromophores. These molecules are then mixed to create transmissive, colorless blends that switch to opaque black solutions.

Figure 3:
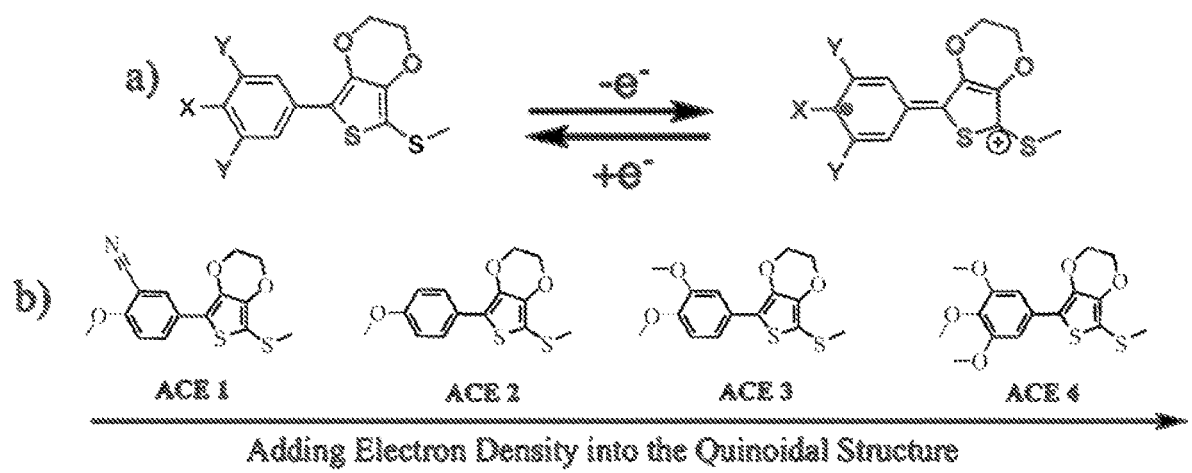
FIG. 3 is a schematic demonstrating how removing an electron to form the radical cation changes conjugation from the para to the meta position, thus moving the controlling position between the neutral and charged state (a) along with the structures of exemplary anodically coloring electrochromic molecules in order of increasing SOMO energy based on the electron donating character of the moieties in the meta position (b).
Figure 4A:
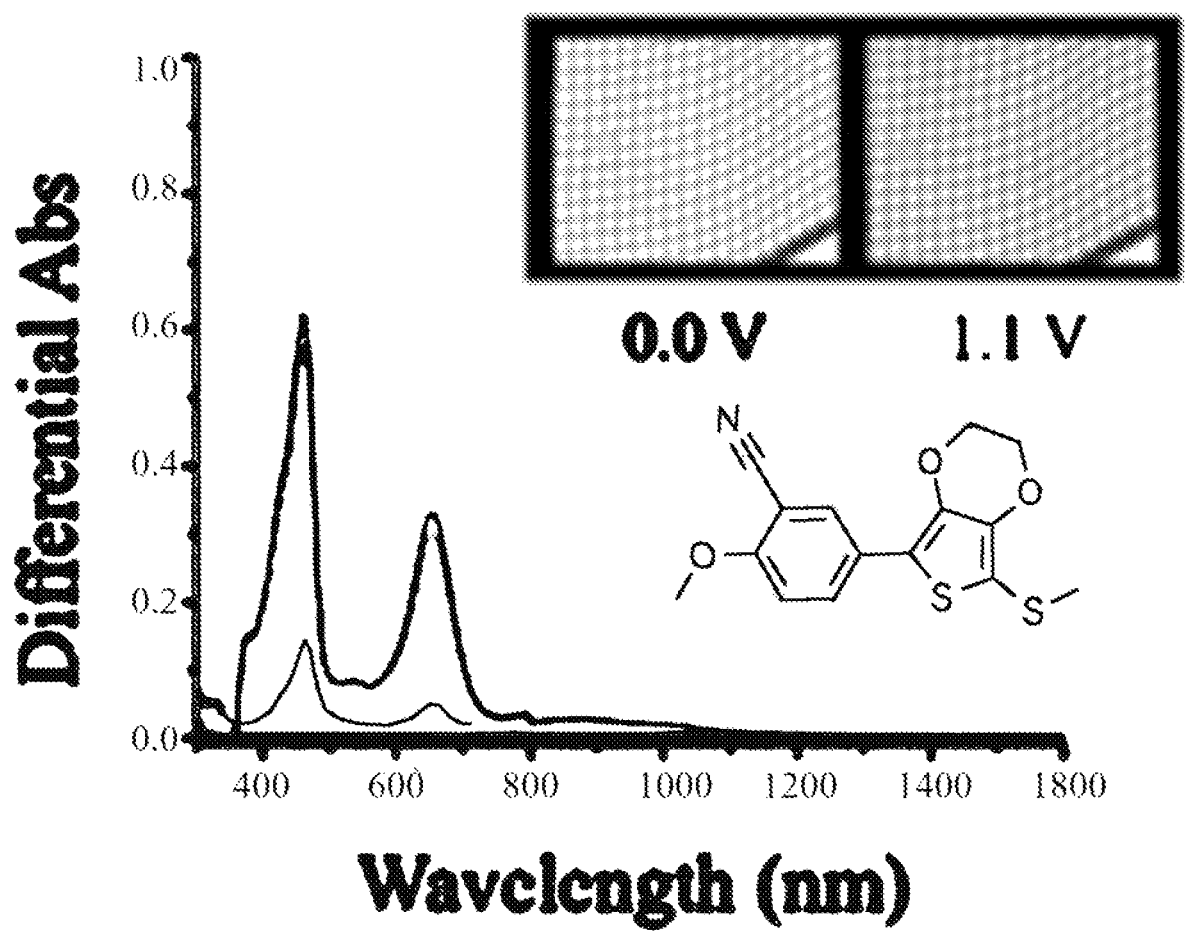
FIGS. 4A-4D are differential spectroelectrochemistry performed with an optically transparent thin layer electrode (OTTLE) with photographs in the insets at the extreme potentials as noted for ACE1 (FIG. 4A), ACE2 (FIG. 4B), ACE3 (FIG. 4C), and ACE4 (FIG. 4D).
Figure 4B:
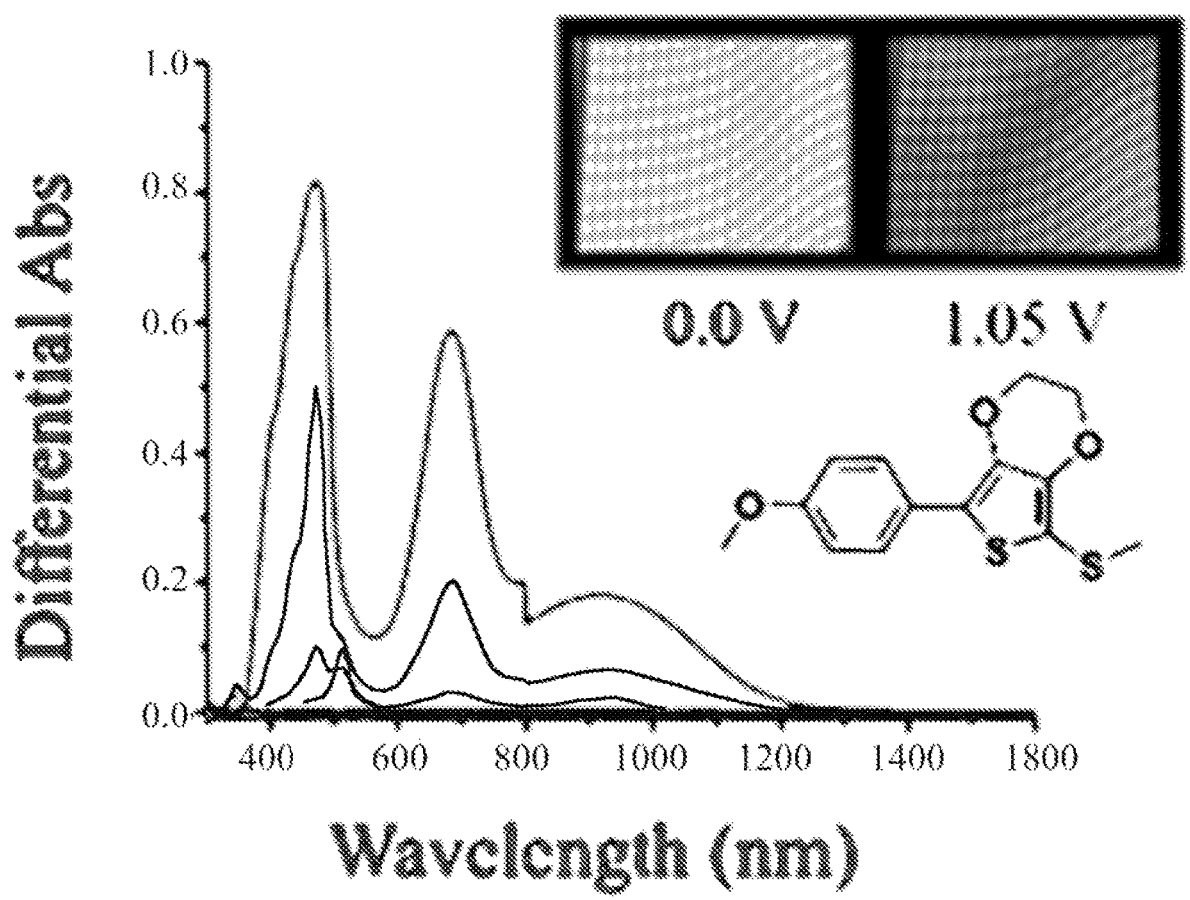
Figure 4C:
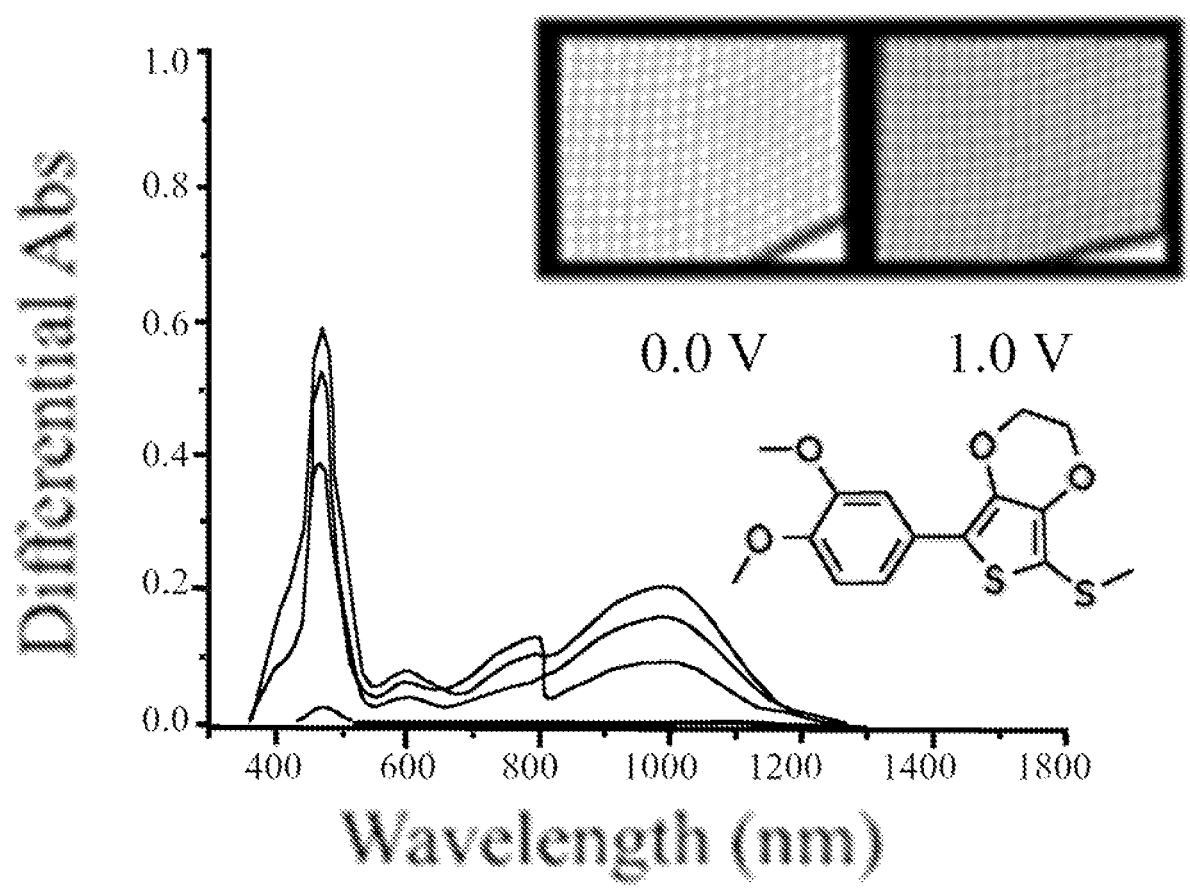
Figure 4D:
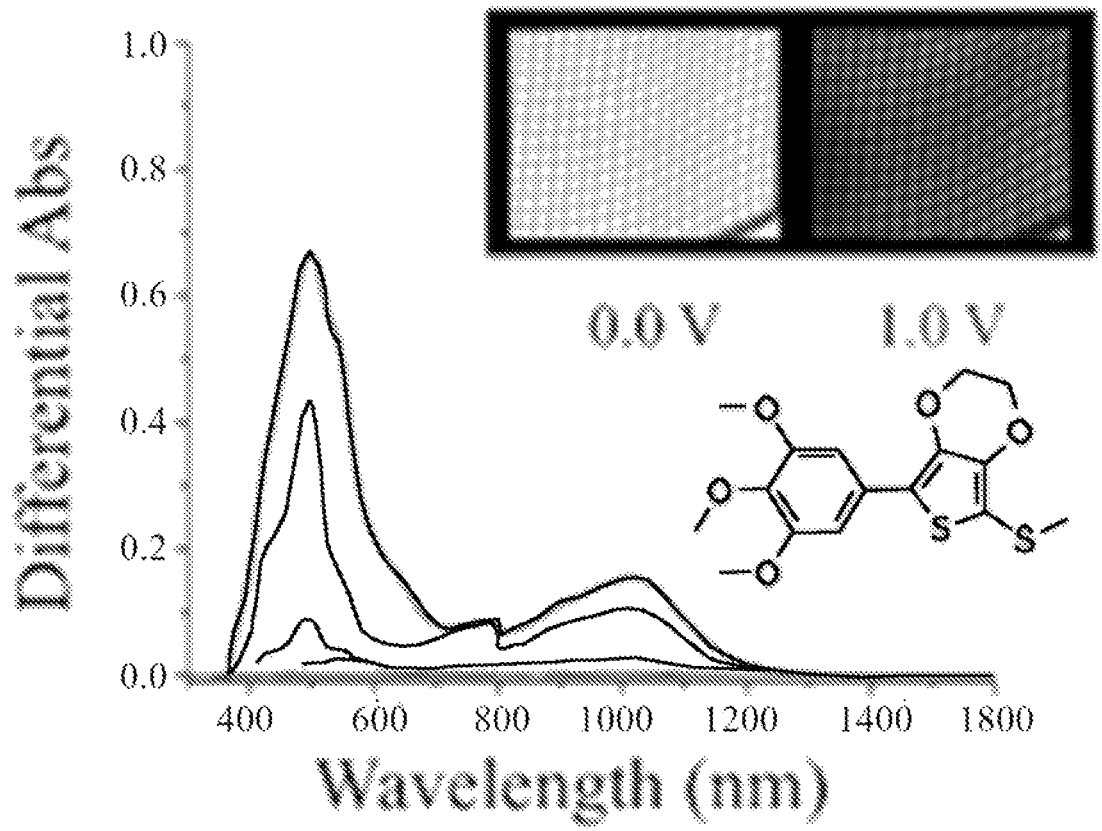

FIG. 3 details the exemplary set of anodically coloring electrochromes where the neutral and radical cation states' optical gaps are controlled independently. Using a valence shell electron pair repulsion (VSEPR) theory model, it can be seen that in the radical cation state, the Y substituents (meta) are more conjugated into the π-orbital system of the chromophore. These meta positions can therefore be used as a synthetic handle to vary the radical cation state's energy levels. Discrete chromophores based on a 2-thiomethyl-dioxythiophene coupled to a 4-methoxyphenylene are provided that give an anodically coloring electrochrome family (ACE) depicted in FIG. 3. Radical cation absorption control is achieved by readily altering the substitution pattern on the phenylene moiety, leading to charged states that absorb across the visible spectrum. The chromophores examined in this example increase in electron density donated to the radical cation state from ACE1 to ACE4. The para position is left as a methoxy in all cases to both add electron density and cap reactive ends to prevent radical-radical coupling.

Instrumentation and Characterization Techniques.

$^1$H NMR and $^{13}$C NMR spectra were collected on a Varian Mercury Vx 300 MHz instrument using CDCl$_3$ as a solvent and the residual CHCl$_3$ peak as references ($^1$H: δ=7.26 ppm; $^{13}$C: δ=77.23 ppm). All absorption spectra and spectroelectrochemistry were acquired using a Varian Cary 5000 Scan dual-beam UV-vis-near-IR spectrophotometer. Colorimetry measurements were obtained using Star-Tek colorimetry software using a D50 illuminant, 2 deg observer, and the L*a*b* color space. Spectroelectrochemical measurements were carried out using an EG&G Princeton Applied Research model 273A potentiostat/galvanostat under Corr-Ware control in a three-electrode cell configuration, using a Pt screen as a working electrode, a Ag/AgCl reference electrode, and a Pt flag as the counter electrode. Cyclic voltammetry (CV) and differential pulse voltammetry (DPV) were carried out with Pt button electrodes with a surface area of 0.02 cm$^2$. An electrolyte solution of 0.5 M tetrabutylammonium hexafluorophosphate (TBAPF$_6$, 98%, purified via recrystallization from hot ethanol) in dichloromethane (DCM) was used in all electrochemical and spectroelectrochemical measurements. Photography was performed in a light booth designed to exclude outside light with a D50 (5000K) lamp located in the back of the booth providing illumination, using a Nikon D90 SLR camera with a Nikon 18-105 mm VR lens.

Materials.

Most reagents and starting materials were purchased from commercial sources and used without further purification, unless otherwise noted. THF, toluene, and acetonitrile were all purified through a Bruker or Vacuum Atmospheres solvent purification system. All reactions were carried out under an argon atmosphere unless otherwise mentioned.

Synthetic Procedures

Synthesis.

The synthetic approach is shown in Scheme 1. Starting with commercially available 3,4-ehtylenedioxythiophene a lithiation followed by addition of dimethyldisulfide formed 2. Subsequent lithiation and transmetalation with trimethyltin chloride forms the desired compound, 3. The synthetic scheme diverges from here where 3 can be used for Stille coupling with a bromo-substituted phenylene (4, 5, 6, and 7) to prepare the target compounds ACE1, ACE2, ACE3, and ACE4.

Scheme 1. Synthetic Approach for Anodically Coloring Molecules of this example

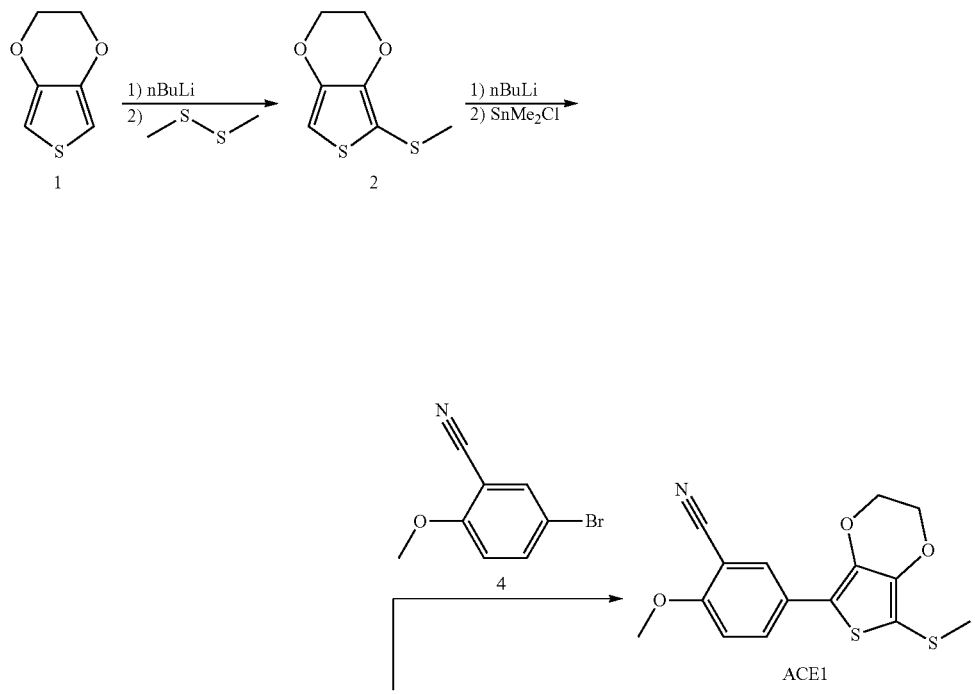

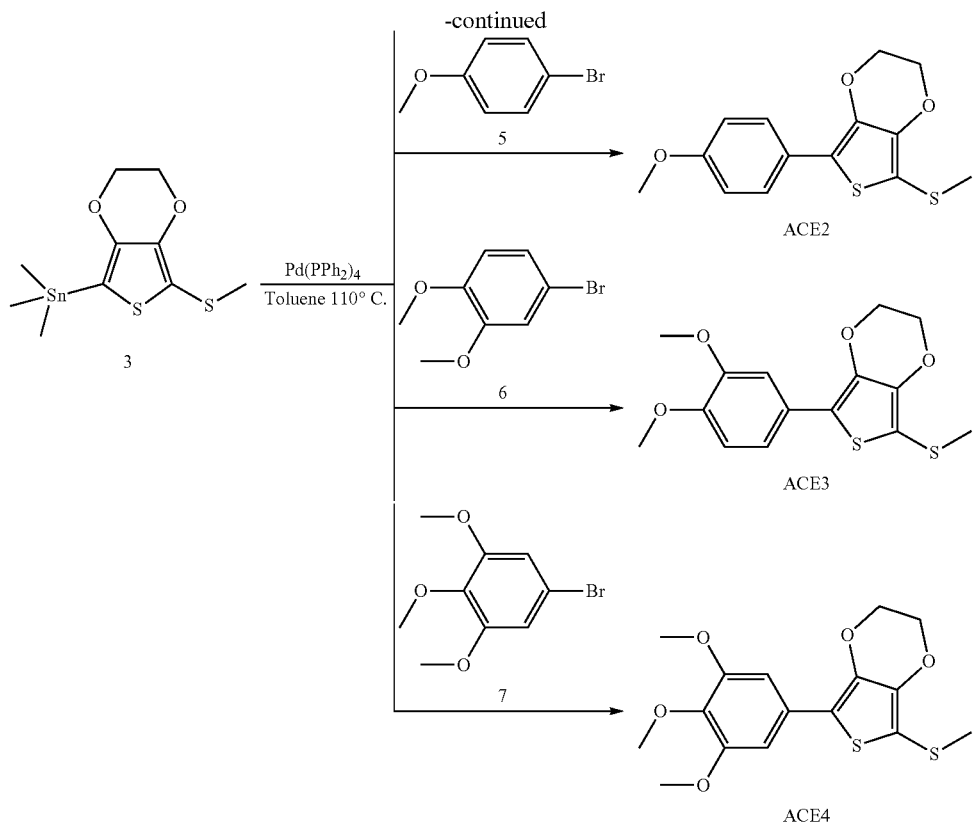

Synthesis of 2-thiomethyl-3,4-ethylenedioxythiophene (2)

Into a dry 250 mL schlenk flask with argon atmosphere and magnetic stir bar was added 1 (10.00 g, 70.34 mmol) and THF (100 mL). The solution was cooled to −78° C. and 2.5 M BuLi (28.2 mL, 70.5 mmol) was added drop wise via syringe pump over 1 hour. The solution was stirred for 1 hour at −78° C. and dimethyldisulfide (10.0 g, 106 mmol) was added in one dose. The solution stirred over 12 hours as it warmed to room temperature. The reaction mixture was poured over a mixture of ice (100 g) and 0.1M HCl (100 mL). The mixture was extracted with DCM (3×50 mL), the organic extracts were dried over anhydrous $MgSO_4$, and the solvent was removed under vacuum. The resulting clear oil was used without further purification. The yield was 11.92 g (90%). $^1$H-NMR ($CDCl_3$, ppm): δ 6.41-6.28 (s, 1H), 4.29-4.24 (d, 2H, J=9 Hz), 4.20-4.14 (d, 2H, J=9 Hz), 2.40-2.26 (s, 3H). $^{13}$C-NMR ($CDCl_3$, ppm): δ 143.26, 141.35, 108.69, 101.98, 64.98, 64.32, 21.31.

Synthesis of 2-thiomethyl-3,4-ethylenedioxy-5-trimethyltin-thiophene (3)

Into a dry 250 mL schlenk flask with argon atmosphere and magnetic stir bar was added 2 (5.00 g, 26.6 mmol) and THF (50 mL). The solution was cooled to −78° C. and 2.5 M BuLi (10.7 mL, 26.8 mmol) was added drop wise via syringe pump over 1 hour. The solution was stirred for 1 hour at −78° C. and trimethyltinchloride (5.34 g, 26.8 mmol) was added in one dose. The solution stirred over 12 hours as it warmed to room temperature. The reaction mixture was poured over a mixture of ice (100 g). The mixture was extracted with DCM (3×50 mL), the organic extracts were dried over anhydrous $MgSO_4$, and the solvent was removed under vacuum. The resulting white crystalline solid was used without further purification. The yield was 9.25 g (99%). $^1$H-NMR ($CDCl_3$, ppm): δ 4.27-4.22 (d, 2H, J=6 Hz), 4.18-4.13 (d, 2H, J=6 Hz), 2.41-2.31 (s, 3H), 0.58-0.02 (t, 9H, J=30 Hz). $^{13}$C-NMR ($CDCl_3$, ppm): δ 147.34, 1143.60, 113.95, 112.56, 64.94, 64.34, 21.25, −8.47.

General Stille Coupling Procedure

Into a dry 100 mL schlenk flask with argon atmosphere and magnetic stir bar was added 3 (0.50 g, 1.42 mmol), aryl bromide 4, 5, 6 or 7 (1.42 mmol), $Pd(PPh_3)_4$ (0.08 g, 0.07 mmol), and toluene (50 mL). The reaction was stirred at 100° C. for 12 hours and cooled to room temperature. The reaction was washed with water (3×50 mL), saturated $NaHSO_3$ (2×50 mL), and brine (1×50 mL). The organic layer was dried over $MgSO_4$ and solvent was removed under vacuum. The resulting compounds were purified by column chromatography with EtOAc/hexanes (1:9) as the eluent.

ACE1: Pale yellow fluffy solid in 89% yield (405 mg). Melt point: 192-193° C. $^1$H-NMR ($CDCl_3$, ppm): δ 8.00-7.94 (s, 1H), 7.78-7.71 (d, 1H, J=9 Hz), 6.98-6.91 (d, 1H, J=9 Hz), 4.36-4.28 (dt, 4H, J=3 Hz), 3.96-3.92 (s, 3H), 2.42-2.39 (s, 3H). $^{13}$C-NMR ($CDCl_3$, ppm): δ δ 159.67, 143.61, 137.77, 131.58, 131.25, 126.01, 116.70, 116.34, 111.52, 107.19, 102.09, 64.79, 64.54, 56.15, 21.25. HRMS, $C_{15}H_{13}O_3NS_2$ Calculated m/z: 319.0331, Measured m/z: 319.0331

ACE2: White crystalline solid in 83% yield (348 mg). Melt point: 90-91° C. 1H-NMR ($CDCl_3$, ppm): δ 7.69-7.54 (d, 2H, J=9 Hz), 6.96-6.81 (d, 2H, J=9 Hz), 4.37-4.22 (dt, 4H, J=3 Hz), 3.86-3.76 (s, 3H), 2.47-2.32 (s, 3H). $^{13}$C-NMR ($CDCl_3$, ppm): δ 158.59, 143.72, 136.70, 127.52, 125.36, 119.65, 114.07 105.35, 64.87, 64.42, 55.30, 21.45. HRMS, $C_{14}H_{14}O_3S_2$ Calculated m/z: 294.0379, Measured m/z: 294.0379

ACE3: White crystalline solid in 69% yield (319 mg). Melt point: 107-108° C. $^1$H-NMR (CDCl$_3$, ppm): δ 7.25-7.23 (d, 1H, J=3 Hz), 7.23-7.21 (d, 1H, J=3 Hz), 6.89-6.83 (s, 1H), 4.38-4.24 (dt, 4H, J=3 Hz), 3.95-3.90 (s, 3H), 3.90-3.86 (s, 3H), 2.44-2.36 (s, 3H). $^{13}$C-NMR (CDCl$_3$, ppm): δ 148.90, 148.21, 136.83, 125.58, 119.68, 118.92, 111.27, 109.75, 105.60, 64.86, 64.50, 55.92, 55.90, 21.42. HRMS, $C_{15}H_{16}O_4S_2$ Calculated m/z: 324.0485, Measured m/z: 324.0484

ACE4: Pale brown crystalline solid in 74% yield (374 mg). Melt point: 120-121° C. $^1$H-NMR (CDCl$_3$, ppm): δ 6.93-6.86 (s, 2H), 4.36-4.27 (dt, 4H, J=3 Hz), 3.90-3.87 (s, 6H), 3.86-3.84 (s, 3H), 2.43-2.34 (s, 3H). $^{13}$C-NMR (CDCl$_3$, ppm): δ 153.30, 143.59, 137.31, 128.14, 119.50, 106.50, 103.75, 64.83, 64.59, 60.93, 56.15, 21.31. HRMS, $C_{16}H_{18}O_5S_2$ Calculated m/z: 354.0590, Measured m/z: 354.0589

Quantum Chemical Calculations.

We have shown mPW1PBE functional paired with the cc-PVDZ basis set provides excellent correlation of optical properties to experimental spectra for these systems. To mimic the environment each system experiences during experimental data collection, all computations were performed with the incorporation of the conductor polarizable calculation model (CPCM) using dichloromethane as the applied dielectric. For each ACE, this level of theory was applied to a single chromophore in its neutral and radical cation states to predict changes in the optimized ground state geometry upon oxidation. Time-dependent DFT (TD-DFT) calculations were then performed on these geometries to simulate the lowest lying 15 excited states and the UV-Vis spectra.

Discussion

In order to guide experiment and probe the challenge from a molecular orbital perspective, time dependent density functional theory (TDDFT) calculations were performed on these molecules and theoretical spectra were generated for the neutral and radical cation states of the materials. There is very little change in the absorbance of the neutral spectra upon the addition of electron rich moieties at the meta position. All of the materials have a λmax in the UV with absorption onsets ~400 nm. However, when examining the radical cation spectra there are stark differences between in the spectra. While the high-energy absorption appears to be consistent between these materials, there is a significant red-shifting of the low energy transition. A particularly large redshift going from ACE2 to ACE3, which is explained by examining the energy levels and frontier molecular orbitals (FMOs).

The high-energy radical cation absorption is most strongly associated with the SOMOα→LUMOα transition with little difference in energy between the chromophores. The low energy absorption, however, is most strongly associated with a SOMO-1β→LUMOβ transition for ACE1 and ACE2 and SOMOβ→LUMOβ for ACE3 and ACE4. This shift explains the large jump in energy of this absorption between ACE2 and ACE3. This switch is attributed to the change in orbital overlap when more electron rich moieties are added to the system. While the LUMOβs remain fairly consistent in their orbital shape, it was observed that there is a large change in the shape of SOMOβ upon the addition of a methoxy group, with much of the orbital being placed on the EDOT portion of the chromophore. This change in orbital shape increases the overlap with LUMOβ, thus making the transition more favorable. Coarse control color is provided by changing which transitions dominate the absorption spectra.

Figures 5A, 5B:
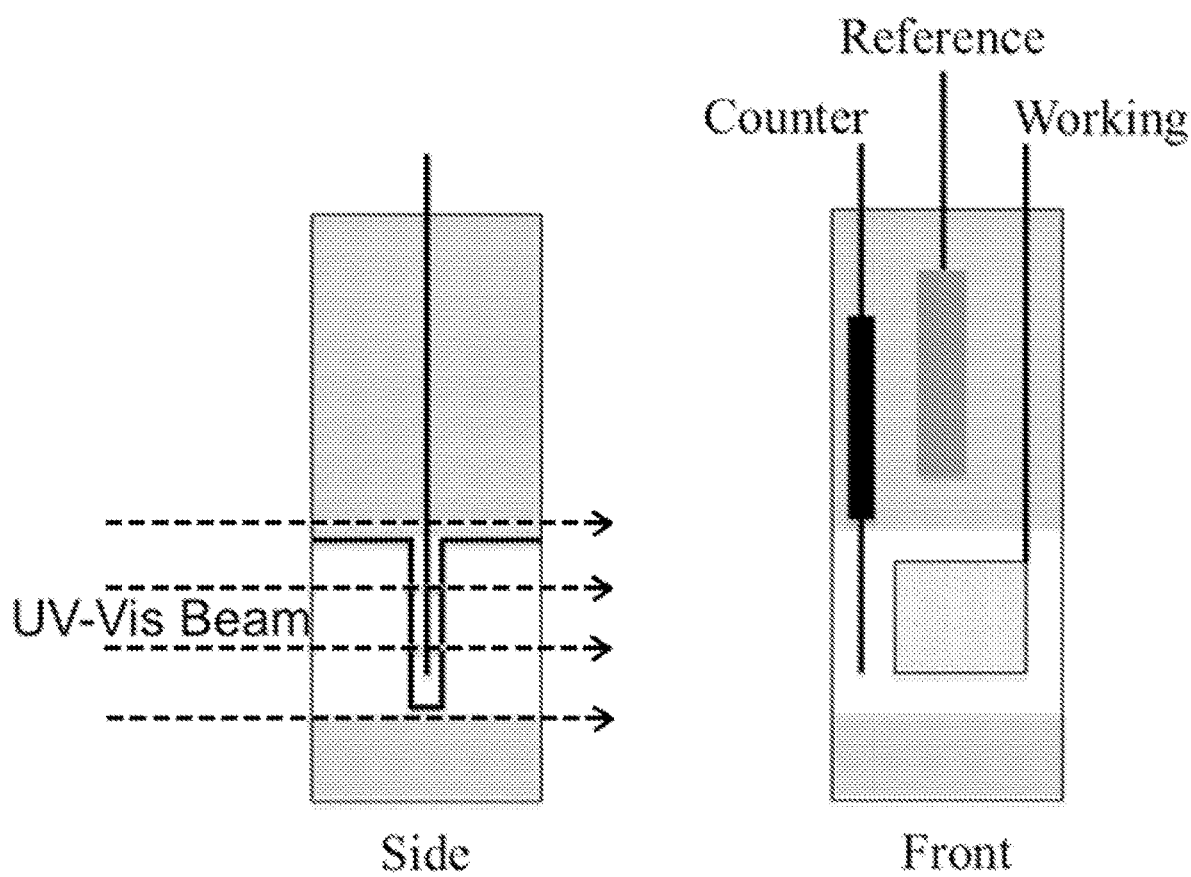
FIGS. 5A-5C demonstrate the design and nature of beam path and cropping for generating the differential spectroelectrochemistry with the optically transparent thin layer electrode (OTTLE).
Figure 5C:
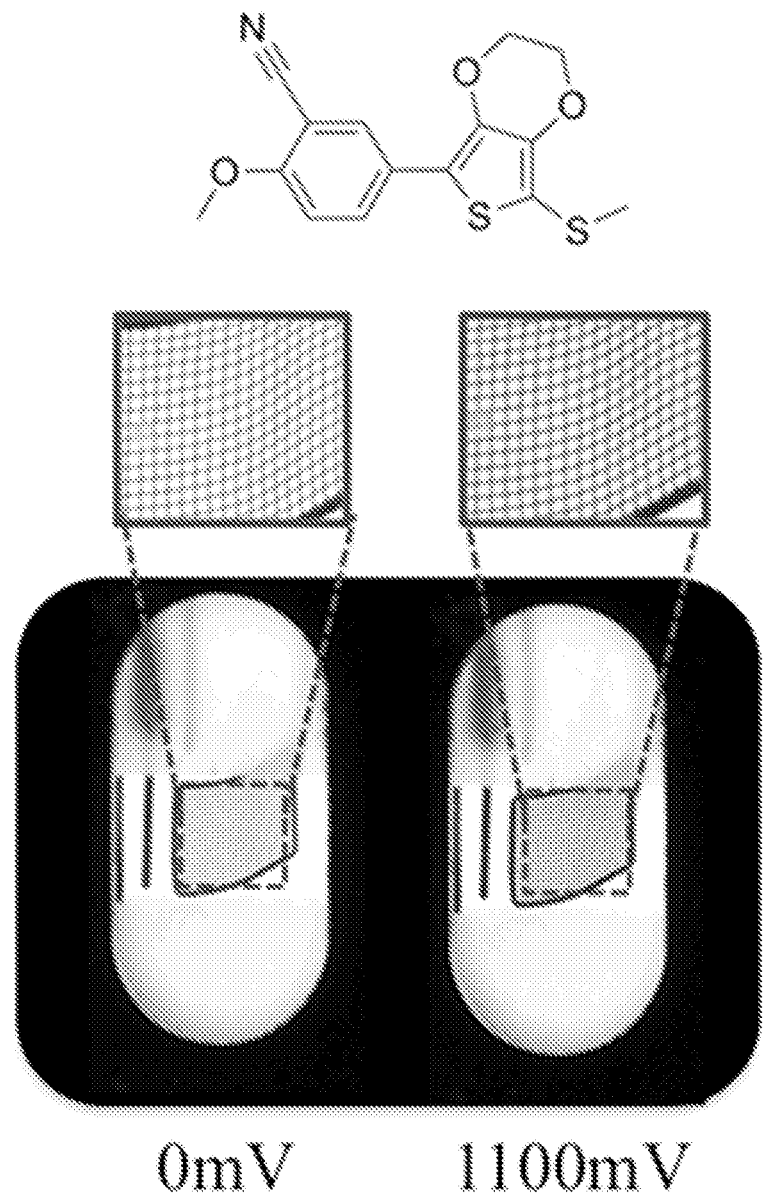

The experimental results are overall consistent with the picture painted above from the theoretical computations. FIGS. 4A-4D demonstrate the differential spectroelectrochemistry results performed in electrolyte solution using an optically transparent thin layer electrode (OTTLE). In this experiment the neutral spectrum is subtracted as a baseline in order to focus the change in absorbance upon oxidation. A schematic of the OTTLE is depicted in FIGS. 5A-5C. It should be noted that a Pt screen is the working electrode and is visible in each photograph. It should also be noted that the UV-Vis light source produces a beam that has an area larger than the working electrode leading to slight differences in absorbances relative to what is visible in the photographs. Comparing the spectra to the TDDFT results, it is evident that the calculations accurately depicted the location of the peaks and the red shifting trend seen in the low energy absorption upon the incorporation of the electron rich substituents. This ability to rationally-shift the low energy absorbance allows access to a large variety of colors through minimal changes in chemical structure. The bright green of the cyano-containing ACE1 is due to the combination of two peaks in the visible with $\lambda_{max}$ at 461 nm and 653 nm and a transmission window between 500-570 nm. Upon removing the electron-withdrawing group, there is a small shift in absorbance of the low energy radical cation peak for the parent molecule ACE2 with peaks arising at 471 nm and 683 nm and a more reshifted window of transmission at 520-590 nm, which yields a more saturated green color. The formation of the shoulder in the NIR for ACE2 at 915 nm is the first evidence of contribution from the SOMOβ→LUMOβ transition. As more electron density is added to the chromophore for ACE3, the contribution from the SOMO-1β→LUMOβ becomes suppressed with only a small absorbance observed at 597 nm, and large absorbances are measured at 469 nm and 986 nm. This is envisioned as a bright yellow color with only one strong transition being in the visible. When examining the most electron rich system, ACE4, it can be seen that the low energy peak red shifts to 1013 nm as predicted, and there is an observed red shift and broadening of the high-energy peak at 496 nm. The increased breadth of the high-energy radical cation peak when comparing ACE3 with ACE4 causes a color change from a vibrant yellow to a deep red. This broadening is indicative of the formation of a new charged species.

Figure 6A:
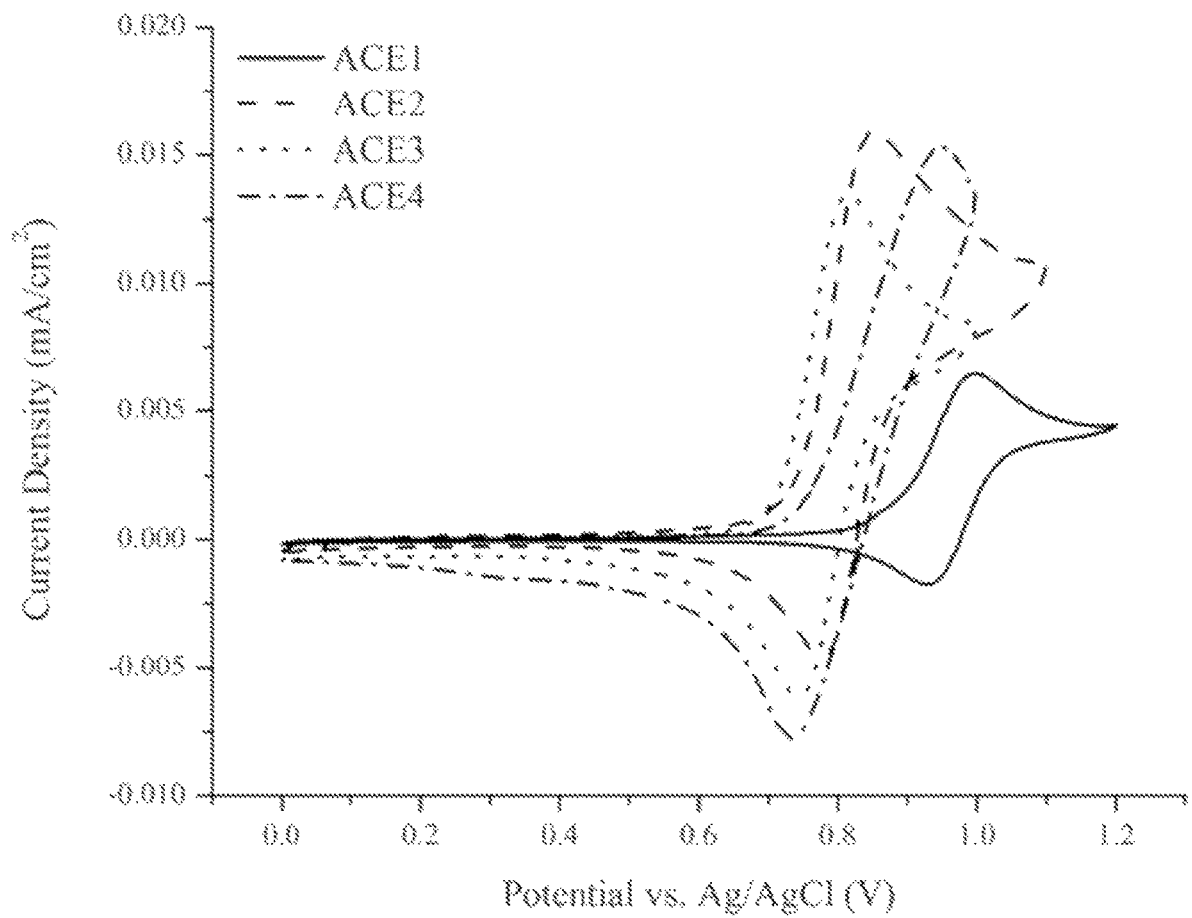
FIGS. 6A-6C are graphs of the cyclic voltammetry and differential pulse voltammetry results for the exemplary anodically coloring electrochromic molecules from Example 1.
Figure 6B:
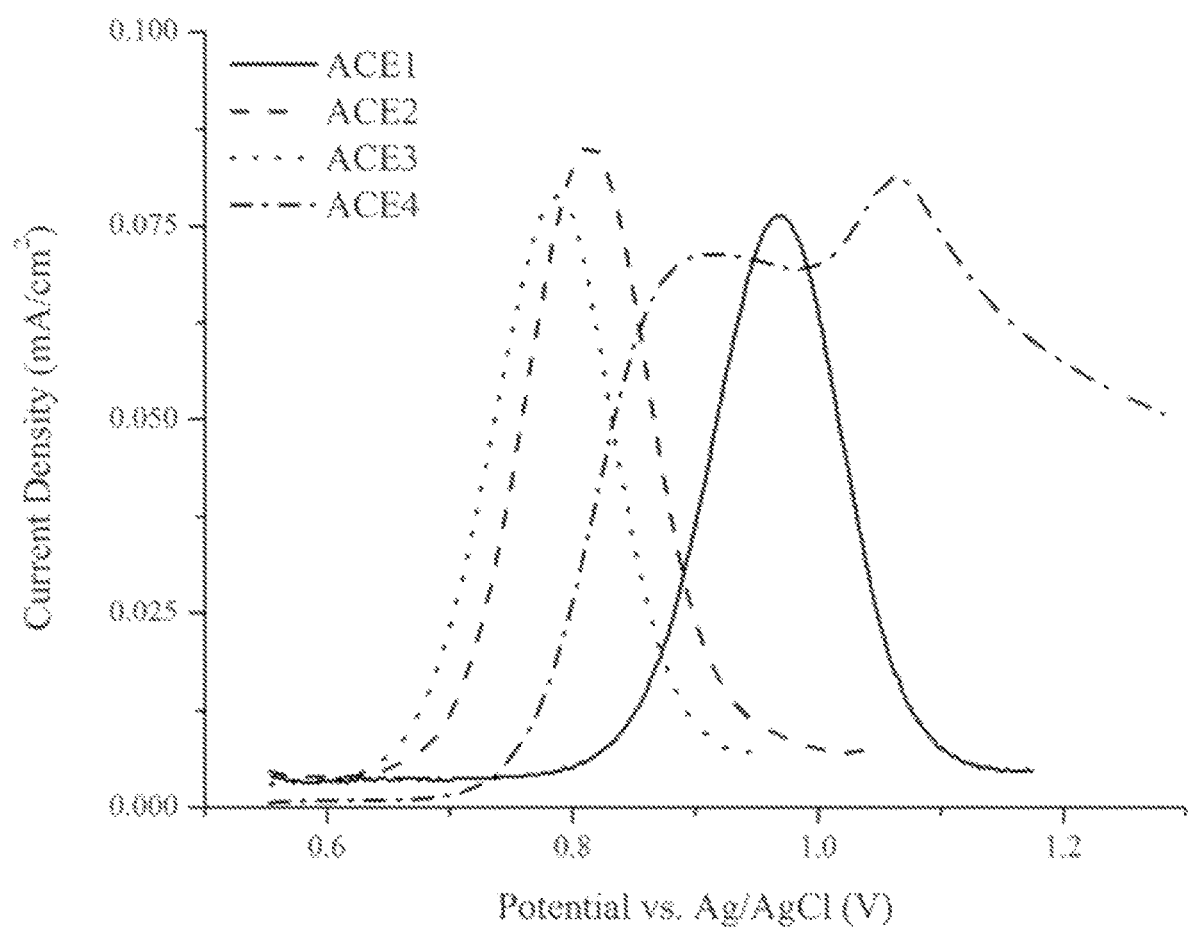
Figure 6C:
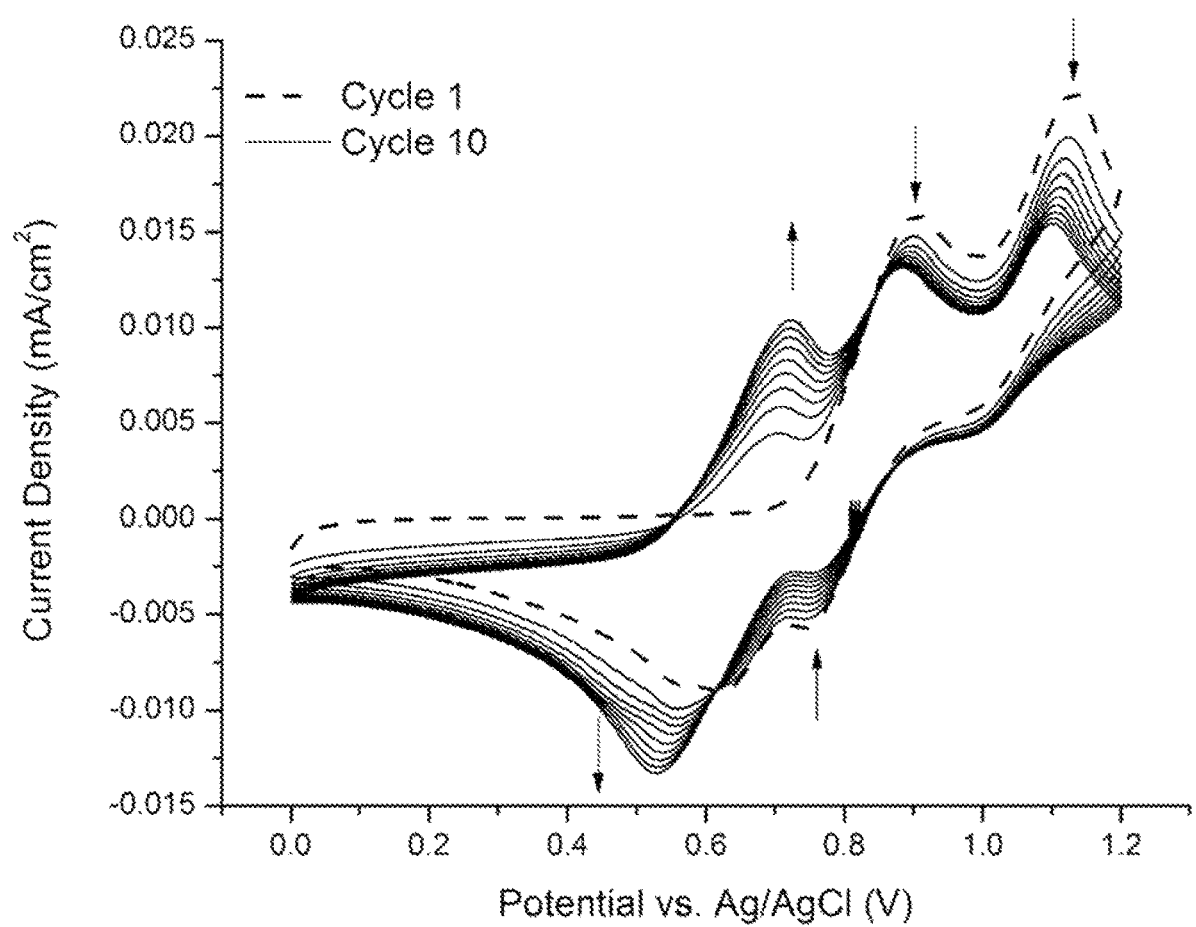
Figure 7A:
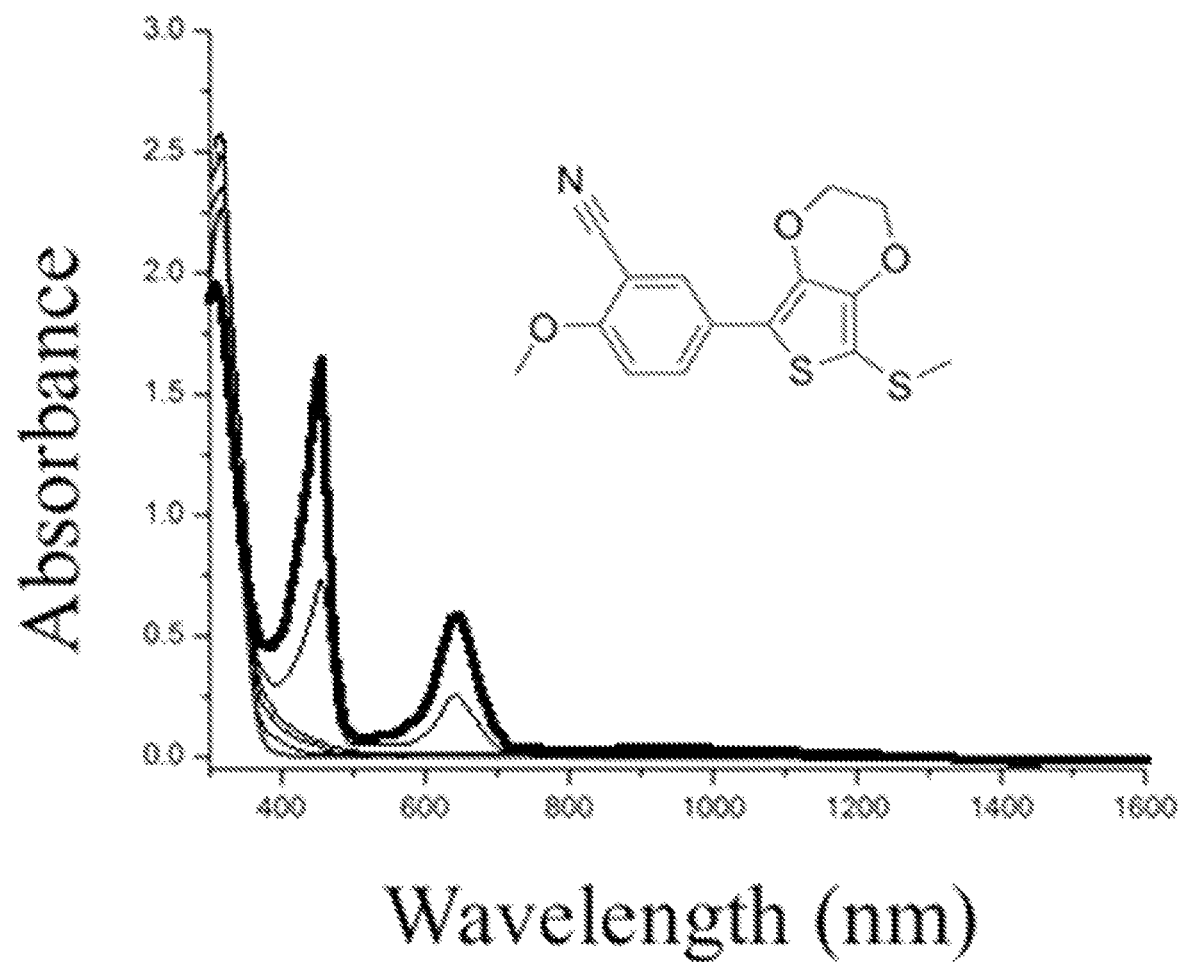
FIGS. 7A-7D are graphs depicting the evolution of UV-Vis absorbance of oxidatively doped solutions of the ACE molecules: ACE1 (FIG. 7A), ACE2 (FIG. 7B), ACE3 (FIG. 7C), and ACE4 (FIG. 7D). The solutions are 250 μM of each compound and Fe(OTf)$_3$ is the dopant.
Figure 7B:
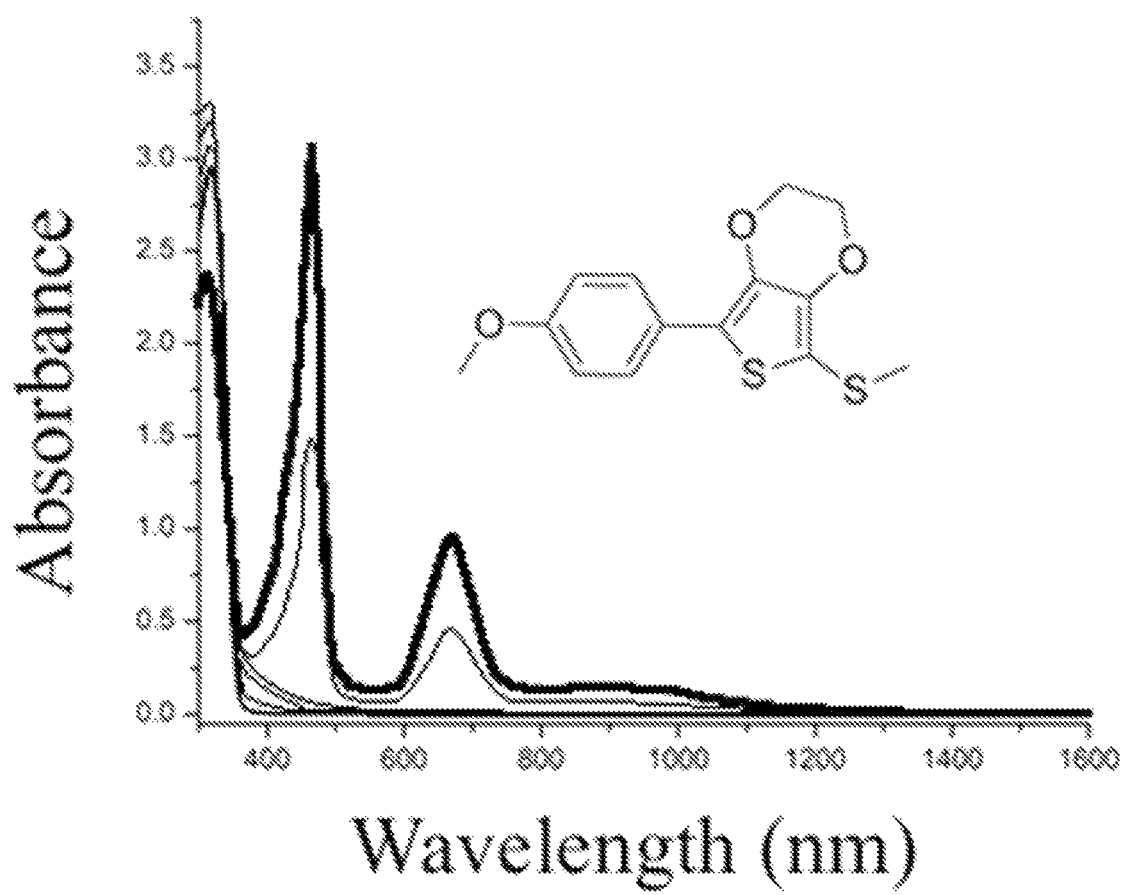
Figure 7C:
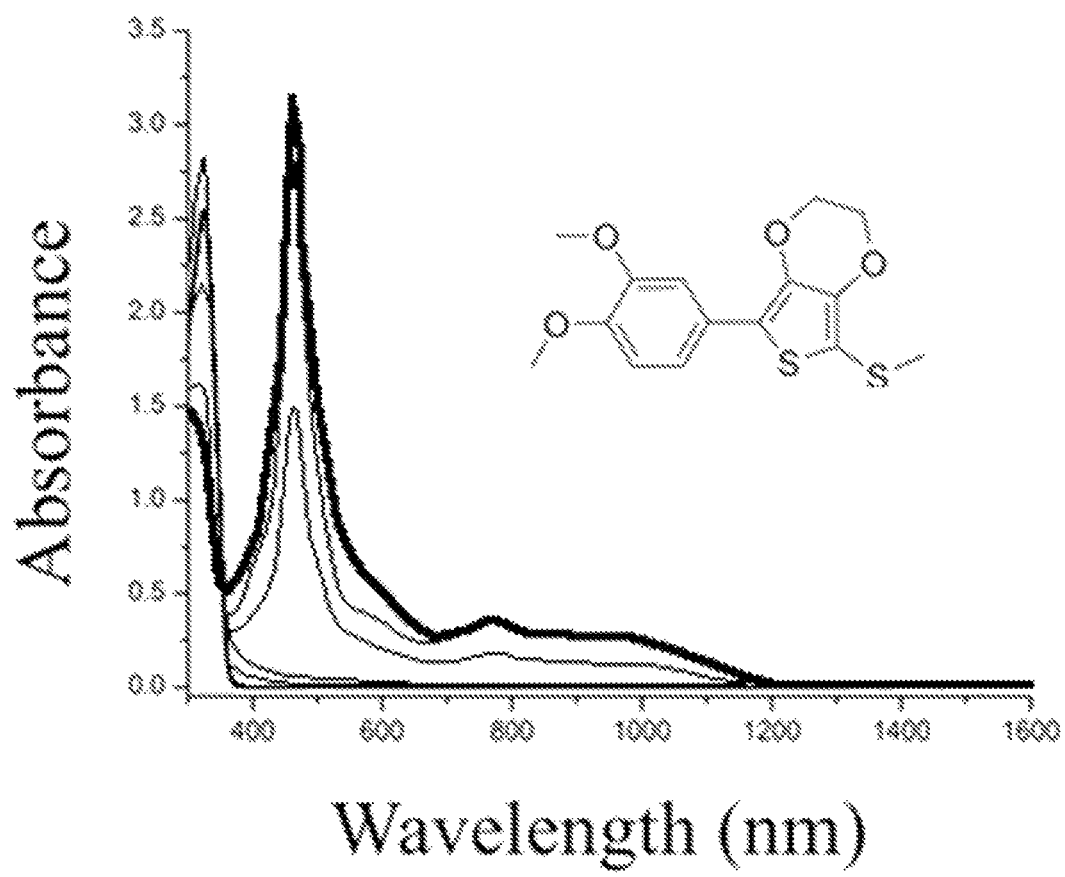
Figure 7D:
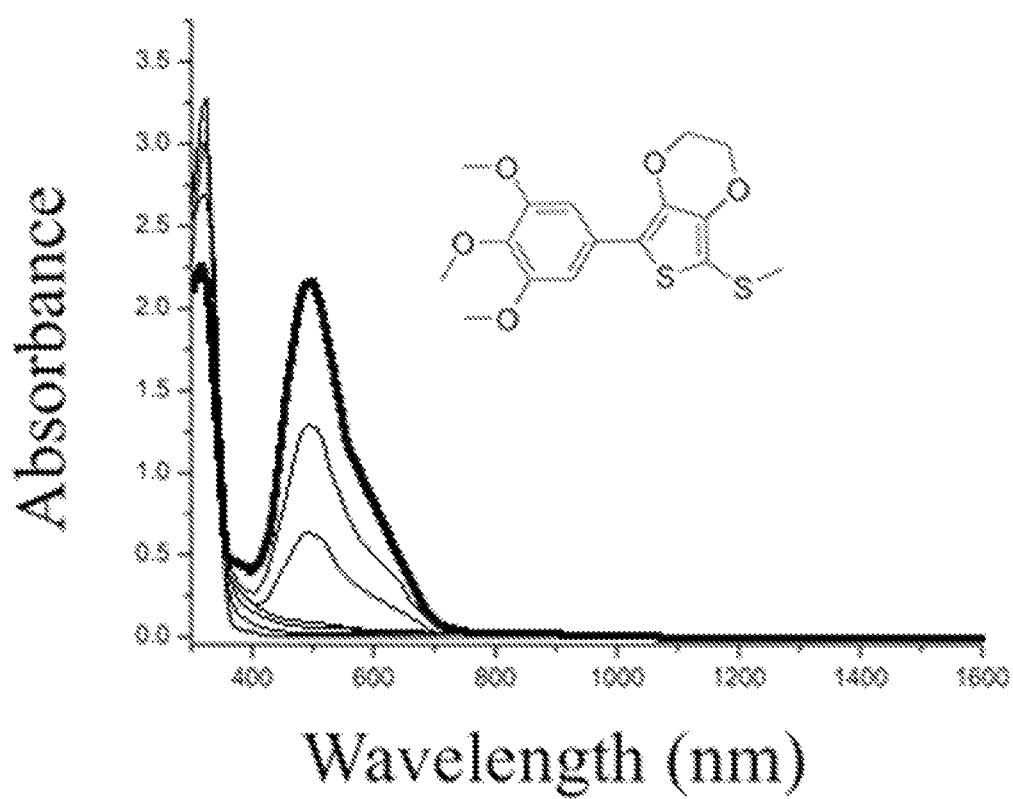
Figure 8:
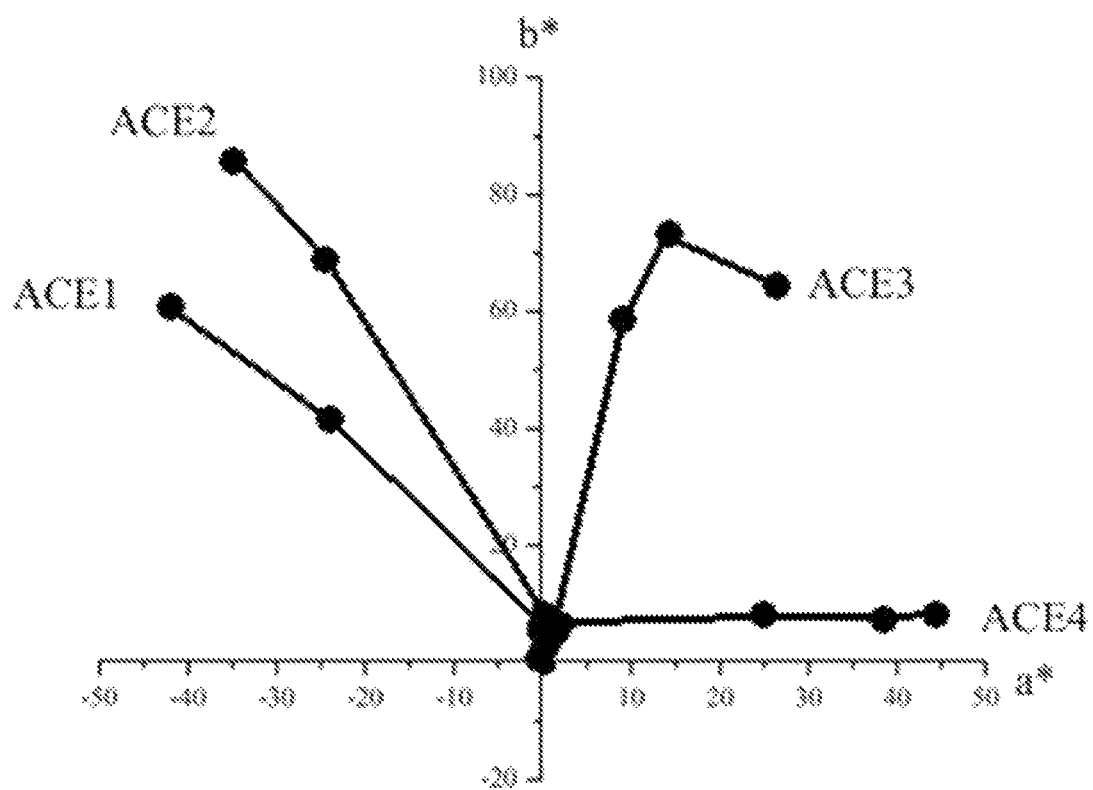
FIG. 8 is a graph demonstrating the evolution of colorimetry of oxidatively doped solutions of the ACE molecules. The solutions are 250 μM of each compound and Fe(OTf)$_3$ is the dopant.

Cyclic volatammetry (CV) and differential pulse voltammetry (DPV) were used to probe cation-radical formation and the results are shown in FIGS. 6A-6C. All of the molecules show reversible radical cation oxidations, but FIG. 6C shows that ACE4 has a two peaks indicative of the formation of a dication. This oxidation renders the electrochemistry irreversible and causes the formation of a new electroactive species, although it can be reduced back to neutral/colorless in the OTTLE when applying a reducing potential for an extended period. Formation of the dication would also corroborate with the apparent red shift of the high-energy radical cation peak relative to the other chromophores, as it is a combination of absorption from radical cations and dications, leading to the red color.

The UV-Vis data and the color neutrality and transmissivity of the neutral state and the color vibrancy obtained through chemical oxidative doping is shown in FIGS. 7A-7D and FIG. 8 respectively. This experiment was performed in 250 μM solutions with Fe(OTf)$_3$ as the oxidizing dopant. Photographs are taken in borosilicate vials before exposure to air. The a*b* plot shows the quantitative change in color upon sequential oxidative doping as calculated from the UV-Vis absorbance spectra of neutral and doped solutions. All calculated L*a*b* values for the neutral compounds are (100, 0, 0), which can be observed in the photographs as being completely color neutral and transmissive (i.e. colorless). Each of these compounds is oxidized to a vivid color that, in combination, cover a wide area in the color space. The absorptions generated with chemical oxidation are similar to what is seen in the OTTLE, with the exception of ACE4. This material has a single peak upon oxidation with a $\lambda_{max}$ at 496 nm, which is more evidence indicative of this material forming a dication upon doping. This material appears to oxidize directly to the dication upon chemical doping, as there is no spectral evidence of the radical cation forming. This is not unexpected due to how close the electrochemical peaks in the CV are measured to be.

Figure 9:
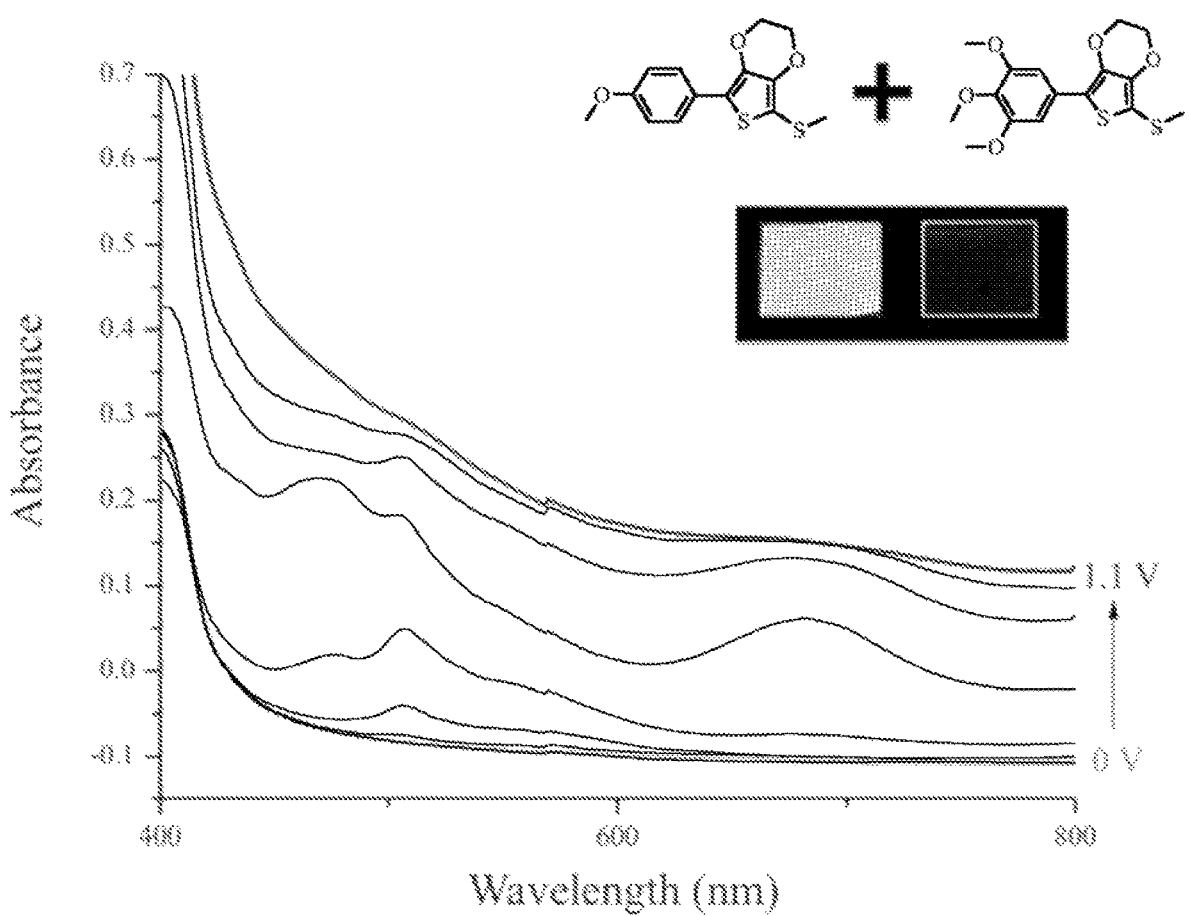
FIG. 9 is a spectroelectrochemistry performed with an OTTLE of a 1:1 mixture of ACE2 and ACE4 with photographs in the inset at the extreme potentials as noted.
Figure 10:
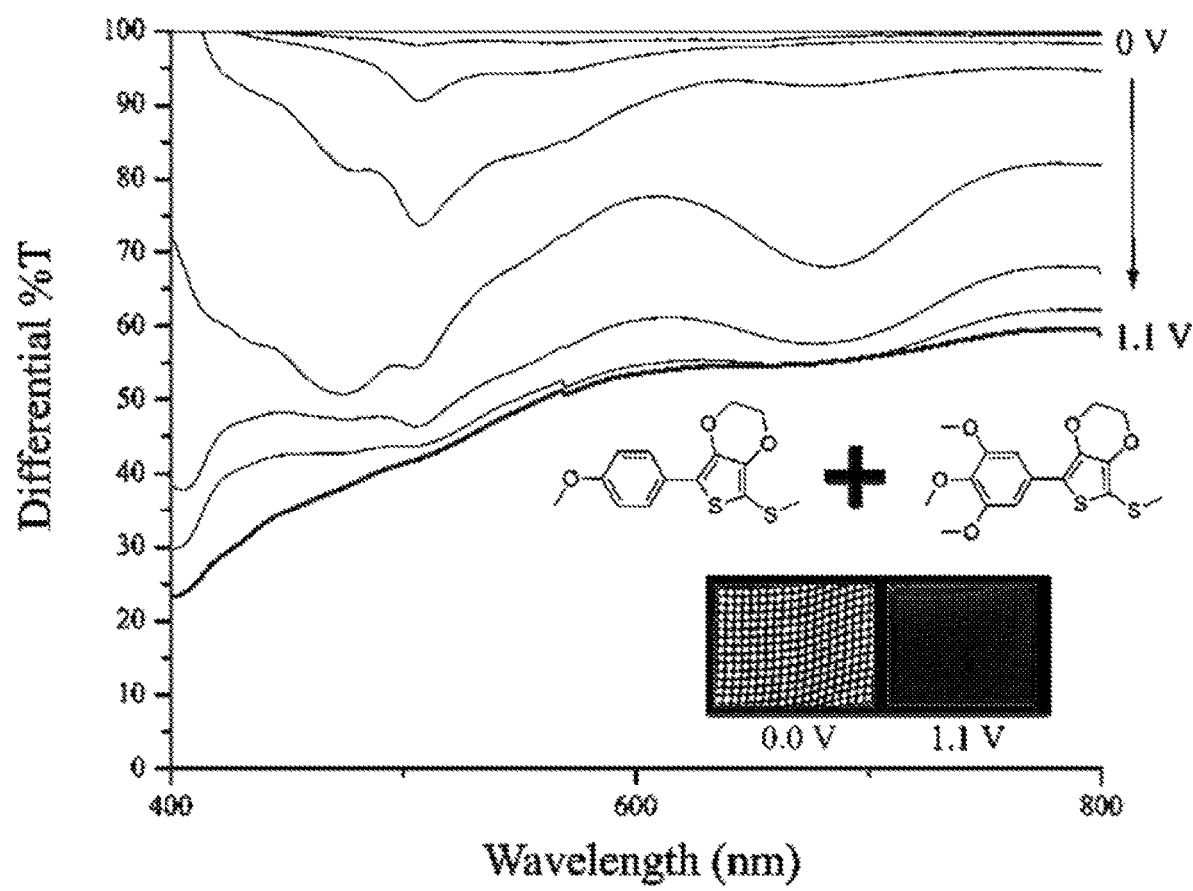
FIG. 10 is a differential spectroelectrochemistry performed with an OTTLE of a 1:1 mixture of ACE2 and ACE4 with photographs in the inset at the extreme potentials as noted.

With an ultimate goal of creating transmissive to black switching electrochromic blends, a mixture of ACE2 and ACE4 was created. The absorbance is plotted in FIG. 9 and the differential spectroelectrochemistry and photography is shown in FIG. 10 for a 1:1 solution mixture of ACE2 and ACE4. As can be seen from the photography, the mixture goes from a color neutral and transmissive solution to an opaque black with only a 1 mm path length through the OTTLE at a concentration of 250 μM. The blends can be tuned to create browns and other secondary colors from only a few materials for their potential use in eyewear applications.

In conclusion, the examples demonstrate a design paradigm for making anodically coloring materials where there is synthetic control on the absorption of the oxidized state. This absorption can be tailored through the use of electron donating/withdrawing moieties cross-conjugated into the neutral structure. This control enables the design materials with specific target colors in mind. With calculations to guide materials design and synthetic efforts to create new systems, next generation electrochromic materials offer the ability for precise color control. The results demonstrate that these materials have overcome the contrast barrier that is in the field of organic electrochromic materials while maintaining control of a wide variety of tunable colors and secondary blends.

Example 2: Anodically Coloring Electrochromic Molecules Incorporating Multiple 2-hexyl-dioxythiophene Rings Coupled to a 2,5-dimethoxyphenylene The anodically coloring compound ACE5, synthesis depicted below in Scheme 2, was synthesizes via direct heteroarylation. ACE5 incorporates multiple 2-hexyl-dioxythiophene rings coupled to a 2,5-dimethoxyphenylene.

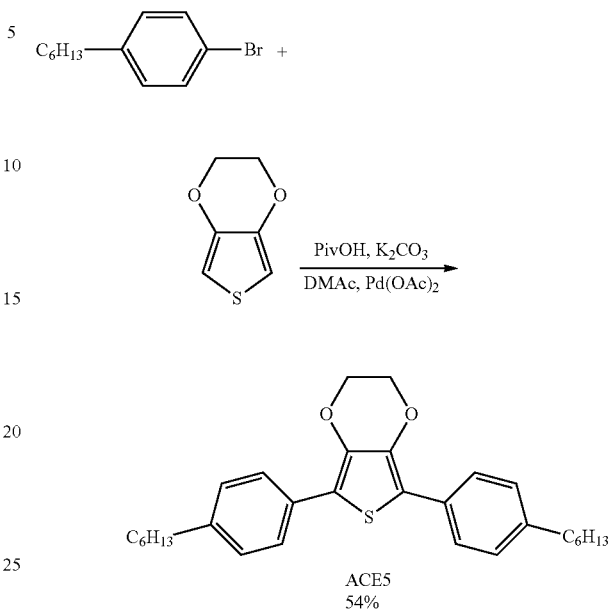

Scheme 2. Synthetic Approach for the Anodically Coloring Molecule of this example (PivOH = pivalic acid and DMAc = N,N-dimethylacetamide)

Figure 11:
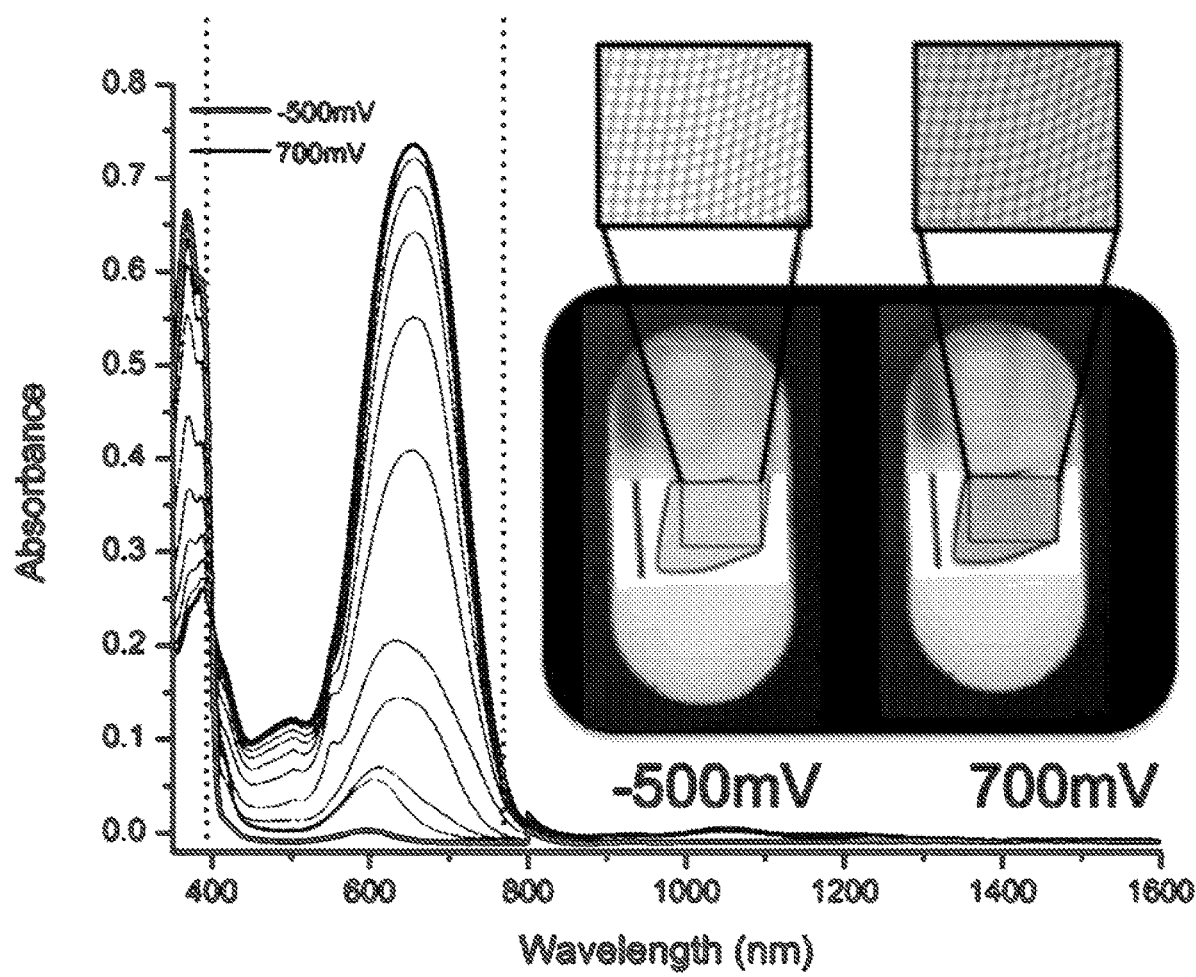
FIG. 11 is a graph of the spectroelectrochemistry performed on ACE5 in an optically transparent thin layer electrode (OTTLE) with photographs in the insets at the extreme potentials as noted.

The spectroelectrochemistry results for ACE5 are depicted in FIG. 11 demonstrating the single strong absorption band around 670 nm that appears in the radical cation state giving rise to a deep blue color. This single band comes from the symmetry of the frontier molecular orbitals in the radical cation state due to the symmetrical nature of the chemical structure.

Example 3: Anodically Coloring Electrochromic Polymers Based on Alkylene-Linked Discrete Chromophore Polymers This example demonstrates the design principles of creating multi-heterocycle chromophores with a discrete conjugation length, which absorb ultraviolet light in the neutral state, and upon oxidation absorb a broad spectral range in the visible. In this analysis, three discrete length chromophore polymers with alkylene linkers were examined via time dependent DFT, synthesized via direct heteroarylation polymerization, and the electrochromic properties of their thin film characterized. Using a feedback loop of theoretical calculations with design and synthesis, this example demonstrates how steric interactions can be used to control the absorption of the neutral and oxidized states of these discrete chromophore polymers. The results demonstrate that systems with high inter-ring strain can be used to increase the molar absorptivity of the charged state by forming multiple radical cation states on a single discrete chromophore. The results also demonstrate the challenges of electrochemical redox reversibility in the solid state in these systems, while they maintain their chemical redox reversibility.

Towards this aim, a family of polymers with discrete length rr-conjugated chromophores was synthesized to give insight into these fundamental structure-property relationships (repeat unit structures in Scheme 3) with the goal of providing design characteristics for anodically coloring electrochromic polymers. This family of chromophores models the interplay between increasing chromophore conjugation length and interring steric strain and examines the absorption characteristics of both the neutral and radical cation states of the chromophores, while using electron rich moieties to maintain a low oxidation potential.

spectroelectrochemical measurements. Films were spray-cast onto the ITO-coated glass slides using an Iwata airbrush at 25 psi from 3 mg/mL toluene solutions. Photography was performed in a light booth designed to exclude outside light

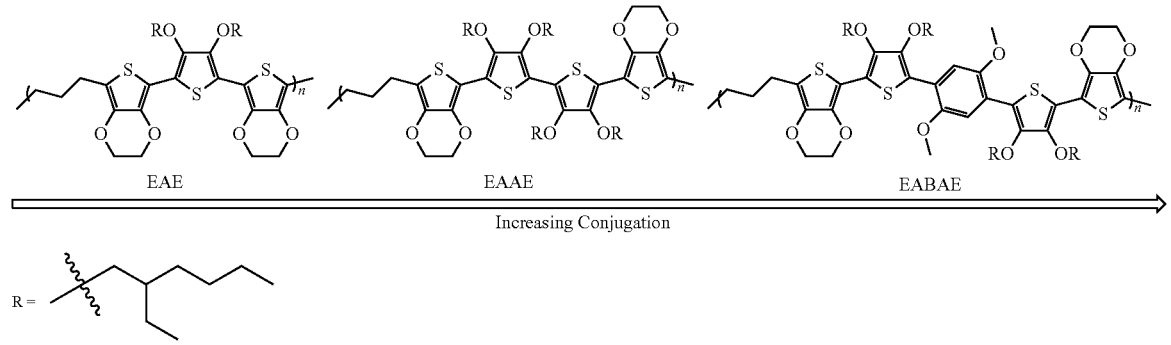

Scheme 3. Repeat unit structures for a family of dioxythiophene based discrete length chromophore polymers being investigated in order of increasing conjugation.

Instrumentation.

$^1$H NMR and $^{13}$C NMR spectra were collected on a Varian Mercury Vx 300 MHz instrument using CDCl$_3$ as a solvent and the residual CHCl$_3$ peak as references ($^1$H: δ=7.26 ppm; $^{13}$C: δ=77.23 ppm). Gel permeation chromatography (GPC) was performed using a Tosoh EcoSEC HLC-8320 GPC at 40° C. in chloroform. A TSKgel column (4.6 mm×150 mm) and PStQuick polystyrene standards from Tosoh were used. Polymer solutions (1 mg/mL in CHCl$_3$) were prepared and filtered through a PTFE 0.45 μm filter. 20 μL of each polymer solution was injected, and molecular weights were calculated using EcoSEC GPC System Workstation Software. All absorption spectra and spectroelectrochemistry were acquired using a Varian Cary 5000 Scan dual-beam UV-vis-near-IR spectrophotometer. Colorimetry measurements were obtained using Star-Tek colorimetry software using a D50 illuminant, 2 deg observer, and the L*a*b* color space. For the solution spectra, all polymers were dissolved in toluene at room temperature. Electrochemical measurements were carried out using an EG&G Princeton Applied Research model 273A potentiostat/galvanostat under CorrWare control in a three-electrode cell configuration, using ITO/glass (Delta Technologies Inc., 7×50×0.7 mm, sheet resistance, Rs 8-12 Ω/sq) as the working electrode, a Ag/Ag$^+$ reference electrode (10 mM AgNO$_3$ in 0.5 M TBAPF$_6$-propylene carbonate (PC), $E_{1/2}$ for ferrocene: 0.125 V), and a Pt flag as the counter electrode. For differential pulse voltammetry (DPV) measurements, the samples were prepared via drop-casting a 0.5 mg/mL solution onto glassy carbon button electrode with a surface area of 0.07 cm$^2$. An electrolyte solution of 0.5 M TBAPF$_6$ (98%, purified via recrystallization from hot ethanol) in PC was used in all electrochemical and spectroelectrochemical measurements. PC was purified using a solvent purification system from Vacuum Atmospheres. ITO coated glass slides were cleaned with toluene, acetone, and isopropanol prior to use and implemented as the working electrode for the with a D50 (5000K) lamp located in the back of the booth providing illumination, using a Nikon D90 SLR camera with a Nikon 18-105 mm VR lens.

Materials.

Most reagents and starting materials were purchased from commercial sources and used without further purification, unless otherwise noted. THF, toluene, and propylene carbonate were all purified through a Bruker or Vacuum Atmospheres solvent purification system. 2,5-dibromo-3,4-bis(2-ethylhexyloxy)thiophene (AcDOT), 2,5'-dibromo-3,3',4,4'-tetrakis((2-ethylhexyl)oxy)-2,2'-bithiophene (AcDOT$_2$), and AcDOT-Ph(OMe)$_2$-AcDOT-Br$_2$ were used as synthesized in previous literature (K. Cao, D. E. Shen, A. M. Osterholm, J. A. Kerszulis and J. R. Reynolds, *Macromolecules*, 2016, 49, 8498-8507; J. A. Kerszulis, C. M. Amb, A. L. Dyer and J. R. Reynolds, *Macromolecules*, 2014, 47, 5462-5469.).

Synthesis.

The target polymers in Scheme 3 were synthesized as described in Scheme 4. By lithiation of 3,4-ethylenedioxythiophene (EDOT) and subsequent quenching with propylene-1,3-ditosylate the dihydrin monomer (E-E) was synthesized. The polymerizations were carried out via a direct heteroarylation mechanism with the respective dibromo monomers to create the family of polymers with discrete chromophores. The polymers were purified via Soxhlet extraction and the repeat unit structure confirmed using $^1$H and $^{13}$C NMR and elemental analysis. Polymer molecular weights were analyzed with gel-permeation chromatography (GPC) in CHCl$_3$ at 40° C. and the number average molecular weights and dispersity ($M_n$, Đ) relative to polystyrene standards are as follows: EAE (14.8 kDa, 2.0), EAAE (18.5 kDa, 1.8), EABAE (9.7 kDa, 2.0). Synthetic procedures for E~E can be found below along with characterization results on $^1$H-NMR, $^{13}$C-NMR, mass spectrometry, elemental analysis, and GPC.

Scheme 4. Synthetic scheme outlining the synthesis of the target polymers. (PivOH = pivalic acid and DMAc = N,N-dimethylacetamide)

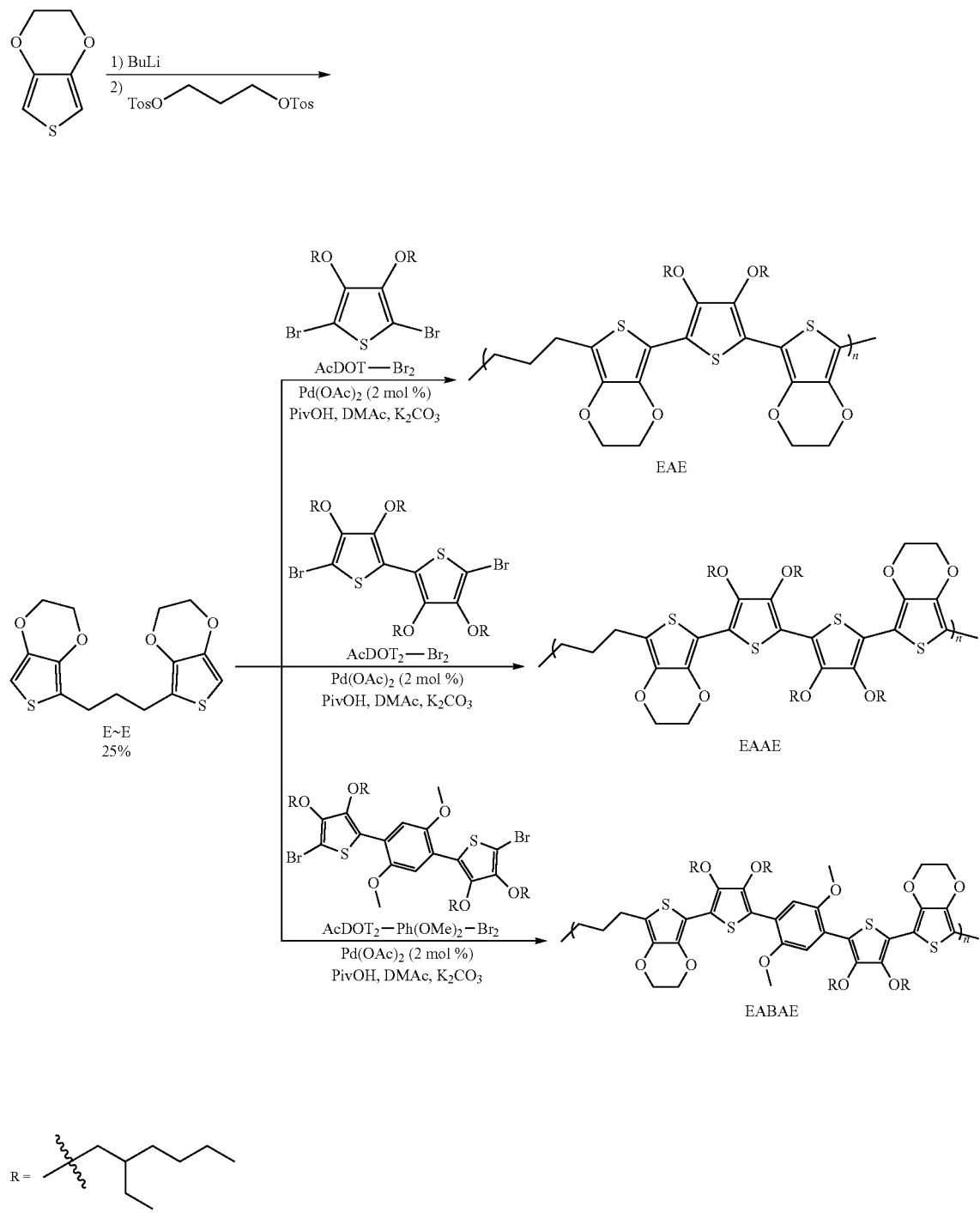

EAE.

Into a dry 25 mL schlenk tube with magnetic stirring was added the dibromide monomer AcDOT-Br$_2$ (0.1535 g, 0.3083 mmol), the dihydrin monomer EDOT$_2$ (0.1000 g, 0.3083 mmol), 2 mol % palladium acetate (1.5 mg, 0.0066 mmol), pivalic acid (0.0310 g, 0.3035 mmol), potassium carbonate (0.1378 g, 0.9970 mmol), and 3.1 mL of DMAc. The reaction mixture was purged with Ar, placed in an oil bath at 130° C., and stirred for 24 hours under positive Ar pressure. The mixture was cooled to room temperature and added drop wise to 100 mL of methanol. The precipitate was filtered through a Soxhlet thimble, and washed with methanol, acetone, hexanes, and chloroform respectively. The washings were conducted until color was no longer observed during extraction. The solvent was evaporated from the fraction and a pale-yellow solid was collected (0.1004 g, 49.3%). ¹H-NMR (CDCl₃, ppm): δ 4.29-4.20 (d, 8H), 3.93-3.90 (d, 4H), 2.72 (t, 4H), 1.96-1.84 (bm, 4H), 1.59~1.25 (bm, 16H), 0.91~0.87 (bm, 12H). Elemental analysis: Theory: C=63.60%, H=7.32%, S=14.55%, Found: C=63.38%, H=7.37%, S=14.28%. GPC analysis: M$_n$=14.8 kDa, Đ=2.0.

EAAE.

The polymer was synthesized using the same procedure as EAE, but with the dibromide monomer AcDOT₂-Br₂ (0.2580 g, 0.3083 mmol). The polymer was collected as a yellow solid (0.1638 g, 53.2%). ¹H-NMR (CDCl₃, ppm): δ 4.20-4.14 (d, 8H), 3.87-3.85 (d, 8H), 2.66 (t, 4H), 1.85 (m, 6H), 1.64-1.02 (bm, 32H), 0.98~0.58 (bm, 24H). Elemental analysis: Theory: C=66.09%, H=8.27%, S=12.83%, Found: C=65.63%, H=8.29%, S=12.50%. GPC analysis: M$_n$=18.5 kDa, Đ=1.8.

EABAE.

The polymer was synthesized using the same procedure as EAE, but with the dibromide monomer AcDOT₂-Ph (OMe)₂-Br₂ (0.2999 g, 0.3083 mmol). The polymer was collected as a yellow solid (0.1705 g, 48.7%). ¹H-NMR (CDCl₃, ppm): δ 7.37 (s, 2H), 4.29-4.22 (d, 8H), 3.97 (d, 4H), 3.84 (bm, 10H), 2.75-2.72 (q, 4H), 1.64-1.02 (bm, 32H), 0.98~0.58 (bm, 24H). Elemental analysis: Theory: C=66.63%, H=7.99%, S=11.29%, Found: C=66.40%, H=7.99%, S=11.05%. GPC analysis: M$_n$=9.7 kDa, Đ=2.0.

Quantum Chemical Calculations—Interring Strain.

To elucidate the influence of structural modification on the electronic and spectral properties of the chromophores, density functional theory (DFT) was utilized. mPW1PBE functional paired with the cc-PVDZ basis set (detailed information for each included in the Supplemental Information) provides excellent correlation of optical properties to experimental spectra for dioxythiophene-containing systems. To mimic the environment each system experiences during experimental data collection, all computations were performed with the incorporation of the conductor polarizable calculation model (CPCM) using dichloromethane as the applied dielectric. For each ECP, this level of theory was applied to a single chromophore in its neutral, radical cation, and dication states to predict changes in the optimized ground state geometry upon oxidation. Time-dependent DFT (TD-DFT) calculations were then performed on these geometries to simulate UV-Vis spectra, which provided insight on tuning the absorptivity of chromophores. Chromophores with high energy π-π* transitions were designed by restricting the conjugation length to three, four, and five heterocycles while also maintaining a low oxidation potential.

The impact of interring strain between neutral and oxidized states was examined utilizing the first set of ter (heterocycle) systems shown in Scheme 5. Each chromophore contained terminal groups of methyl-capped 3,4-ethylenedioxythiophene (E) and a distinct middle heterocycle: either a branched alkyl ether functionalized 3,4-propylenedioxythiophene (P) or a 3,4-bis(2-ethylhexyloxy)thiophene (A). By changing the identity of the middle heterocycle, the proximity of the alkoxy-chains relative to the conjugated backbone varied as a function of distance, while the number of π-electrons in the chromophore remained unchanged. The degree of interring strain was determined by observing the changes in dihedral angles between the terminal and middle heterocycles in each chromophore.

Scheme 5. Methyl-terminated ter(heterocycles) evaluated in the strain study.

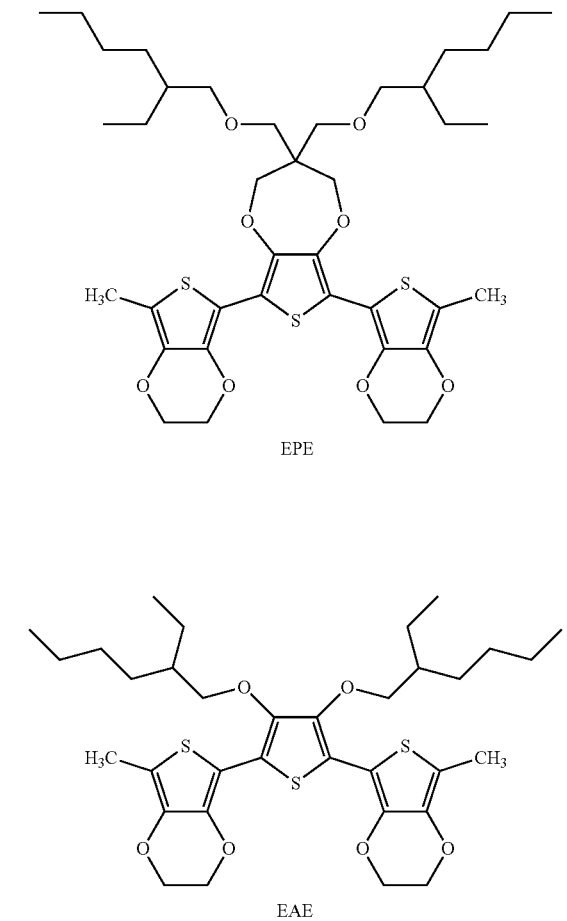

The results of the structural data for these ter(heterocycles) from the optimized geometry are collated in Table 1. The rings were numbered in each chromophore, and the interring bond lengths, dihedral angles, and first excited state energies (TD-DFT HOMO-LUMO gap) were measured. Examining the dihedral angle measurements, it is clear that the proximity of the 2-ethylhexyl solubilizing groups affect the degree of conjugation as the HOMO-LUMO gap for EAE is 0.68 eV higher than EPE. Since the solubilizing chains are farther from the backbone of the chromophore in EPE, all three heterocycles remain in excellent conjugation with one another, independent of the charged state. However, for the neutral EAE chromophore, only two of the three heterocycles are found to be exceptionally planar (175.2°) while the third heterocycle remains orthogonal (91.5°). Upon oxidation, the EAE chromophore becomes increasingly planar, reducing the orthogonal character (178.8° and 164.4°). The oxidized chromophores exhibit more quinoidal character as the bond length between heterocycles decrease by ~0.03 Å.

TABLE 1

Structural data for all target oligomers in this study. The key
shows how rings and dihedral angles are numbered and symbolized in the table.

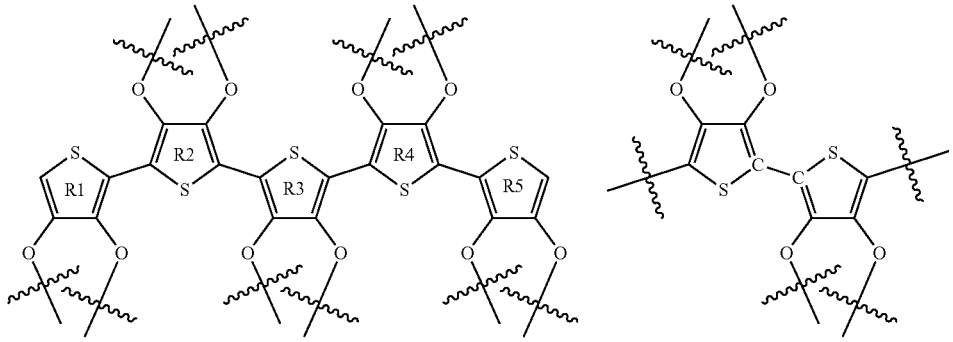

| | \multicolumn{8}{c}{Dihedral measurements} |
| | EPE | | EAE | | EAAE | | EABAE | |
| | neutral | polaron | neutral | polaron | neutral | polaron | neutral | polaron |
|---|---|---|---|---|---|---|---|---|
| First-Excited State Energy (eV) | 3.00 | — | 3.68 | — | 3.15 | — | 3.64 | — |
| R1-R2 (Å) | 1.44 | 1.41 | 1.46 | 1.41 | 1.44 | 1.41 | 1.46 | 1.41 |
| R2-R3 (Å) | 1.44 | 1.41 | 1.44 | 1.41 | 1.46 | 1.41 | 1.47 | 1.44 |
| R3-R4 (Å) | — | — | — | — | 1.45 | 1.41 | 1.47 | 1.44 |
| R4-R5 (Å) | — | — | — | — | — | — | 1.46 | 1.42 |
| R1-R2 Dihedral | 177.2 | 178.3 | 91.5 | 164.4 | 174.8 | 179.7 | 86.8 | 167.3 |
| R2-R3 Dihedral | 177.2 | 178.3 | 175.2 | 178.8 | 111.6 | 151.4 | 121.5 | 137.7 |
| R3-R4 Dihedral | — | — | — | — | 174.8 | 179.7 | 125.6 | 132.5 |
| R4-R5 Dihedral | — | — | — | — | — | — | 83.7 | 169.1 |

Figure 12:
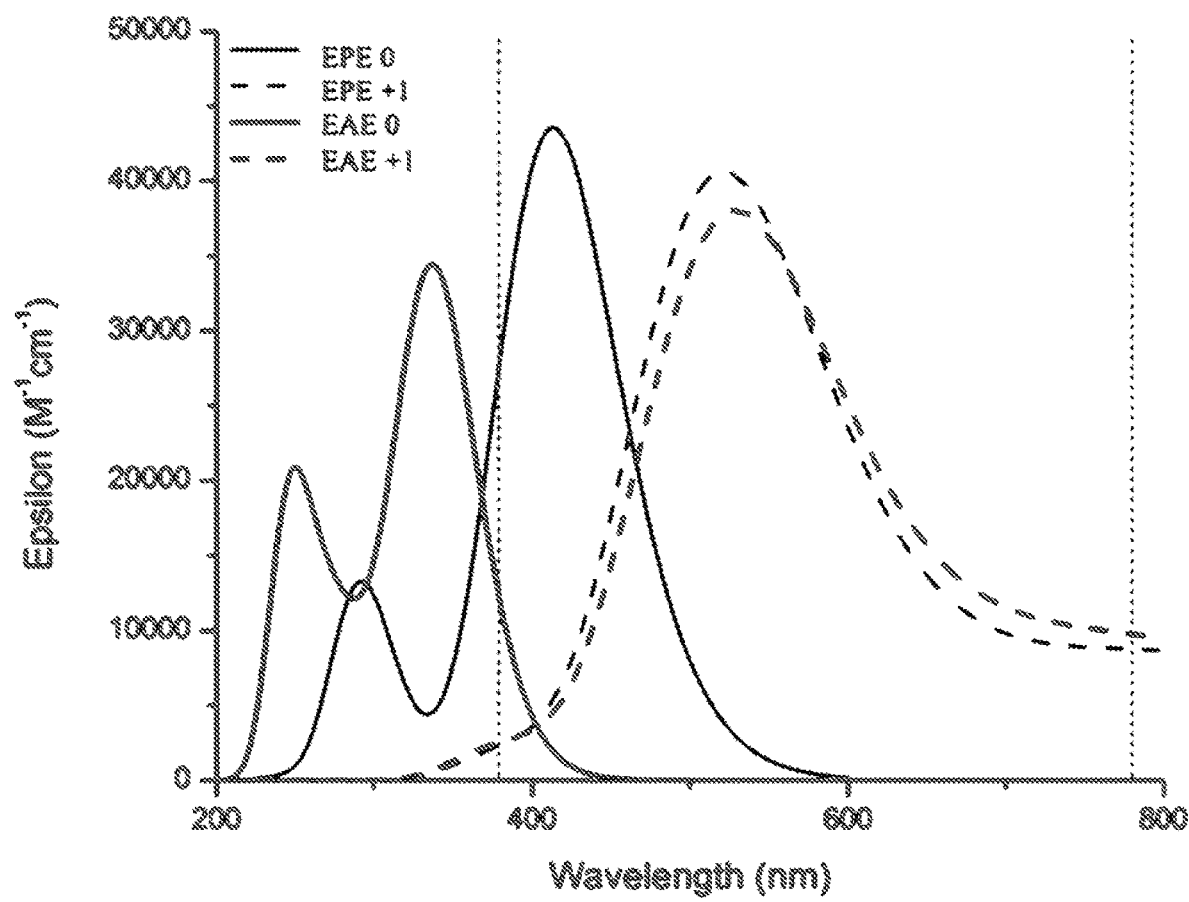
FIG. 12 is a plot of the UV-Vis spectra of EPE and EAE in the neutral (solid) and radical cation (dashed) states. Vertical dotted lines indicate the visible range of 380-780 nm.

The structural models for the ter(heterocycles) are corroborated with the analysis of the calculated UV-Vis spectra as depicted in FIG. 12. The absorption of EPE ($\lambda_{max}$=413 nm) occurs extensively throughout the visible due to a lack of interring strain, while the converse is observed for EAE ($\lambda_{max}$=337 nm). This comparative blue shift is attributed to the effective conjugation between only two of the three heterocycles in EAE. While the neutral spectra for each chromophore were unique, the radical cation spectra had surprisingly similar characteristics (energies and band widths). There were two peaks in the radical cation spectra for each chromophore, the higher energy peak indicative of the singly occupied molecular orbital (SOMO) to LUMO transition (b) and the lower for SOMO-n to SOMO (c) (note only the high energy radical cation peak is shown in FIG. 12. For the SOMO to LUMO transitions, there was only a 7 nm difference between the peak maxima of each chromophore. In the case of the lower energy transitions, peak maxima were 831 nm (EPE) and 809 nm (EAE) with similar oscillator strengths. These spectra demonstrate the ability to control the neutral state absorbance while producing nearly the same oxidized spectra. Thus, this theoretical experiment guides the focus of synthetic efforts towards highly strained acyclic systems to produce colorless neutral chromophores.

Quantum Chemical Calculations—Conjugation Vs. Strain.

Through the incorporation of excess strain, the absorption of a chromophore is driven into the UV-region. Additionally, increasing the conjugation by utilizing more aromatic systems in a single chromophore facilitates the polaronic spectrum to absorb broadly in the visible. To this end, the methyl-capped four and five ring chromophores shown in Scheme 6 were explored where the latter included dimethoxybenzene (B), which offers a high degree of strain and an inherently wider optical gap than thiophene-based systems due to an increased aromaticity.

Scheme 6. Structural scheme depicting the chromophores evaluated in the conjugation study.

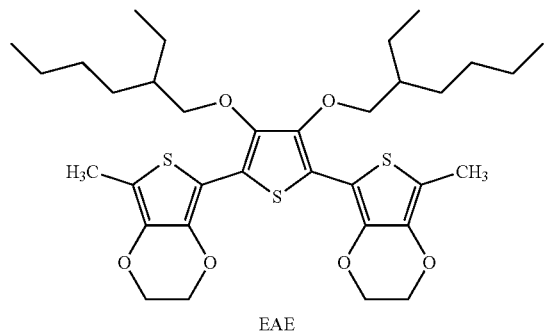

EAE

-continued

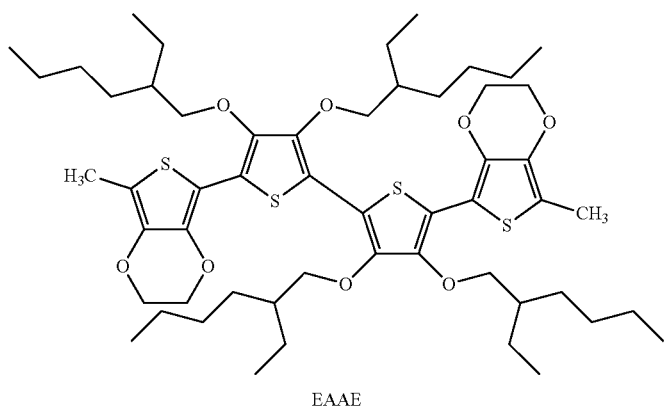

EAAE

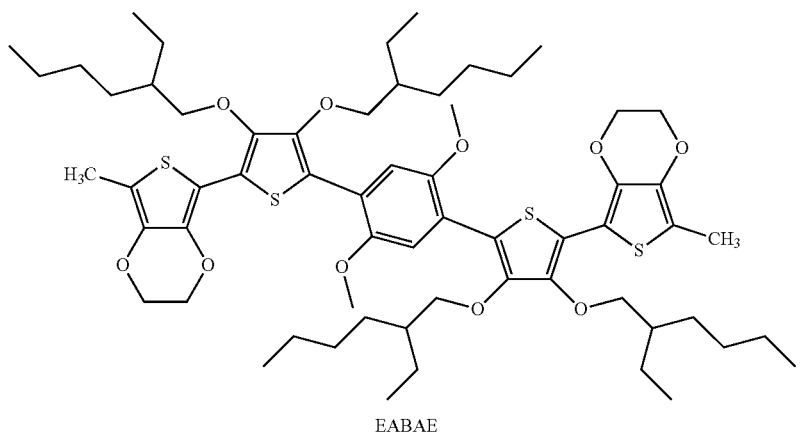

EABAE

Examining the neutral structural data in Table 1, it is evident that the EABAE system contains a significant amount of strain as the dihedral angles between each chromophore ranges between 83.7°-125.6°, limiting the conjugation along the backbone. For EAAE, the dihedral angles between each E and Ac heterocycles are exceptionally planar (174.8°) while the dihedral angle between the two Ac units exhibit considerable strain (111.6°). These effects are further reflected in the calculated UV-Vis spectra. In comparison to the neutral, low-energy peak of EAE, the peak for EAAE is red-shifted by 133 nm into the visible region making this chromophore undesirable. However, in the case of the EABAE, the simulated spectrum produces a single peak, which aligns with the low energy peak of EAE. The calculations for EABAE showed the primary transition occurs from HOMO→LUMO with an oscillator strength of 0.95. All other transitions had oscillator strengths less than 0.11 and were therefore negligible in the absorption spectrum. Upon closer analysis of the frontier molecular orbitals, the majority of electron density in the ground-state is delocalized on the EAB portion of the chromophore; in essence half of the molecule. Due to the increased strain along the backbone, the effective conjugation along the chromophore is compromised, producing an optical gap comparable to that observed in EAE.

Upon oxidation, all three chromophores become dramatically more planar. For the EAAE chromophore, the E-A dihedrals planarize to 179.7° and the A-A dihedral shifts to 151.4°. Similarly, for EABAE, the range of dihedral angles decreases to 132.5° to 169.1°. Each chromophore is found to absorb significantly in the visible in their oxidized states, particularly EAE with a peak maximum at 527 nm and broad absorption leading into the near IR. Similarly, EAAE exhibits a broad absorption leading into the near IR, however there is a prominent red-shift of 118 nm. Finally, EABAE has a single visible peak comprised of two excited states (474 nm and 514 nm), which is blue-shifted to EAE. Upon closer examination of all spectra, EAE and EABAE are the most promising electrochromic materials due to their high transmissivity coupled with visible absorption in their neutral and radical cation states, respectively.

Electrochemical and Optical Properties.

Figure 13A:
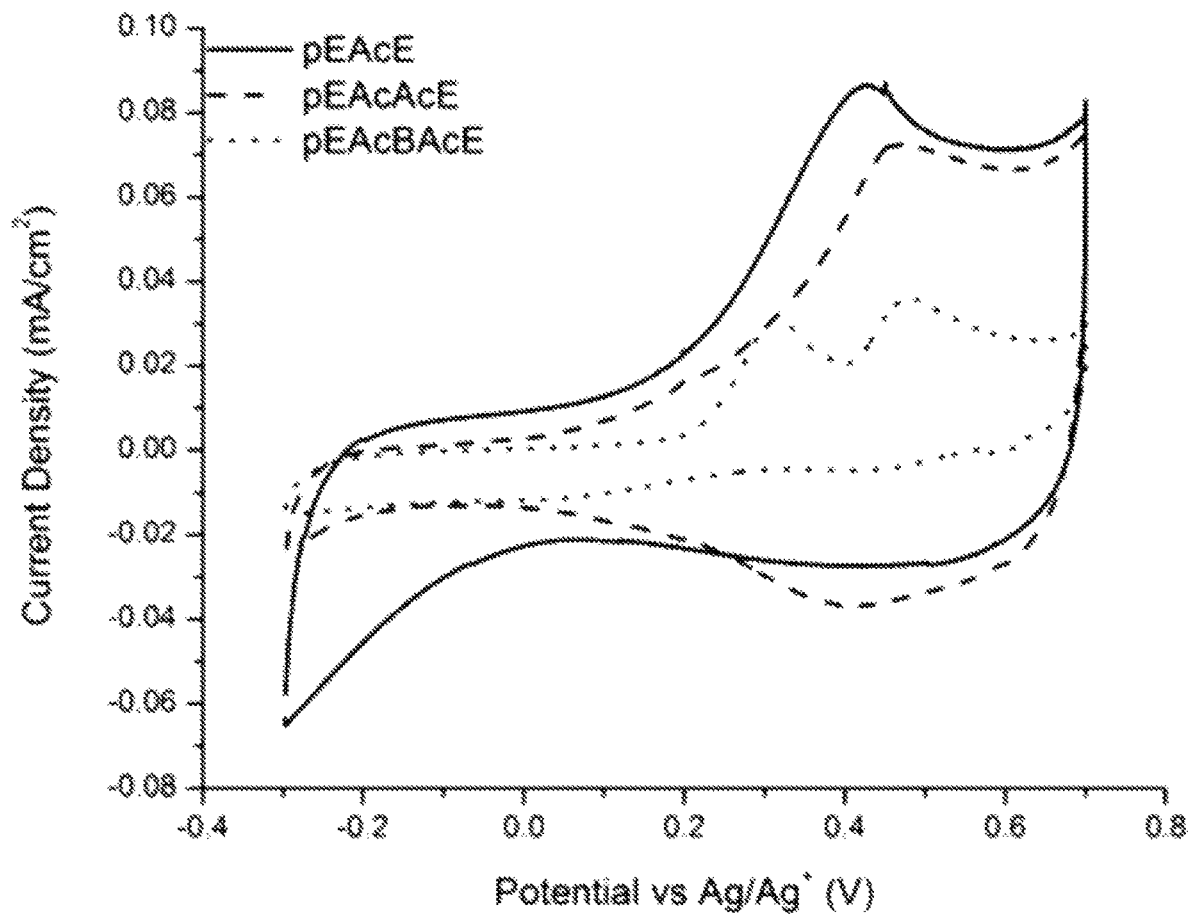
FIG. 13A is a DPV of thin films measured at 5 mV/sec.

All electrochemical measurements were performed on films that were drop cast (3 μL of 2 mg/mL solutions in $CHCl_3$) on glassy carbon electrodes in 0.5 M tetrabutylammonium hexafluorophosphate ($TBAPF_6$). Cyclic voltammetry (CV) and differential pulse voltammetry (DPV) were used to probe the redox properties of the target polymers as illustrated by the results in FIGS. 13A-13C. The onsets of oxidation measured via DPV were 0.13 V, 0.16 V, and 0.25 V for EAE, EAAE, and EABAE, respectively. This is counter-intuitive to the idea that increasing conjugation causes a raising of the HOMO and thus lower ionization potential, but is corroborated by the DFT calculations predicting this larger energy barrier to planarize for the A-A bond (Table 1). The strong A-A steric interaction in EAAE leads to a large planarization energy, which leads to a similar oxidation potential despite the increase in conjugation length. As predicted by the DFT calculations this steric effect is even more intense in the case of the EABAE leading to an even higher oxidation potential.

Figure 13B:
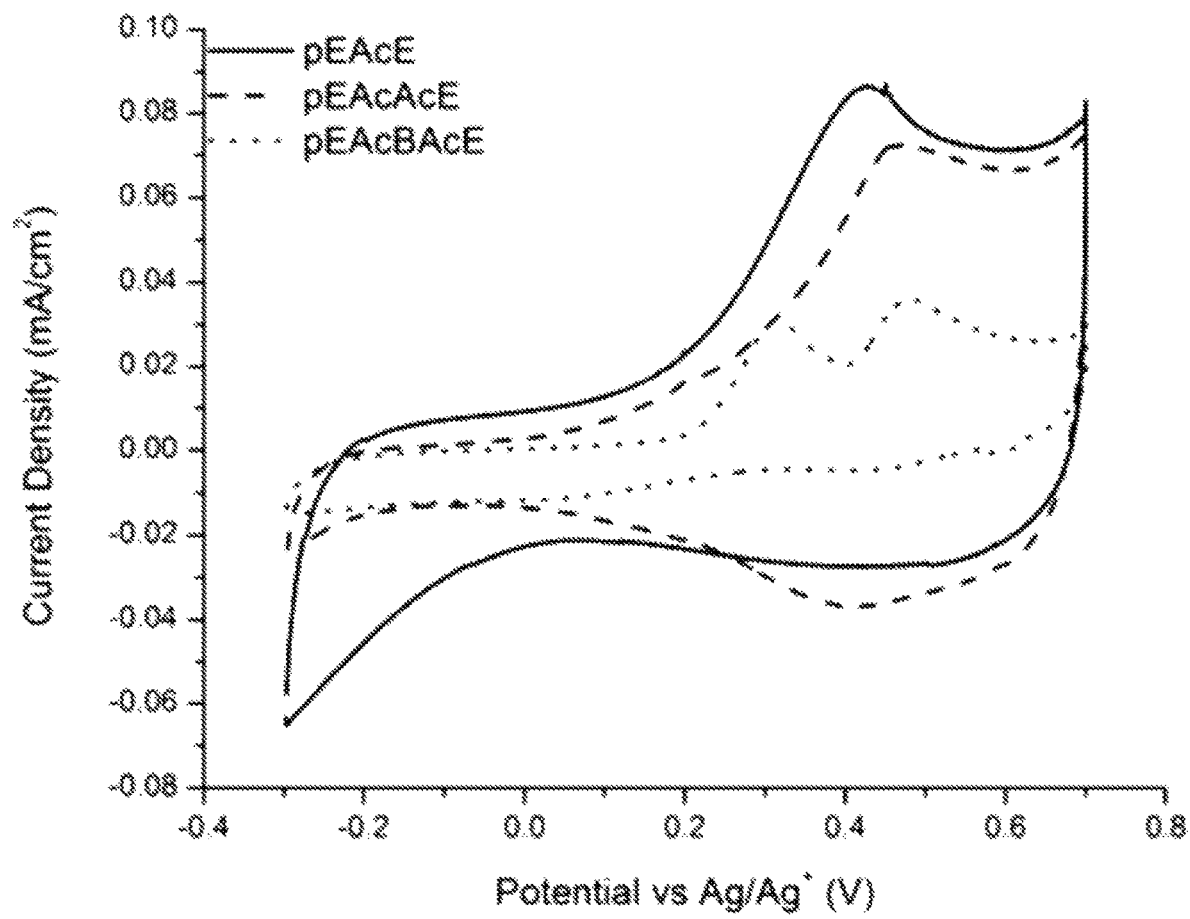
FIG. 13B is a CV (30th scan) of the polymer films from 0-0.7V vs. Ag/Ag+.
Figure 13C:
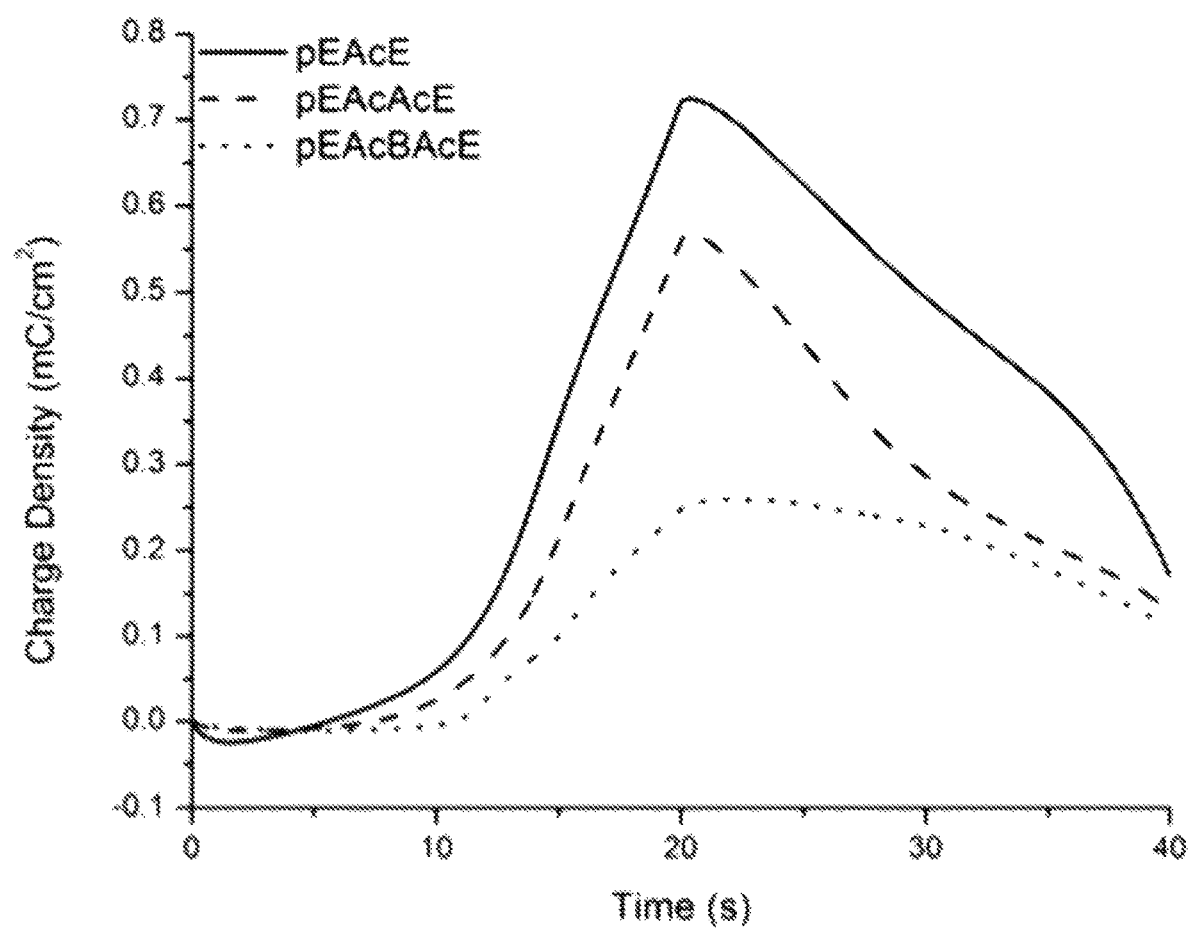
FIG. 13C is a graph of the charge passed through the film over the course of the 30th CV scan showing slow/incomplete reduction. (EAE-black, EAAE-red, EABAE-blue).
Figure 14:
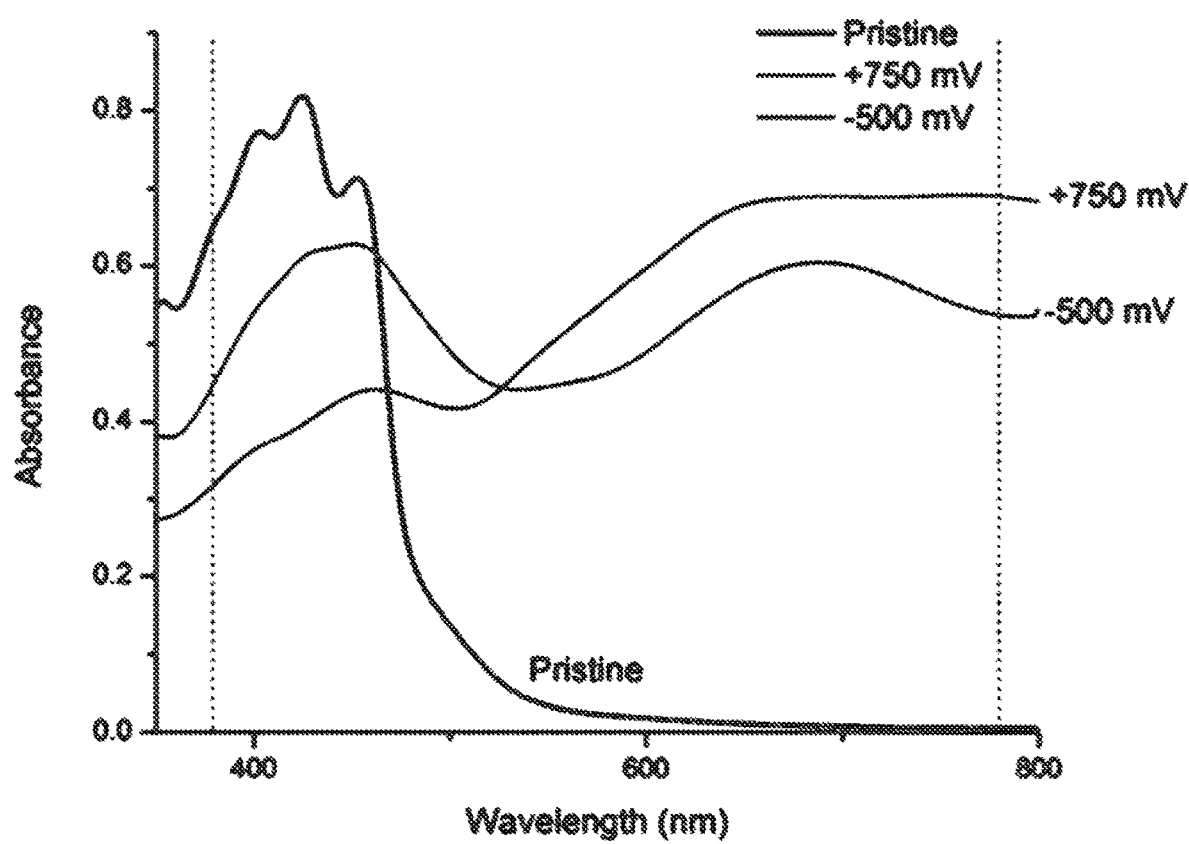
FIG. 14 is a spectra of EAAE showing the electrochemical irreversibility of the material upon oxidation.

Upon examination of the CVs in FIG. 13B, it becomes evident how similar EAE and EAAE behave electrochemically with one distinct oxidation. EABAE, on the other hand, has two distinct oxidations, suggesting further oxidation to a dication. Examination of the charge accumulation results in FIG. 13C, show both processes through a cycle of the CV to be partially irreversible for all polymers. This finding suggests trapped radical cation states in the film that cannot be fully reduced through electrochemical means. In order to ensure that the materials were not irreversibly degrading with the redox chemistry, the films were treated with hydrazine to successfully return them to their original oxidation state and color (FIG. 14). FIG. 14 shows the absorption of EAAE as a pristine film and the formation of a broad absorption upon oxidation at +750 mV. Upon the application of a reducing potential of −500 mV for 5 minutes, only some of the original absorption is regained. This can be seen as the material changes from a deep blue to a green in color as some low wavelength absorption returns. Upon removal of the electrodes and subsequent addition of hydrazine it can be seen from the photographs that the original color of the charge neutral state is returned.

This irreversible electrochemical response is a surprising observation based on the high electroactivity of multi-heterocycle, broken conjugation linear polymers and acrylate coatings. Not wishing to be bound by any particular theory, it could be that as the polymer film is being oxidized, the chromophore layer closest to the electrode is oxidized first, elevating its conductivity. This increase in conductivity facilitates charge hopping between chromophores through the film, thus oxidizing the bulk. Application of a reducing potential causes this first layer of chromophores to reduce to their neutral, insulating states. This neutral layer acts as an insulating barrier preventing reduction of the remaining charged states in the polymer. These films can be fully reduced back to the neutral with the addition of a chemical reductant, but the fully neutral form cannot be re-obtained based purely on electrochemical reduction. This type of behavior is not useful for typical electrochromic applications, but could have potential use as a visual fuse that switches upon reaching an overpotential (Janata, *Principles of chemical sensors*, Springer Science & Business Media, 2010; M. C. Gallazzi, L. Tassoni, C. Bertarelli, G. Pioggia, F. Di Francesco and E. Montoneri, *Sensors Actuators B Chem.*, 2003, 88, 178-189; R. Rella, P. Siciliano, F. Quaranta, T. Primo, L. Valli and L. Schenetti, *Colloids Surfaces A Physicochem. Eng. Asp.*, 2002, 198-200, 829-833; M. F. Mabrook, C. Pearson and M. C. Petty, *Appl. Phys. Lett.*, 2004, 86, 13507). This fuse would remain in the new colored state until chemically reduced to the neutral state.

Figure 15A:
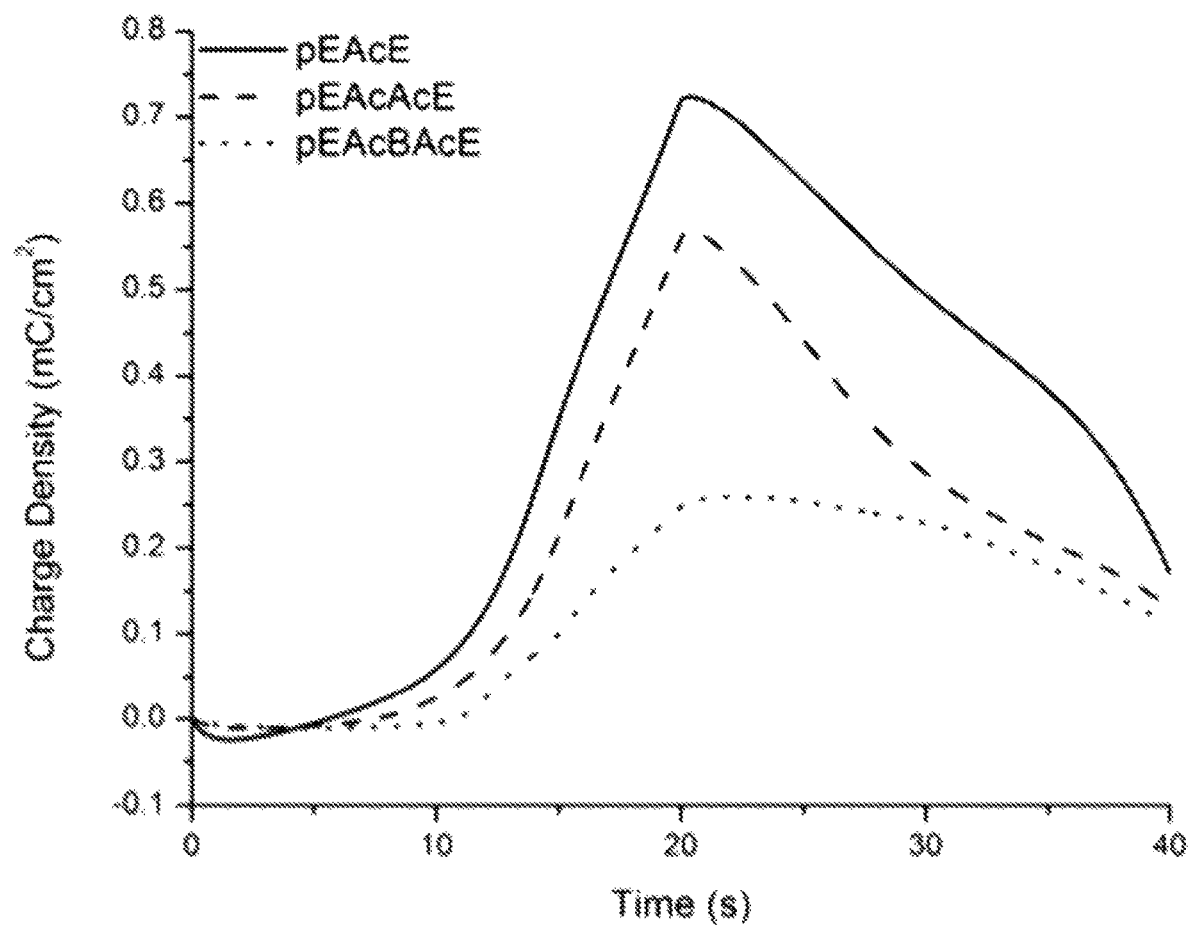
FIG. 15A is a normalized solution UV/Vis absorbances of the polymers.

The energy and width of the radical cation absorption spectra and how the switching potentials can be tuned as they relate to the chromophores' structures are important in understanding these types of systems. To this end, the absorption properties of these polymers were investigated. The UV/Vis spectra of the polymers were measured in a solution of 40 µg/ml in dichloromethane (DCM), normalized for FIG. 15A. Contrary to the DFT calculations there is a red-shifting of the chromophores' absorbances increasing the conjugation of the dioxythiophene chromophores with $\lambda_{max}$ for EAE and EAAE being 386 nm and 424 nm, respectively. However, due to the large steric strain between the AcDOTs and dimethoxybenzene in EABAE, the chromophore is twisted thereby lowering the extent of conjugation and a lower $\lambda_{max}$ of 395 nm.

Figure 15B:
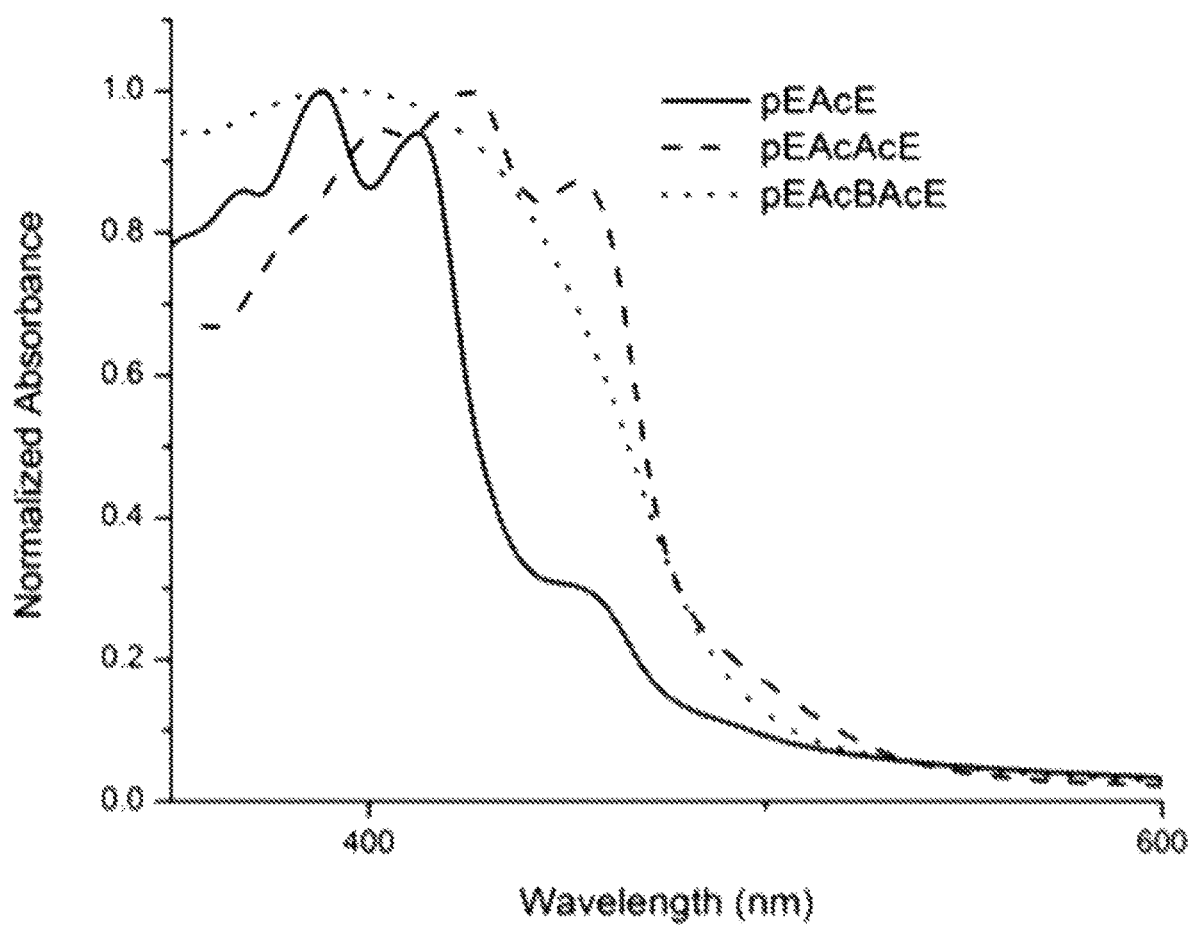
FIG. 15B is a normalized thin film absorbances of the polymers. (EAE-solid, EAAE-dash, EABAE-dot). It can be seen that the absorption onset for these materials is redshifted moving to the solid state with a greater degree of broadening for EABAE indicative of more chromophore-chromophore aggregation.

To probe the spectral changes of the polymers during oxidation, films were spray coated onto ITO/glass using a hand-held airbrush from 3 mg/mL polymer-toluene solutions to an absorbance of 0.8-1.0 AU. As can be seen in FIG. 15B, the normalized absorbance for the all of the polymers is largely unchanged relative to the solution spectra, other than peak broadening. This broadening is more significant in the case of EABAE causing it to adopt an absorption onset closer to that of EAAE.

Film Spectroelectrochemistry and Colorimetry.

Figure 16A:
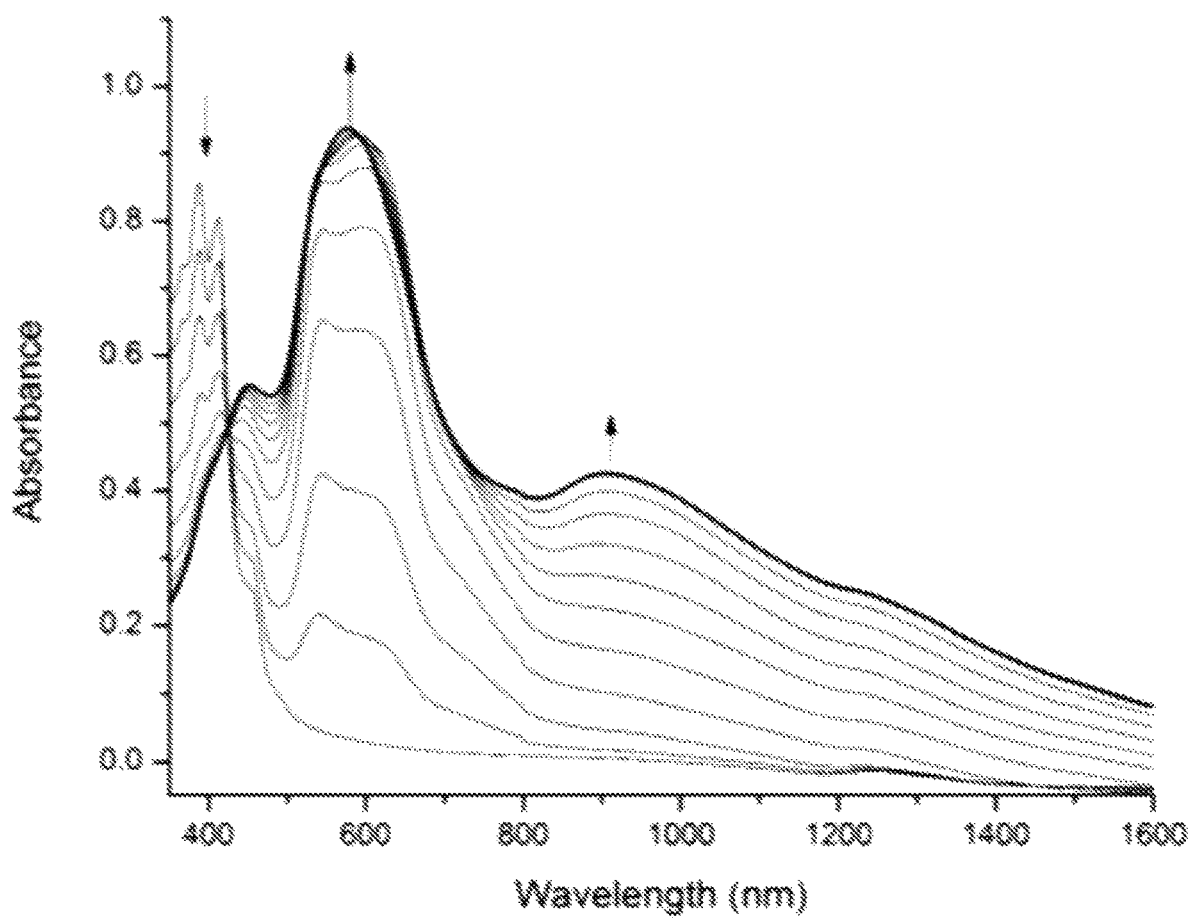
FIGS. 16A-16C are graphs of the spectroelectrochemistry of polymer films on ITO-glass in 0.5 M TBAPF6-PC with potential steps of 50 mV from the pristine to the fully oxidized form. (EAE (FIG. 16A), EAAE (FIG. 16B), EABAE (FIG. 16C)).
Figure 16B:
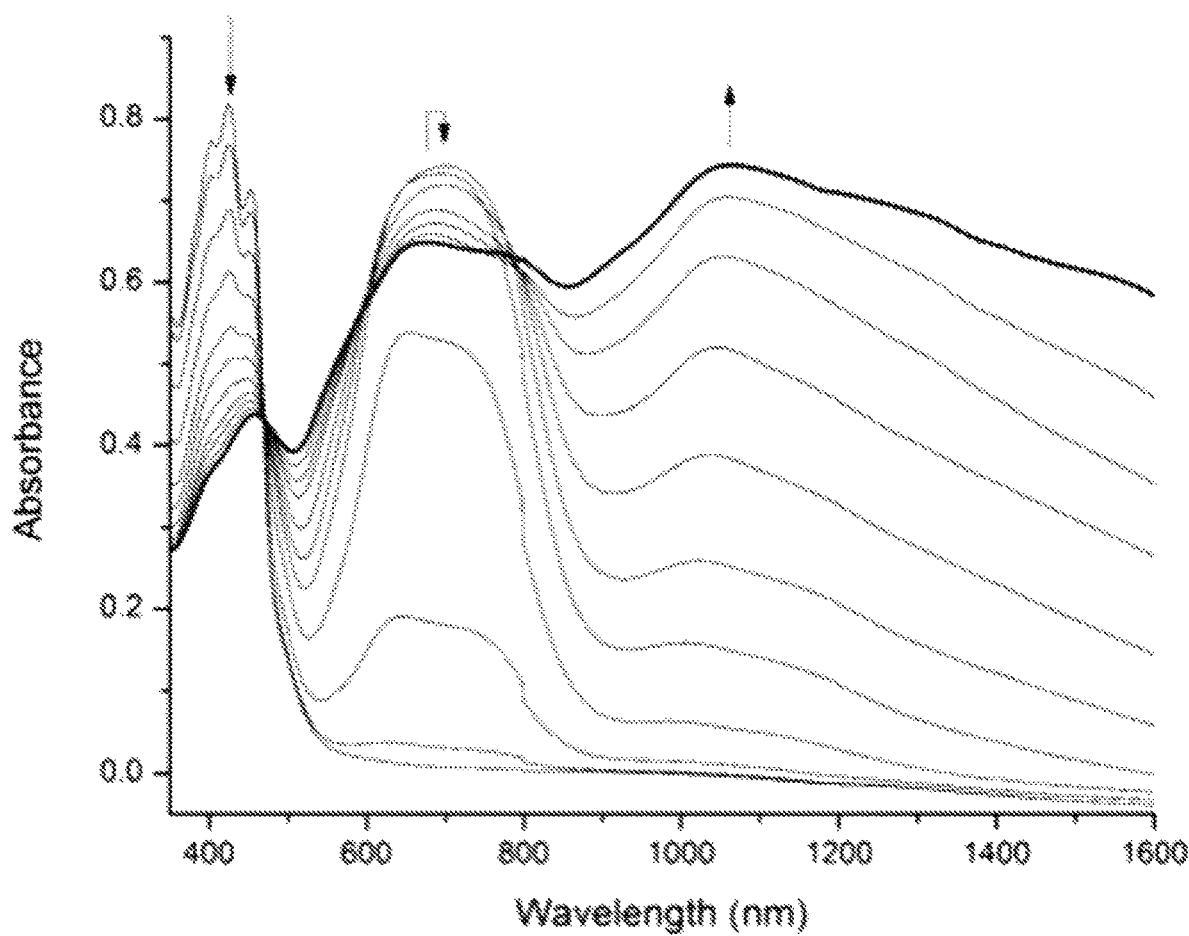
Figure 16C:
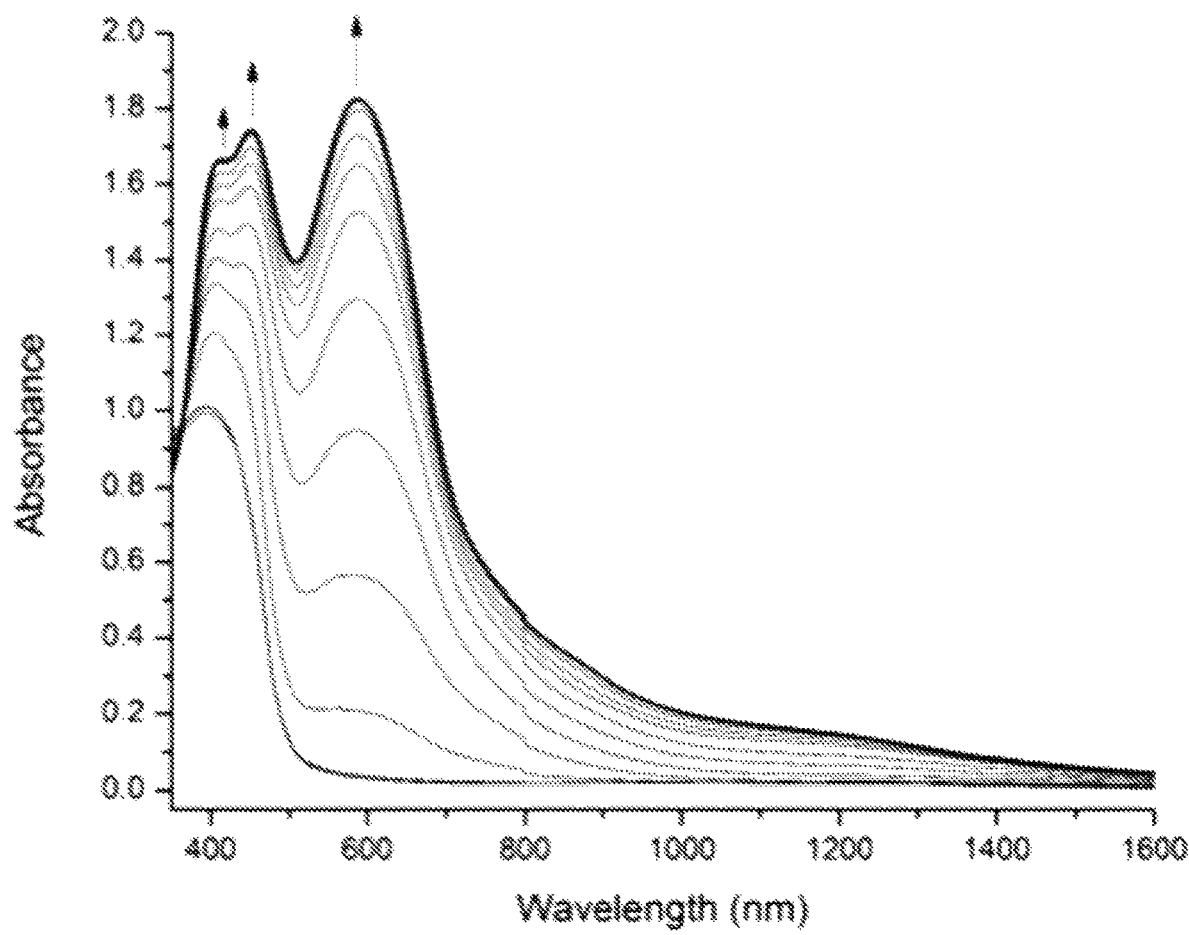

Spectroelectrochemical measurements were performed in 0.5 M TBAPF$_6$ in propylene carbonate with a platinum counter electrode and a Ag/Ag$^+$ reference electrode as shown in FIGS. 16A-16C along with photographs of the films held at potential extremes dictated by the CVs results. As a pristine film, EAE shown in FIG. 15A absorbs at a $\lambda_{max}$ of 386 nm (i) capturing only a small portion of the visible giving a pale yellow color. Oxidation of EAE to the radical cation state reduces the intensity of peak 'i' and gives rise to a sharp absorbance with at $\lambda_{max}$ 582 nm (ii) centered in the visible with a less intense peak in the near IR at 935 nm (iii). This new oxidation state is perceived as blue as the lower energy red and green light is absorbed and blue is transmitted.

Turning attention to FIG. 16B the neutral absorbance of EAAE is redshifted compared to EAE with a $\lambda_{max}$ at 424 nm (iv), thus absorbing more blue light and creating a deeper yellow color. Upon oxidation of EAAE, the neutral peak 'iv' reduces in intensity and the polymer radical cation begins to absorb in the visible at $\lambda_{max}$ at 687 nm (v) and in the near IR at 1050 nm (vi), both redshifted compared to EAE as predicted by calculations. Upon further oxidation, peak 'v' begins to decrease in intensity with the continued growth of a broadly absorbing peak 'vi' in the near-IR indicative of a dication species. This charged state has some absorbance of lower energy red light, allowing more green and blue light to transmit, and is perceived as a teal-turquoise color.

With increasing conjugation it was expected that EABAE would have a neutral peak red-shifted compared to the two shorter chromophores, but the steric repulsion between the dimethoxybenzene and AcDOTs cause a decrease of π overlap in the center of the chromophore, widening the optical gap, and giving rise to an absorption with $\lambda_{max}$ at 395 nm (vii). This absorbance profile yields a film that is similar in appearance to that of EAAE. Upon oxidation of EABAE there is the growth of two sharp and intense peaks with $\lambda_{max}$ at 450 nm (viii) and 587 nm (ix). The combined absorbance of these peaks allows for this charged state absorption to encompass a large portion of the visible range causing the film to appear as a dark black. Note that the intensity of the absorbance in this material's oxidized state is much higher than that of the neutral state. Not wishing to be bound by any particular theory, it could be that this large increase in intensity and the high energy of the absorptions compared to the all dioxythiophene chromophores are likely from two different radical cation species or the formation of radical cation aggregates.

Colorimetry.

Figure 17:
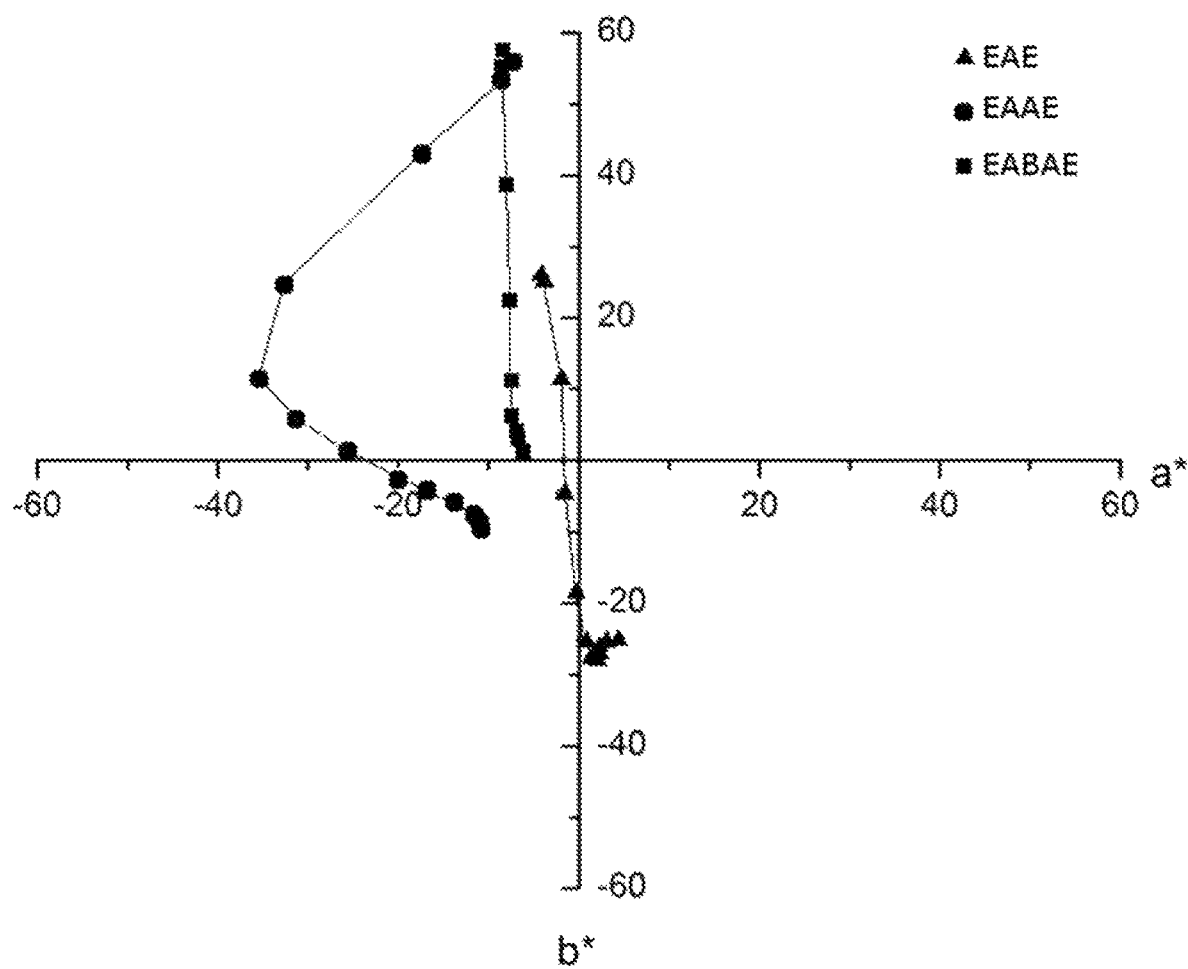
FIG. 17 is a graph showing progression of L*a*b* color coordinates of polymer films from pristine to oxidized (EAE-triangles, EAAE-circles, EABAE-squares).

The L*a*b* color space results for the polymers under study are presented graphically in FIG. 17 with the values collated in Table 2. In this color space, positive a* and b* represents red and yellow while the negative values indicate blue and green, respectively. As the magnitudes of a* and b* increase, the color becomes more saturated, and as one traverses between color points, the hue changes. L* depicts the lightness: a value of 0 would be black and 100 would be white.

In the neutral state, EAE is a low saturation yellow (b*=26) with a high lightness value (L*=96), due to the minimal absorbance tailing into the high-energy side of the visible spectrum. Comparatively, EAAE and EABAE have L* and a* values similar to EAE, but are much more saturated (higher b*) observed by their more intense yellow color. Upon oxidation, EAE passes through the origin along the b* axis to create a blue radical cation state with a similar saturation to that of the neutral form with a much lower L* value, 45. EAAE follows the formation of a green radical cation state with a largely negative a* value, and upon further oxidation the color coordinates move towards the origin to make a low saturation blue-green color at 750 mV. For EABAE the formation of the two radical species causes the loss of color saturation and an oxidized state with color coordinates close to the origin (colorless). The L* value dropping to 18 indicates a low percentage of light transmitting across the visible. This appears to the eye as a dark, black film.

TABLE 2

Color coordinate values for the pristine and oxidized states of the polymer films.

| Polymer | Pristine L*, a*, b* | Radical Cation L*, a*, b* |
|---|---|---|
| EAE | 96, −4, 26 | 45, 4, −25 |
| EAAE | 96, −7, 56 | 64, −12, −7 |
| EABAE | 95, −8, 57 | 18, −6, 1 |

Charge State Elucidation of EABAE.

In the spectroelectrochemistry for EABAE the charged state exhibited an unusually high-energy absorption characteristic compared to what was calculated. To elucidate the unusual charge state for this chromophore, computational methods were utilized. For this calculation, the chromophore is broken into pieces with the idea that the dimethoxybenzene would act as a steric block in the conjugation of the radical cation. Calculated radical cation state absorptions of segmented portions of the EABAE chromophore and the experimental spectroelectrochemistry suggest that there are two main phenomena contributing to the radical cation spectra: twisted/conjugation broken chromophores and π-π stacking. As demonstrated by the frontier molecular orbitals, the computations strongly support that the two experimental peaks at 412 nm and 452 nm are contributions from the two-ring dioxythiophene portions of the chromophore (EA, 405 nm) and the three-ring fraction (EAB, 456 nm), respectively. Surprisingly, the results did not support any major influences from the full chromophore (EABAE, 496 nm). In an effort to identify the contributor(s) to the 587 nm peak, a radical cation π-dimer comprised of EA and EAB units was generated. This aggregate, producing a 562 nm peak, provides strong support that intermolecular π-π stacking is likely responsible for the low energy peak.[49-52] Other combinations were also examined, but were unable to produce optimized aggregates and therefore require further studies.

Conclusions and Perspective

The contrast challenge for cathodically coloring electrochromics is examined from a fundamental standpoint leading to the determination that anodically coloring materials provide a means to conquer the issue. This example focused on examining the design principles of creating chromophores with discrete lengths and varying amounts of strain. Theoretical calculations, coupled with design and synthesis, helped to elucidate the interplay between sterics and chromophore size. Inter-ring steric interactions, leading to large dihedral angles, can be used as a conjugation wedge to limit, not only the neutral absorption, but also the delocalization of charged states creating radical cations that absorb at high energies compared to chromophores of similar size, but less steric encumbrance. The use of steric interactions as a conjugation block also gives the advantage of forming multiple and different high-energy light absorbing charged states. Considering the broad absorption achieved by the apparent dimerization of the EABAE chromophore attention should be shifted towards designing molecules for this purpose. The electrochemical irreversibility does appear to be a problem for purely electrochromic applications, but it does however appear to offer an interesting approach toward making materials that could be used as overpotential fuses.

Example 4: Anodically Coloring Electrochromic Polymers Based on Heteroatom-Linked Discrete Chromophore Polymers Synthesis.

Polymers with discrete chromophores that are conjugation broken by heteroatoms were synthesized as described in Scheme 7. The polymerizations were carried out via a direct heteroarylation mechanism with the respective dibromo monomers to create the polymers with discrete chromophores (similar to Example 3). The polymers were purified via Soxhlet extraction and the repeat unit structure confirmed using $^1$H and $^{13}$C NMR and elemental analysis. Polymer molecular weights were analyzed with gel-permeation chromatography (GPC) in $CHCl_3$ at 40° C. and the number average molecular weights and dispersity ($M_n$, Đ) relative to polystyrene standards are as follows: POP-AA (33.5 kDa, 2.4) and POP-P (18.5 kDa, 2.1).

Scheme 7. Synthetic scheme outlining the synthesis of the target polymers.

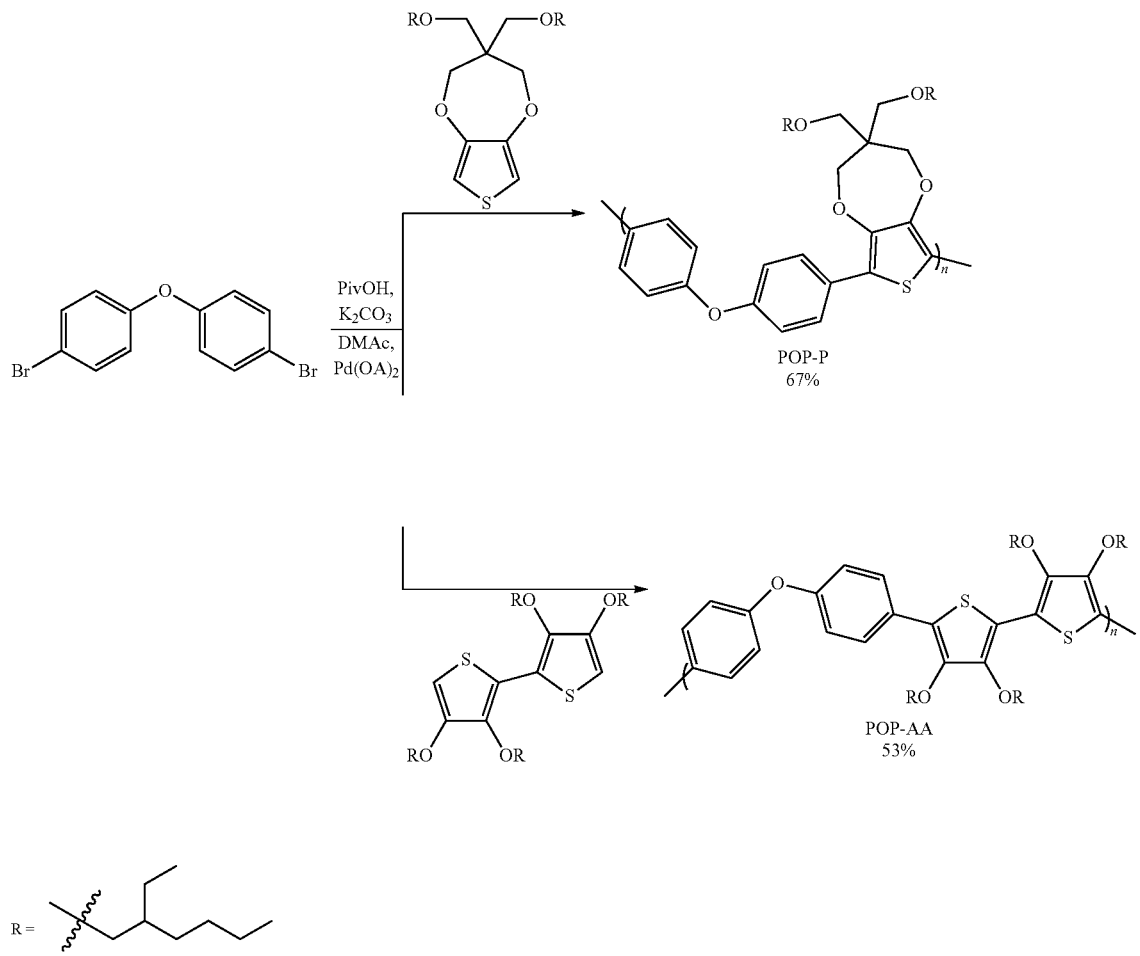

Figure 18A:
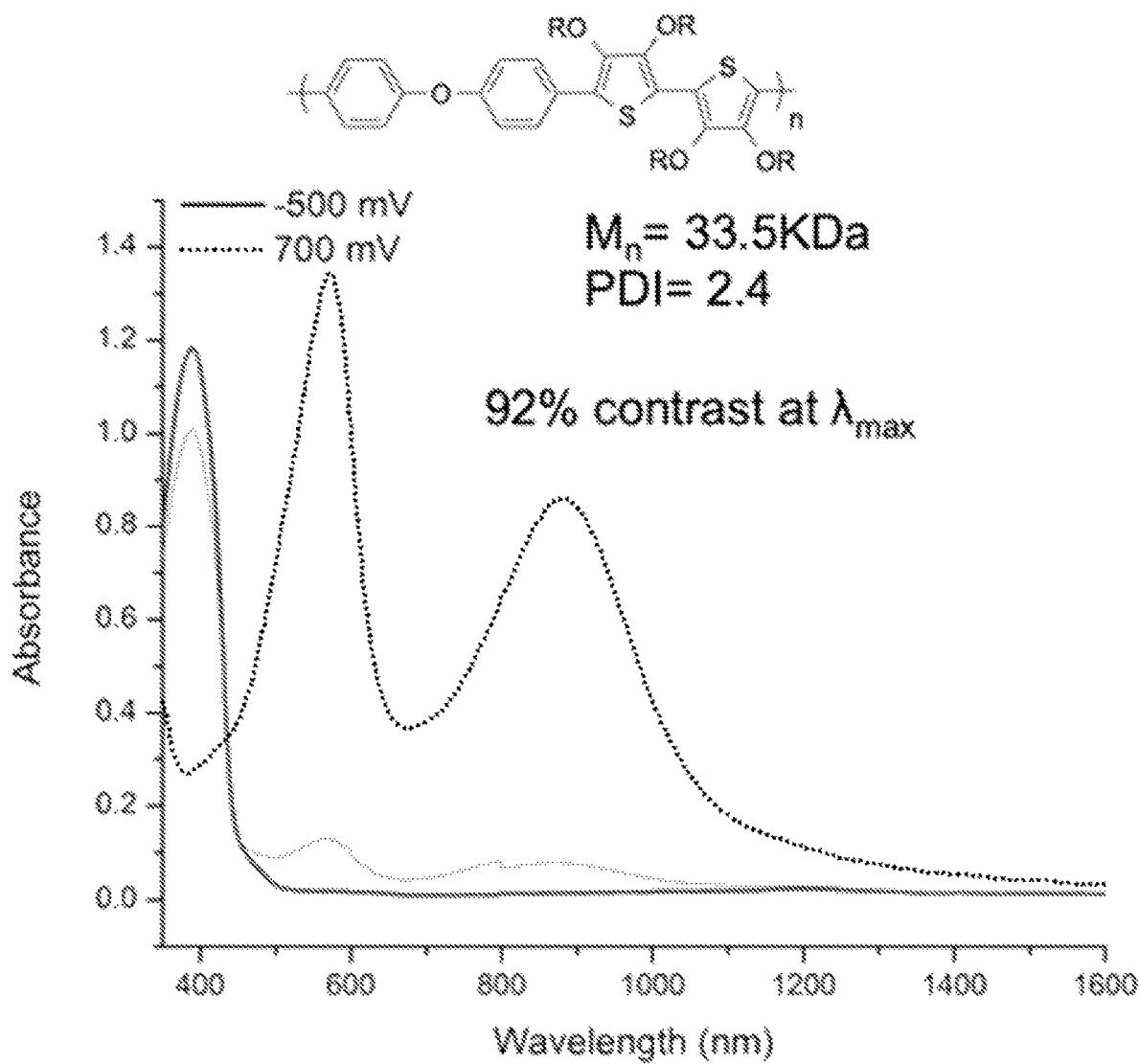
FIGS. 18A-18B are graphs of the spectroelectrochemistry (FIG. 18A) and cyclic voltammetry (FIG. 18B) of POP-AA films on ITO-glass in 0.5 M TBAPF6-PC.
Figure 18B:
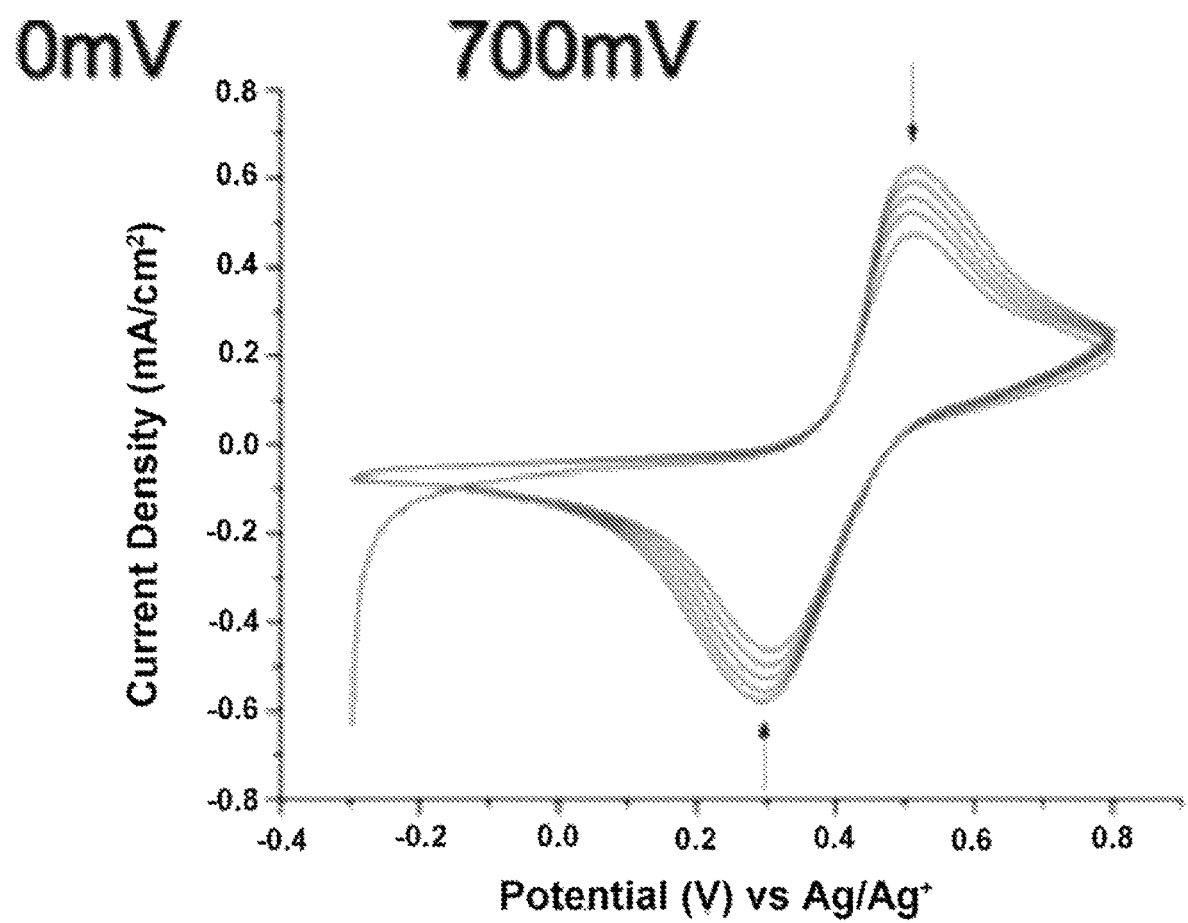
Figure 19A:
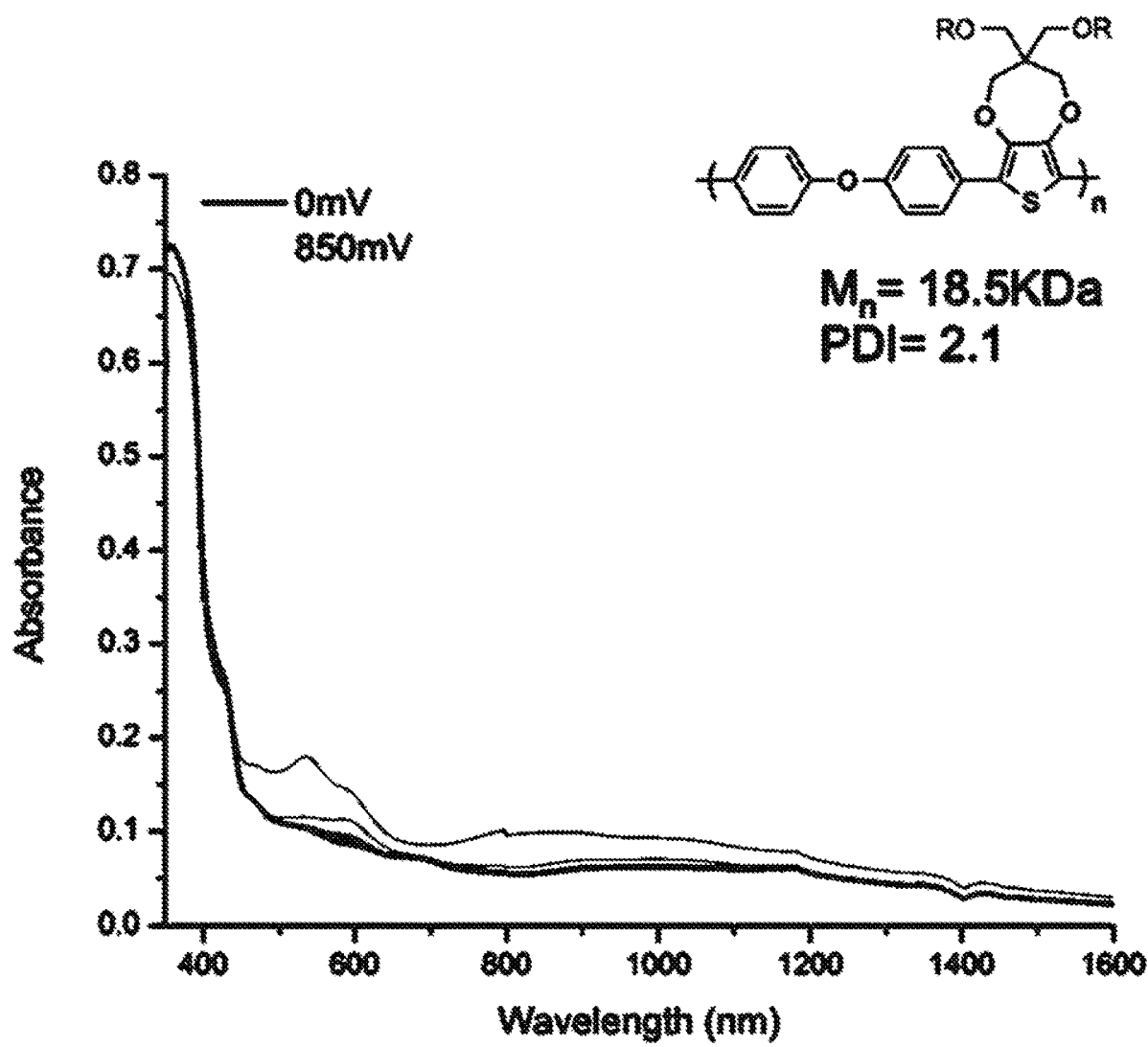
FIGS. 19A-19B are graphs of the spectroelectrochemistry (FIG. 19A) and cyclic voltammetry (FIG. 19B) of POP-P films on ITO-glass in 0.5 M TBAPF6-PC.
Figure 19B:
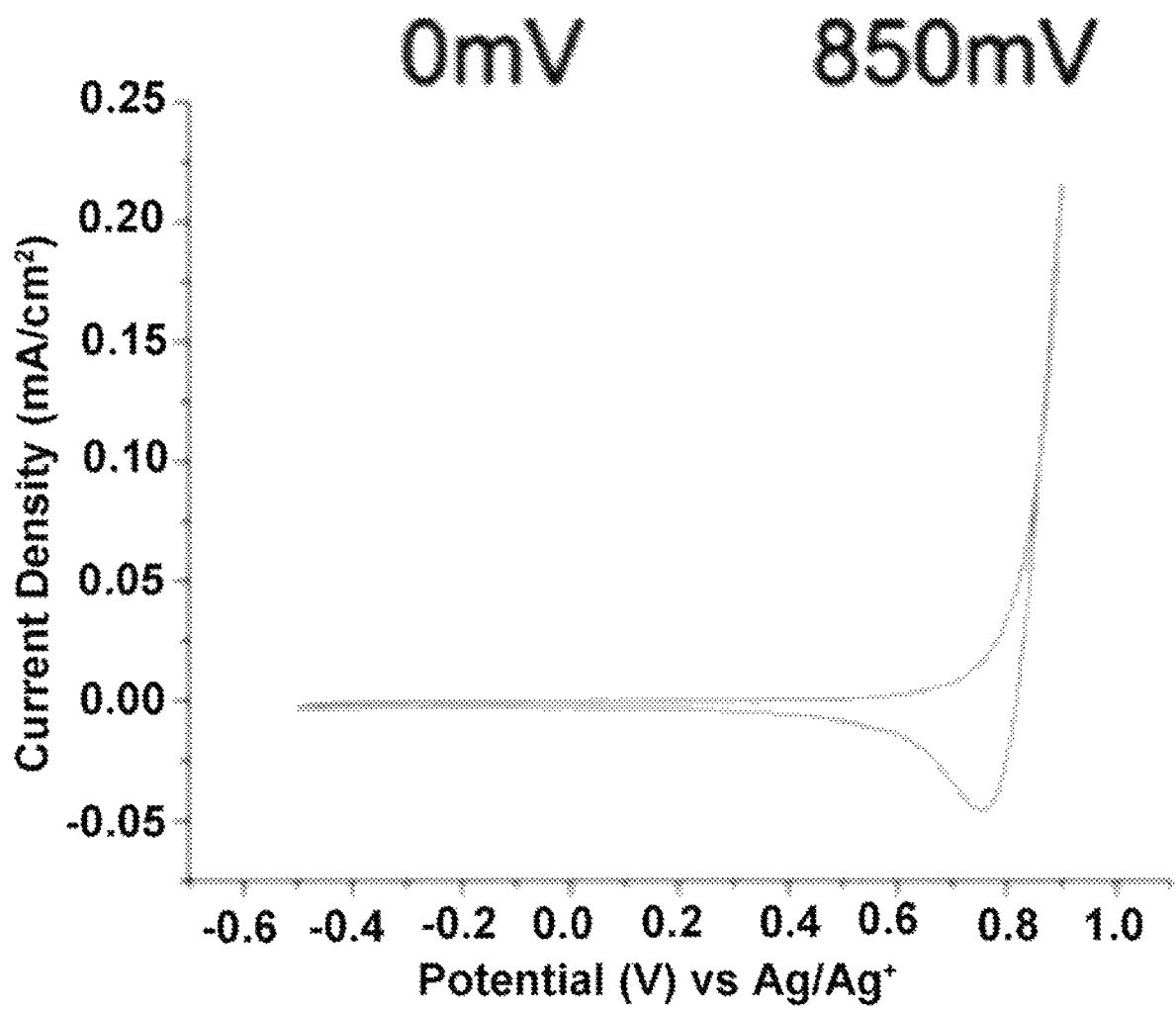

The spectroelectrochemical results for POP-AA is shown in FIG. 18A where upon oxidation the radical cation absorption gives rise to two peaks at 570 nm and 889 nm leading to a purple color. This polymer reaches an ultimate contrast of 92% which is a groundbreaking contrast for an electrochromic polymer. The CV shown in FIG. 18B shows that there is reversibility in switching, but it may be limited to a certain number of cycles. The spectroelectrochemical results for the shorter conjugation length chromophore POP-P can be seen in FIG. 19A where upon oxidation the radical cation gives rise to two peaks at 540 nm and 810 nm leading to a red color. The CV shown in FIG. 19B shows that the oxidation potential is higher than that of POP-AA and the reversibility in switching may be limited to a certain number of cycles.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:
1. An electrochromic device comprising:
(a) a first electrode;
(b) a second electrode;
(c) an electrolyte sandwiched between the first electrode and the second electrode; and
(d) an anodically-coloring electrochromic molecule selected from the group consisting of

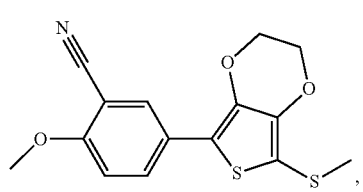

ACE1

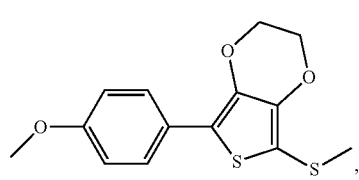

ACE2

ACE3

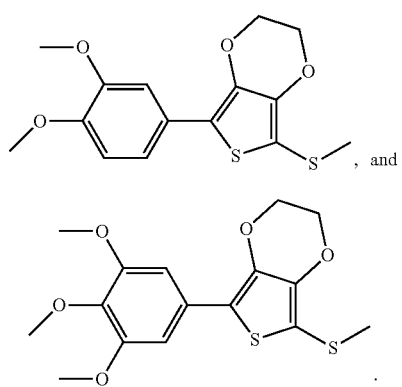

, and

ACE4

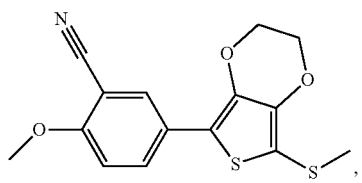

.

2. The electrochromic device according to claim 1, wherein the anodically-coloring electrochromic molecule is dispersed within the electrolyte.

3. The electrochromic device according to claim 1, wherein the anodically-coloring electrochromic molecule is covalently attached to a surface of the first electrode that is in contact with the electrolyte.

4. An anodically-coloring electrochromic molecule selected from the group consisting of

ACE1

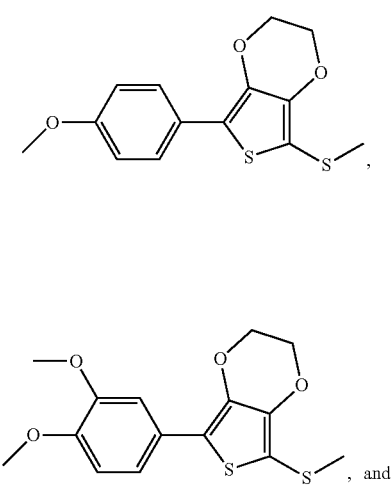

,

ACE2

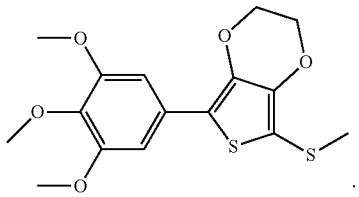

,

ACE3

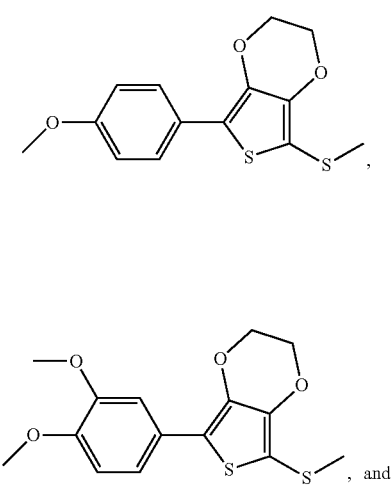

, and

ACE4

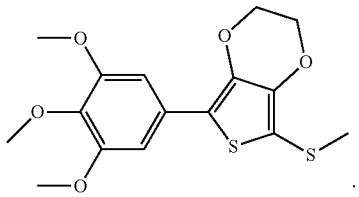

.

* * * * *